United States Patent
Bruce et al.

(10) Patent No.: US 9,751,876 B2
(45) Date of Patent: *Sep. 5, 2017

(54) BICYCLIC HETEROCYCLE DERIVATIVES FOR THE TREATMENT OF PULMONARY ARTERIAL HYPERTENSION

(71) Applicant: Novartis AG, Basel (CH)

(72) Inventors: Ian Bruce, Horsham (GB); Sylvie Chamoin, Saint Louis (FR); Stephen Paul Collingwood, Haywards Heath (GB); Pascal Furet, Thann (FR); Vikki Furminger, Seaford (GB); Diana Janus, Horsham (GB); Sarah Lewis, Cambridge, MA (US); Jon Christopher Loren, San Diego, CA (US); Valentina Molteni, San Diego, CA (US); Alex Michael Saunders, Leicester (GB); Duncan Shaw, Sharon, MA (US); Lilya Sviridenko, Shalford (GB); Christopher Thomson, Belmont, MA (US); Ryan West, Horsham (GB); Vince Yeh, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/511,044

(22) Filed: Oct. 9, 2014

(65) Prior Publication Data

US 2015/0025059 A1    Jan. 22, 2015

Related U.S. Application Data

(62) Division of application No. 13/599,267, filed on Aug. 30, 2012, now Pat. No. 8,883,819.

(60) Provisional application No. 61/680,119, filed on Aug. 6, 2012, provisional application No. 61/530,049, filed on Sep. 1, 2011.

(51) Int. Cl.
| | | |
|---|---|---|
| *C07D 471/04* | (2006.01) | |
| *A61K 31/444* | (2006.01) | |
| *A61K 31/4545* | (2006.01) | |
| *A61K 31/496* | (2006.01) | |
| *A61K 31/5377* | (2006.01) | |
| *A61K 45/06* | (2006.01) | |
| *A61K 31/4745* | (2006.01) | |

(52) U.S. Cl.
CPC .......... *C07D 471/04* (2013.01); *A61K 31/444* (2013.01); *A61K 31/4545* (2013.01); *A61K 31/4745* (2013.01); *A61K 31/496* (2013.01); *A61K 31/5377* (2013.01); *A61K 45/06* (2013.01)

(58) Field of Classification Search
CPC .............. A61K 31/444; A61K 31/4545; A61K 31/4745; A61K 31/496; A61K 31/5377; A61K 45/06; C07D 471/04
See application file for complete search history.

(56) References Cited

U.S. PATENT DOCUMENTS

| | | |
|---|---|---|
| 2005/0054701 A1 | 3/2005 | Wallace et al. |
| 2007/0072862 A1 | 3/2007 | Dimauro et al. |
| 2010/0093718 A1 | 4/2010 | Berdini et al. |
| 2013/0059846 A1 | 3/2013 | Yeh et al. |

FOREIGN PATENT DOCUMENTS

| | | |
|---|---|---|
| EP | 0 033 094 | 8/1981 |
| WO | 9932477 | 7/1999 |
| WO | 0007980 | 2/2000 |
| WO | 0007991 | 2/2000 |

(Continued)

OTHER PUBLICATIONS

Bhatt et. al., Chemical Communications, 2005, The Royal Society of Chemistry, pp. 1073-1075.*

(Continued)

*Primary Examiner* — Sarah Pihonak
(74) *Attorney, Agent, or Firm* — Shawn D. Britt

(57) ABSTRACT

Bicyclic heterocyclic derivatives of formula I useful in inhibiting PDGF receptor mediated biological activity.

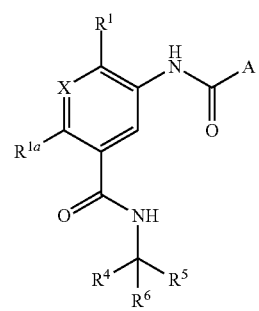

wherein A is

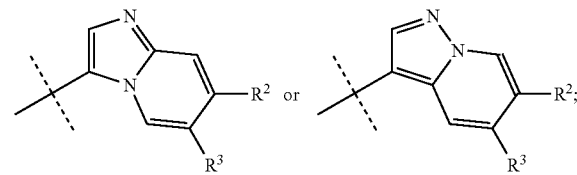

and $R^1$, $R^{1a}$, $R^2$, $R^3$, $R^4$, $R^5$, $R^6$ and X are as defined herein.

18 Claims, No Drawings

(56) References Cited

FOREIGN PATENT DOCUMENTS

| WO | 0055120 | 9/2000 |
| WO | 0119788 | 3/2001 |
| WO | 0127089 | 4/2001 |
| WO | 02066477 | 8/2002 |
| WO | 02066478 | 8/2002 |
| WO | 03078435 | 9/2003 |
| WO | 2004026867 | 4/2004 |
| WO | 2004026872 | 4/2004 |
| WO | 2004063330 | 7/2004 |
| WO | 2004087646 | 10/2004 |
| WO | 2004101563 | 11/2004 |
| WO | 2005023759 | 3/2005 |
| WO | 2005044797 | 5/2005 |
| WO | 2005048953 | 6/2005 |
| WO | 2005063739 | 7/2005 |
| WO | 2005085227 | 9/2005 |
| WO | 2006032342 | 3/2006 |
| WO | 2006067445 | 6/2006 |
| WO | 2006067446 | 6/2006 |
| WO | 2006081172 | 8/2006 |
| WO | 2006101455 | 9/2006 |
| WO | 2006108640 | 10/2006 |
| WO | 2007022380 | 2/2007 |
| WO | 2007032936 | 3/2007 |
| WO | 2007065664 | 6/2007 |
| WO | 2007113226 | 10/2007 |
| WO | 2007149395 | 12/2007 |
| WO | 2008008539 | 1/2008 |
| WO | 2008009487 | 1/2008 |
| WO | 2008058037 | 5/2008 |
| WO | 2008064157 | 5/2008 |
| WO | 2008086014 | 7/2008 |
| WO | 2008134553 | 11/2008 |
| WO | 2008144253 | 11/2008 |
| WO | 2008150015 | 12/2008 |
| WO | 2008154642 | 12/2008 |
| WO | 2009012283 | 1/2009 |
| WO | 2009086277 | 7/2009 |
| WO | 2009103778 | 8/2009 |
| WO | 2009140128 | 11/2009 |
| WO | 2010017047 | 2/2010 |
| WO | 2010084425 | 7/2010 |
| WO | 2010088000 | 8/2010 |
| WO | 2011022439 | 2/2011 |
| WO | 2011050245 | 4/2011 |
| WO | 2011090738 | 7/2011 |
| WO | 2011156655 | 12/2011 |
| WO | WO 2012017021 A2 * | 2/2012 ......... B01D 15/3804 |
| WO | 2012026765 | 3/2012 |
| WO | 2013030802 | 3/2013 |

OTHER PUBLICATIONS

Chen et. al., Cancer Letters, 2006, Elsevier, vol. 233, pp. 328-337.*
Drummond et. al., British Journal of Haematology, 2003, Blackwell Publishing, vol. 120. pp. 911-913.*
Van der Ploeg et. al., Lancet, 2008, Little, Brown & Co., vol. 372, pp. 1342-1353.*
Schermuly et. al., The Journal of Clinical Investigation, 2005, American Society for Clinical Investigation, vol. 115, pp. 2811-2821.*
[No Author Listed] CAS STN Abstract 2008, RN 1007820-93-0.
Morphy, Selectively nonselective kinase inhibition: striking the right balance. J Med Chem. Feb. 25, 2010;53(4):1413-37.
Kim et al., Design and synthesis of imidazopyridine analogues as inhibitors of phosphoinositide 3-kinase signaling and angiogenesis. J Med Chem. Apr. 14, 2011;54(7):2455-66.

* cited by examiner

BICYCLIC HETEROCYCLE DERIVATIVES FOR THE TREATMENT OF PULMONARY ARTERIAL HYPERTENSION

CROSS-REFERENCE TO RELATED APPLICATIONS

This application is a divisional application of U.S. Ser. No. 13/599,267, filed Aug. 30, 2012, which claims the benefit of priority under 35 U.S.C. §119(e) to U.S. Provisional Patent Application No. 61/530,049, filed Sep. 1, 2011 and U.S. Provisional Patent Application No. 61/680,119, filed Aug. 6, 2012, the disclosures of which are incorporated herein by reference in their entirety and for all purposes.

FIELD OF THE INVENTION

The present invention relates to bicyclic heterocycle derivatives, their preparation, their use as pharmaceuticals and pharmaceutical compositions containing them. More particularly the present invention relates to their use in inhibiting PDGF receptor mediated biological activity.

BACKGROUND

Protein kinases (PK) are a large set of structurally related phosphoryl transferases having highly conserved structures and catalytic functions. Protein kinases are enzymatic components of the signal transduction pathways which catalyze the transfer of the terminal phosphate from ATP to the hydroxy group of tyrosine, serine and/or threonine residues of proteins, and are therefore categorized into families by the substrates they phosphorylate: Protein Tyrosine Kinases (PTK), and Protein Serine/Threonine Kinases.

Protein kinases play a critical role in the control of cell growth and differentiation and are responsible for the control of a wide variety of cellular signal transduction processes, wherein protein kinases are key mediators of cellular signals leading to the production of growth factors and cytokines. The overexpression or inappropriate expression of normal or mutant protein kinases plays a significant role in the development of many diseases and disorders including, central nervous system disorders such as Alzheimer's, inflammatory disorders such as arthritis, bone diseases such as osteoporosis, metabolic disorders such as diabetes, blood vessel proliferative disorders such as angiogenesis, autoimmune diseases such as rheumatoid arthritis, ocular diseases, cardiovascular disease, atherosclerosis, cancer, thrombosis, psoriasis, restenosis, schizophrenia, pain sensation, transplant rejection and infectious diseases such as viral, and fungal infections.

The agents of the invention act as inhibitors of PDGFR kinase, c-Kit kinase and related receptor and non-receptor tyrosine kinases. PDGFR is activated by binding of the growth factor PDGF to the extracellular portion of the receptor. Upon activation PDGFR phosphorylates many substrate proteins and controls a wide variety of cellular functions including proliferation and migration. PDGFR mediates these effects on multiple cell types including those of the mesenchymal lineage, fibroblasts, vascular smooth muscles cells and pericytes.

PDGFR kinase inhibition is expected to be a useful target for the treatment of various cardiovascular, pulmonary, tissue remodelling and hypertrophic disorders, many cancers and other indications in which PDGF driven functional responses contribute to pathology, including PAH. PDGFR, PDGFR ligands and activated, phosphorylated PDGFR is found in the proliferating smooth muscle cells that comprise the lesions in the pulmonary vasculature of PAH patients and animal models of PAH. Furthermore, the tyrosine kinase inhibitor Gleevec® has been shown to be efficacious in the treatment of PAH clinically and in pre-clinical PAH models. Other targets inhibited by the agents of the invention may contribute to the efficacy of the agents in PAH, asthma and other indications. For example, c-kit inhibition contributes to the depletion of mast cells and is beneficial in the treatment of preclinical models of asthma.

SUMMARY OF THE INVENTION

In a first aspect of the invention, Embodiment 1, we provide a compound of formula (I);

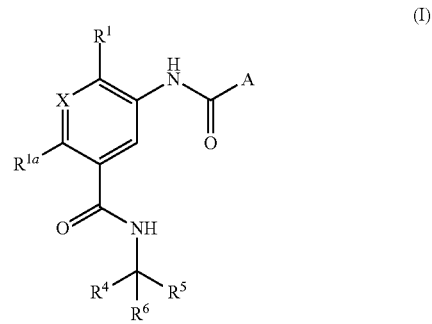

or a pharmaceutically acceptable salt thereof, wherein,
A is

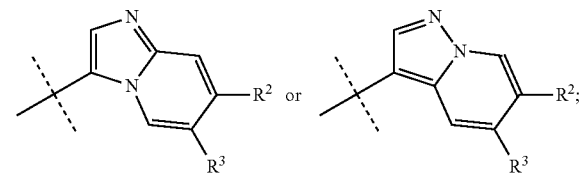

$R^1$ is $C_1$-$C_4$ alkyl; $C_1$-$C_4$ alkoxy optionally substituted by one or more halogen atoms; CN; or halogen;
$R^{1a}$ is H, halogen, $C_1$-$C_4$ alkyl or $C_1$-$C_4$ haloalkyl;
X is N or CH;
$R^2$ is H; $C_1$-$C_8$ alkyl optionally substituted by one or more OH, —$NR^9R^{11}$ or $C_1$-$C_4$ alkoxy; $C_1$-$C_8$ haloalkyl; $C_2$-$C_8$ alkynyl substituted by one or more halogen, OH, —$NR^9R^{11}$ or $C_1$-$C_4$ alkoxy; $C_3$-$C_{10}$ cycloalkyl; —($C_1$-$C_4$ alkyl)-$C_3$-$C_8$ cycloalkyl; $C_1$-$C_8$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-C(O)$NR^9R^{11}$; —($C_0$-$C_4$ alkyl)-$C_6$-$C_{14}$ aryl; or —($C_0$-$C_4$ alkyl)-3 to 14 membered heterocyclyl; wherein the cycloalkyl, —($C_0$-$C_4$ alkyl)-$C_6$-$C_{14}$ aryl and —($C_0$-$C_4$ alkyl)-3 to 14 heterocyclyl are each optionally substituted by one or more $Z^a$ substituents;
$R^3$ is H; $C_1$-$C_8$ alkyl optionally substituted by one or more OH, —$NR^9R^{11}$ or $C_1$-$C_4$ alkoxy; $C_1$-$C_8$ haloalkyl; $C_2$-$C_8$ alkynyl substituted by one or more halogen, OH, —$NR^9R^{11}$, or $C_1$-$C_4$ alkoxy; $C_3$-$C_{10}$ cycloalkyl; —($C_1$-$C_4$ alkyl)-$C_3$-$C_8$ cycloalkyl; $C_1$-$C_8$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-C(O)NR$^9$R$^{11}$; —(C$_0$-C$_4$ alkyl)-C$_6$-C$_{14}$ aryl; or —(C$_0$-C$_4$ alkyl)-3 to 14 membered heterocyclyl; wherein the cycloalkyl, —(C$_0$-C$_4$ alkyl)-C$_6$-C$_{14}$ aryl and —(C$_0$-C$_4$ alkyl)-3 to 14 heterocyclyl are each optionally substituted by one or more Z$^a$ substituents;

each Z$^a$ is independently OH; —(C$_0$-C$_4$ alkyl)-C$_6$ aryl; —O—C$_6$ aryl; C$_1$-C$_4$ alkyl optionally substituted by one or more OH, CN or —NR$^{19a}$R$^{21a}$; C$_1$-C$_4$ haloalkyl; C$_1$-C$_4$ alkoxy optionally substituted by one or more OH, —CO$_2$R$^{19a}$, —NR$^{19a}$R$^{21a}$ or C$_1$-C$_4$ alkoxy; —NR$^{18a}$C(O)R$^{21a}$; —C(O)NR$^{19a}$R$^{21a}$; —NR$^{18a}$C(O)NR$^{19a}$R$^{21a}$; —NR$^{19a}$R$^{21a}$; —(C$_0$-C$_4$ alkyl)-C(O)OR$^{18a}$; —(C$_0$-C$_4$ alkyl)-C(O)R$^{19a}$; oxo; CN; NO$_2$; halogen or —(C$_0$-C$_4$ alkyl)-4 to 6 membered heterocyclyl; wherein the aryl and heterocyclyl are each optionally substituted by halogen, C$_1$-C$_4$ alkyl, C$_1$-C$_4$ haloalkyl or C$_1$-C$_4$ alkoxy optionally substituted by one or more halogens;

R$^4$ is H, C$_1$-C$_4$ alkyl or C$_1$-C$_4$ haloalkyl;

R$^5$ is H, C$_1$-C$_4$ alkyl or C$_1$-C$_4$ haloalkyl;

R$^6$ is selected from C$_1$-C$_8$ alkyl optionally substituted by one or more C$_1$-C$_4$ alkoxy; C$_1$-C$_8$ haloalkyl; —(C$_0$-C$_4$alkyl)-C$_3$-C$_8$cycloalkyl; C$_1$-C$_8$alkoxy optionally substituted by one or more halogen atoms; —NR$^{19}$R$^{21}$; —(C$_0$-C$_4$ alkyl)-C$_8$-C$_{14}$aryl; —(C$_0$-C$_4$ alkyl)-3 to 14 membered heterocyclyl; and —(C$_0$-C$_4$ alkyl)-CO$_2$R$^{16}$; wherein the —(C$_0$-C$_4$alkyl)-C$_3$-C$_8$cycloalkyl, —(C$_0$-C$_4$ alkyl)-C$_8$-C$_{14}$aryl and —(C$_0$-C$_4$ alkyl)-3 to 14 heterocyclyl are each optionally substituted by one or more Z substituents;

each Z is independently selected from OH; (C$_0$-C$_4$ alkyl)-C$_6$ aryl; O—C$_6$ aryl; C$_1$-C$_6$ alkyl optionally substituted by one or more OH, CN or —NR$^{19}$R$^{21}$; C$_1$-C$_6$ haloalkyl; C$_1$-C$_6$ alkoxy optionally substituted by one or more OH, —CO$_2$R$^{18}$, —NR$^{19}$R$^{21}$ or C$_1$-C$_4$ alkoxy; —NR$^{18}$C(O)R$^{19}$; —C(O)NR$^{19}$R$^{21}$; —NR$^{18}$C(O)NR$^{19}$R$^{21}$; —NR$^{19}$R$^{21}$; (C$_0$-C$_4$ alkyl)-C(O)OR$^{19}$; (C$_0$-C$_4$ alkyl)-C(O)R$^{19}$; oxo; CN; NO$_2$; halogen and (C$_0$-C$_4$ alkyl)-4 to 6 membered heterocyclyl; and wherein the aryl and heterocyclyl are each optionally substituted by one or more halogen, C$_1$-C$_6$ alkyl, C$_1$-C$_6$ haloalkyl and C$_1$-C$_6$ alkoxy optionally substituted by one or more halogens;

R$^9$ and R$^{11}$ are each independently selected from H; C$_1$-C$_8$ alkyl optionally substituted by one or more C$_1$-C$_4$ alkoxy or OH; C$_1$-C$_6$ haloalkyl; —(C$_0$-C$_4$alkyl)-C$_3$-C$_6$cycloalkyl; (C$_0$-C$_4$ alkyl)-C$_6$-C$_{14}$aryl optionally substituted by one or more groups selected from C$_1$-C$_8$ alkyl, C$_1$-C$_8$ alkoxy and halogen; and (C$_0$-C$_4$ alkyl)-3- to 14-membered heterocyclyl optionally substituted by one or more groups selected from halogen, oxo, C$_1$-C$_6$ alkyl and C(O)C$_1$-C$_6$ alkyl; or R$^9$ and R$^{11}$ together with the nitrogen atom to which they are attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl; 5- to 10-membered heterocyclyl; C$_1$-C$_6$ alkyl; C$_1$-C$_6$ haloalkyl; C$_1$-C$_6$ alkoxy optionally substituted by one or more OH or C$_1$-C$_4$ alkoxy; and C(O)OC$_1$-C$_6$alkyl; wherein the phenyl and heterocyclyl substituent groups are themselves optionally substituted by C$_1$-C$_6$ alkyl, C$_1$-C$_6$ haloalkyl or C$_1$-C$_6$ alkoxy;

R$^{15}$ is selected from H; C$_1$-C$_8$ alkyl; C$_1$-C$_8$ haloalkyl; C$_3$-C$_{10}$ cycloalkyl; (—C$_1$-C$_4$alkyl)-C$_3$-C$_8$ cycloalkyl; —(C$_0$-C$_4$ alkyl)-C$_6$-C$_{14}$aryl and —(C$_0$-C$_4$ alkyl)-3 to 14 membered heterocyclyl group; wherein the cycloalkyl, aryl and heterocyclyl groups are each optionally substituted by one or more Z substituents;

R$^{18a}$ is independently H or C$_1$-C$_6$ alkyl;

R$^{19a}$ and R$^{21a}$ are each independently H; C$_1$-C$_6$ alkyl optionally substituted by one or more C$_1$-C$_4$ alkoxy or OH; C$_1$-C$_6$ haloalkyl; —(C$_0$-C$_4$alkyl)-C$_3$-C$_6$cycloalkyl; (C$_0$-C$_4$ alkyl)-C$_6$-C$_{14}$aryl optionally substituted by one or more groups selected from C$_1$-C$_6$ alkyl, C$_1$-C$_6$ alkoxy and halogen; or (C$_0$-C$_4$ alkyl)-3- to 14-membered heterocyclyl optionally substituted by one or more groups selected from halogen, oxo, C$_1$-C$_6$ alkyl and C(O)C$_1$-C$_6$ alkyl; or R$^{19a}$ and R$^{21a}$ together with the nitrogen atom to which they attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl; 5- to 10-membered heterocyclyl; C$_1$-C$_6$ alkyl; C$_1$-C$_6$ haloalkyl; C$_1$-C$_6$ alkoxy optionally substituted by one or more OH or C$_1$-C$_4$ alkoxy; and C(O)OC$_1$-C$_6$alkyl; wherein the phenyl and heterocyclyl substituent groups are themselves optionally substituted by C$_1$-C$_6$ alkyl, C$_1$-C$_6$ haloalkyl or C$_1$-C$_6$ alkoxy;

R$^{18}$ is independently H or C$_1$-C$_6$ alkyl;

R$^{19}$ and R$^{21}$ are each independently H; C$_1$-C$_6$ alkyl optionally substituted by one or more C$_1$-C$_4$ alkoxy or OH; C$_1$-C$_6$ haloalkyl; —(C$_0$-C$_4$alkyl)-C$_3$-C$_6$cycloalkyl; (C$_0$-C$_4$ alkyl)-C$_6$-C$_{14}$aryl optionally substituted by one or more groups selected from C$_1$-C$_6$ alkyl, C$_1$-C$_6$ alkoxy and halogen; or (C$_0$-C$_4$ alkyl)-3- to 14-membered heterocyclyl, optionally substituted by one or more groups selected from halogen, oxo, C$_1$-C$_6$ alkyl and C(O)C$_1$-C$_6$ alkyl; or R$^{19}$ and R$^{21}$ together with the nitrogen atom to which they attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl; 5- to 10-membered heterocyclyl; C$_1$-C$_6$ alkyl; C$_1$-C$_6$ haloalkyl; C$_1$-C$_6$ alkoxy optionally substituted by one or more OH or C$_1$-C$_4$ alkoxy and C(O)OC$_1$-C$_6$alkyl; wherein the phenyl and heterocyclyl substituent groups are themselves optionally substituted by a substituent selected from C$_1$-C$_6$ alkyl, C$_1$-C$_6$ haloalkyl and C$_1$-C$_6$ alkoxy.

DEFINITIONS

For purposes of interpreting this specification, the following definitions will apply and whenever appropriate, terms used in the singular will also include the plural and vice versa.

As used herein, the term "alkyl" refers to a fully saturated branched or unbranched hydrocarbon moiety having up to 20 carbon atoms. Unless otherwise provided, alkyl refers to hydrocarbon moieties having 1 to 8 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, or n-octyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Typically, alkoxy groups have about 1-6, more preferably about 1-4 carbons.

As used herein, the term "haloalkyl" refers to an alkyl as defined herein that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 5, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms.

As used herein, the term "cycloalkyl" refers to saturated or unsaturated monocyclic, bicyclic or tricyclic hydrocarbon groups of 3-10 carbon atoms. Unless otherwise provided, cycloalkyl refers to cyclic hydrocarbon groups having between 3 and 10 ring carbon atoms or between 3 and 8 ring carbon atoms. Exemplary monocyclic hydrocarbon groups include, but are not limited to, cyclopropyl, cyclobutyl, cyclopentyl, cyclopentenyl, cyclohexyl or cyclohexenyl. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl.

The term "$C_{2-8}$ alkynyl" as used herein refers to a linear or branched saturated hydrocarbon group containing from 2 to 8 carbon atoms that contains at least one carbon to carbon triple bond. Examples of such groups include ethynyl, propynyl, butynyl and pentynyl.

The term "aryl" refers to an aromatic hydrocarbon group having 6-14 carbon atoms in the ring portion. Typically, aryl is monocyclic or bicyclic aryl having 6-14 carbon atoms and includes one aromatic ring fused to one non-aromatic hydrocarbon ring. Non-limiting examples include phenyl, indane, naphthyl or tetrahydronaphthyl.

As used herein, the term "aryloxy" refers to both an —O-aryl and an —O-heteroaryl group, wherein aryl and heteroaryl are defined herein.

As used herein, the term "4- to 8-Membered heterocyclyl", "5- to 6-membered heterocyclyl", "3- to 10-membered heterocyclyl", "3- to 14-membered heterocyclyl", "4- to 14-membered heterocyclyl" and "5- to 14-membered heterocyclyl", refers, respectively, to 4- to 8-membered, 5- to 6-membered, 3- to 10-membered, 3- to 14-membered, 4- to 14-membered and 5- to 14-membered heterocyclic rings containing at least one ring heteroatom selected from the group consisting of nitrogen, oxygen and sulphur, which may be saturated, partially saturated or unsaturated (aromatic). The heterocyclyl includes single ring groups, fused ring groups and bridged groups. Examples of such heterocyclyl include, but are not limited to, furan, pyrrole, pyrrolidine, pyrazole, imidazole, triazole, isotriazole, tetrazole, thiadiazole, isothiazole, oxadiazole, pyridine, piperidine, pyrazine, oxazole, isoxazole, pyrazine, pyridazine, pyrimidine, piperazine, pyrrolidine, pyrrolidinone, morpholine, triazine, oxazine, tetrahyrofuran, tetrahydrothiophene, tetrahydrothiopyran, tetrahydropyran, 1,4-dioxane, 1,4-oxathiane, indazole, quinoline, indazole, indole, 8-aza-bicyclo[3.2.1]octane, 2,3-dihydrobenzofuran or thiazole.

"Heteroaryl" is a subset of heterocyclyl, wherein "heteroaryl" are completely unsaturated (aromatic). Examples of such groups are pyridine and pyrazine.

As used herein, the term "halogen" or "halo" refers to fluoro, chloro, bromo, and iodo.

Various embodiments of the invention are described herein. It will be recognized that features specified in each embodiment may be combined with other specified features to provide further embodiments.

Embodiment 2

A compound of formula (I);

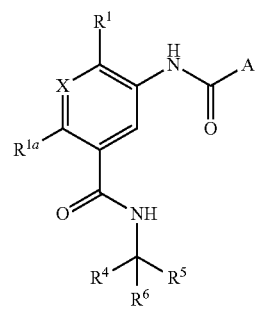

or a pharmaceutically acceptable salt thereof,
wherein,
A is

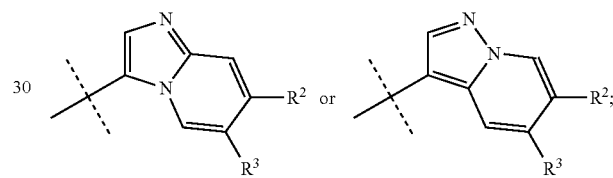

$R^1$ is $C_1$-$C_4$ alkyl; $C_1$-$C_4$ alkoxy optionally substituted by one or more halogen atoms; CN; or halogen;
$R^{1a}$ is H, halogen, $C_1$-$C_4$ alkyl or $C_1$-$C_4$ haloalkyl;
X is N or CH;
$R^2$ is H; $C_1$-$C_8$ alkyl optionally substituted by one or more OH, —$NR^9R^{11}$ or $C_1$-$C_4$ alkoxy; $C_1$-$C_8$ haloalkyl; $C_2$-$C_{58}$alkynyl substituted by one or more halogen, OH, —$NR^9R^{11}$ or $C_1$-$C_4$ alkoxy; $C_3$-$C_{10}$ cycloalkyl; —($C_1$-$C_4$ alkyl)-$C_3$-$C_8$ cycloalkyl; $C_1$-$C_8$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-C(O)$NR^9R^{11}$; —($C_0$-$C_4$ alkyl)-$C_6$-$C_{14}$ aryl; or —($C_0$-$C_4$ alkyl)-3 to 14 membered heterocyclyl; wherein the cycloalkyl, —($C_0$-$C_4$ alkyl)-$C_6$-$C_{14}$ aryl and —($C_0$-$C_4$ alkyl)-3 to 14 heterocyclyl are each optionally substituted by one or more $Z^a$ substituents;
$R^3$ is H; $C_1$-$C_8$ alkyl optionally substituted by one or more OH, —$NR^9R^{11}$ or $C_1$-$C_4$ alkoxy; $C_1$-$C_8$ haloalkyl; $C_2$-$C_8$ alkynyl substituted by one or more halogen, OH, —$NR^9R^{11}$, or $C_1$-$C_4$ alkoxy; $C_3$-$C_{10}$ cycloalkyl; —($C_1$-$C_4$ alkyl)-$C_3$-$C_8$ cycloalkyl; $C_1$-$C_8$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-C(O)$NR^9R^{11}$; —($C_0$-$C_4$ alkyl)-$C_6$-$C_{14}$ aryl; or —($C_0$-$C_4$ alkyl)-3 to 14 membered heterocyclyl; wherein the cycloalkyl, —($C_0$-$C_4$ alkyl)-$C_6$-$C_{14}$ aryl and —($C_0$-$C_4$ alkyl)-3 to 14 heterocyclyl are each optionally substituted by one or more $Z^a$ substituents;
each $Z^a$ is independently OH; ($C_0$-$C_4$ alkyl)-$C_6$ aryl; O—$C_6$ aryl; $C_1$-$C_4$ alkyl optionally substituted by one or more OH, CN or —$NR^{19a}R^{21a}$; $C_4$ haloalkyl; $C_1$-$C_4$ alkoxy optionally substituted by one or more OH, —$CO_2R^{19a}$, —$NR^{19a}R^{21a}$ or $C_1$-$C_4$ alkoxy; —NR$^{18a}$C(O)R$^{21a}$; —C(O)NR$^{19a}$R$^{21a}$; —NR$^{18a}$C(O)NR$^{19a}$R$^{21a}$; —NR$^{19a}$R$^{21a}$; ($C_0$-$C_4$ alkyl)-C(O)OR$^{18a}$; —($C_0$-$C_4$ alkyl)-C(O)R$^{19a}$; oxo; CN; NO$_2$; halogen; —($C_0$-$C_4$ alkyl)-4 to 6 membered heterocyclyl; or —O-(4 to 6 membered heterocyclyl); wherein the ($C_0$-$C_4$ alkyl)-$C_6$ aryl, O—$C_6$ aryl, —($C_0$-$C_4$ alkyl)-4 to 6 membered heterocyclyl and —O-(4 to 6 membered heterocyclyl) are each optionally substituted by OH, halogen, $C_1$-$C_4$ alkyl, $C_1$-$C_4$ haloalkyl or $C_1$-$C_4$ alkoxy optionally substituted by one or more halogens;

$R^4$ is H;

$R^5$ is H, $C_1$-$C_4$ alkyl or $C_1$-$C_4$ haloalkyl;

$R^6$ is selected from $C_1$-$C_8$ alkyl optionally substituted by one or more $C_1$-$C_4$ alkoxy or —NR$^{19}$R$^{21}$; $C_1$-$C_8$ haloalkyl; —($C_0$-$C_4$alkyl)-$C_3$-$C_8$cycloalkyl; $C_1$-$C_8$alkoxy optionally substituted by one or more halogen atoms; —NR$^{19}$R$^{21}$; —($C_0$-$C_4$ alkyl)-$C_6$-$C_{14}$aryl; and —($C_0$-$C_4$ alkyl)-3 to 14 membered heterocyclyl; wherein the —($C_0$-$C_4$alkyl)-$C_3$-$C_8$cycloalkyl, —($C_0$-$C_4$ alkyl)-$C_6$-$C_{14}$aryl and —($C_0$-$C_4$ alkyl)-3 to 14 heterocyclyl are each optionally substituted by one or more Z substituents;

each Z is independently selected from ($C_0$-$C_4$ alkyl)-$C_6$ aryl; O—$C_6$ aryl; $C_1$-$C_6$ alkyl optionally substituted by one or more $C_1$-$C_6$ alkoxy, CN or —NR$^{19}$R$^{21}$; $C_1$-$C_6$ haloalkyl; $C_1$-$C_6$ alkoxy optionally substituted by one or more —NR$^{19}$R$^{21}$ or $C_1$-$C_4$ alkoxy; —NR$^{19}$R$^{21}$; ($C_0$-$C_4$ alkyl)-C(O)R$^{19}$; CN; halogen and ($C_0$-$C_4$ alkyl)-4 to 6 membered heterocyclyl; and wherein the aryl and heterocyclyl are each optionally substituted by one or more halogen, $C_1$-$C_6$ alkyl, $C_1$-$C_6$ haloalkyl and $C_1$-$C_6$ alkoxy optionally substituted by one or more halogens;

$R^9$ and $R^{11}$ are each independently selected from H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$ cycloalkyl; ($C_0$-$C_4$ alkyl)-$C_6$-$C_{14}$aryl optionally substituted by one or more groups selected from $C_1$-$C_6$ alkyl, $C_1$-$C_6$ alkoxy and halogen; and ($C_0$-$C_4$ alkyl)-3- to 14-membered heterocyclyl optionally substituted by one or more groups selected from halogen, oxo, $C_1$-$C_6$ alkyl and C(O)$C_1$-$C_6$ alkyl; or $R^9$ and $R^{11}$ together with the nitrogen atom to which they are attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl, 5- to 10-membered heterocyclyl; $C_1$-$C_6$ alkyl; $C_1$-$C_6$ haloalkyl; $C_1$-$C_6$ alkoxy optionally substituted by one or more OH or $C_1$-$C_4$ alkoxy; and C(O)OC$_1$-$C_6$alkyl; wherein the phenyl and heterocyclyl substituent groups are themselves optionally substituted by $C_1$-$C_6$ alkyl, $C_1$-$C_6$ haloalkyl or $C_1$-$C_6$ alkoxy;

$R^{15}$ is selected from H; $C_1$-$C_8$ alkyl; $C_1$-$C_8$ haloalkyl; $C_3$-$C_{10}$ cycloalkyl; (—$C_1$-$C_4$alkyl)-$C_3$-$C_8$ cycloalkyl; —($C_0$-$C_4$ alkyl)-$C_6$-$C_{14}$aryl and —($C_0$-$C_4$ alkyl)-3 to 14 membered heterocyclyl group; wherein the $C_3$-$C_{10}$ cycloalkyl, (—$C_1$-$C_4$alkyl)-$C_3$-$C_8$ cycloalkyl, —($C_0$-$C_4$ alkyl)-$C_6$-$C_{14}$aryl and —($C_0$-$C_4$ alkyl)-3 to 14 membered heterocyclyl groups are each optionally substituted by one or more Z substituents;

$R^{18a}$ is independently H or $C_1$-$C_6$ alkyl;

$R^{19a}$ and $R^{21a}$ are each independently H; $C_1$-$C_6$ alkyl optionally substituted by one or more $C_1$-$C_4$ alkoxy, —NR$^{22}$R$^{23'}$, or OH; $C_1$-$C_6$ haloalkyl; —($C_0$-$C_4$alkyl)-$C_3$-$C_6$cycloalkyl; —($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-3- to 14-membered heterocyclyl optionally substituted by one or more groups selected from halogen, oxo, $C_1$-$C_6$ alkyl and C(O)$C_1$-$C_6$ alkyl; or $R^{19a}$ and $R^{21a}$ together with the nitrogen atom to which they attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl; 5- to 10-membered heterocyclyl; $C_1$-$C_6$ alkyl; $C_1$-$C_6$ haloalkyl; $C_1$-$C_6$ alkoxy optionally substituted by one or more OH or $C_1$-$C_4$ alkoxy; and C(O)OC$_1$-$C_6$alkyl; wherein the phenyl and heterocyclyl substituent groups are themselves optionally substituted by $C_1$-$C_6$ alkyl, $C_1$-$C_6$ haloalkyl or $C_1$-$C_6$ alkoxy;

$R^{18}$ is independently H or $C_1$-$C_6$ alkyl;

$R^{19}$ and $R^{21}$ are each independently $C_1$-$C_6$ alkyl optionally substituted by one or more $C_1$-$C_4$ alkoxy; $C_1$-$C_6$ haloalkyl; —($C_0$-$C_1$alkyl)-$C_3$-$C_6$cycloalkyl; —($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-3- to 14-membered heterocyclyl, optionally substituted by one or more groups selected from halogen, $C_1$-$C_6$ alkyl and —C(O)$C_1$-$C_6$ alkyl; or $R^{19}$ and $R^{21}$ together with the nitrogen atom to which they attached form a 5- to 10-membered heterocyclyl, which heterocyclyl includes 0 to 3 further heteroatoms selected from N, O and S, the heterocyclyl being optionally substituted by one or more substituents selected from halogen; phenyl; 5- to 10-membered heterocyclyl; $C_1$-$C_6$ alkyl; $C_1$-$C_6$ haloalkyl; $C_1$-$C_6$ alkoxy optionally substituted by one or more $C_1$-$C_4$ alkoxy and C(O)OC$_1$-$C_6$alkyl; wherein the phenyl and heterocyclyl substituent groups are themselves optionally substituted by a substituent selected from $C_1$-$C_6$ alkyl, $C_1$-$C_6$ haloalkyl and $C_1$-$C_6$ alkoxy; and $R^{22}$ and $R^{23}$ are each independently H or $C_1$-$C_6$ alkyl.

Embodiment 3

A compound of formula (I), according to Embodiment 1 or Embodiment 2, wherein $R^1$ is $C_1$-$C_4$ alkyl, $C_1$-$C_4$ alkoxy, CN or halogen.

Embodiment 4

A compound of formula (I), according to any preceding Embodiment, wherein $R^1$ is $C_1$-$C_4$ alkyl or halogen.

Embodiment 5

A compound of formula (I), according to any preceding Embodiment, wherein $R^1$ is methyl or halogen.

Embodiment 6

A compound of formula (I), according to any preceding Embodiment, wherein $R^1$ is methyl or F.

Embodiment 7

A compound of formula (I), according to any preceding Embodiment, wherein $R^{1a}$ is H, methyl or F; particularly $R^{1a}$ is H.

Embodiment 8

A compound of formula (I), according to any preceding Embodiment, wherein X is N.

Embodiment 9

A compound of formula (I), according to any one of Embodiments 1 to 7, wherein X is CH.

Embodiment 10

A compound of formula (I), according to any preceding Embodiment, wherein $R^2$ is H; $C_1$-$C_6$ alkyl optionally substituted by one or more OH, —$NR^9R^{11}$ or $C_1$-$C_4$ alkoxy; $C_1$-$C_6$ haloalkyl; $C_2$-$C_6$ alkynyl substituted by one or more halogen, OH, —$NR^9R^{11}$ or $C_1$-$C_4$ alkoxy; $C_3$-$C_6$ cycloalkyl; —($C_1$-$C_4$ alkyl)-$C_3$-$C_6$ cycloalkyl; $C_1$-$C_6$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-$C(O)NR^{19}R^{21}$; —($C_0$-$C_4$ alkyl)-$C_6$-$C_{14}$aryl; or —($C_0$-$C_4$ alkyl)-3 to 14 membered heterocyclyl; wherein the $C_3$-$C_6$cycloalkyl, —($C_0$-$C_4$ alkyl)-$C_6$-$C_{14}$aryl and —($C_0$-$C_4$ alkyl)-3 to 14 heterocyclyl are each optionally substituted by one or more $Z^a$ substituents.

Embodiment 11

A compound of formula (I), according to any preceding Embodiment, wherein $R^2$ is H; $C_1$-$C_4$ alkyl optionally substituted by one or more OH, —$NR^9R^{11}$ or $C_1$-$C_4$ alkoxy; $C_1$-$C_4$ haloalkyl; $C_2$-$C_6$ alkynyl substituted by one or more halogen, OH, —$NR^9R^{11}$, or $C_1$-$C_4$ alkoxy; $C_3$-$C_6$ cycloalkyl; —($C_1$-$C_4$ alkyl)-$C_3$-$C_6$ cycloalkyl; $C_1$-$C_6$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-$C(O)NR^{19}R^{11}$; —($C_0$-$C_4$ alkyl)-$C_6$-$C_{14}$aryl; or —($C_0$-$C_4$ alkyl)-3 to 14 membered heterocyclyl; wherein the $C_3$-$C_6$cycloalkyl, —($C_0$-$C_4$ alkyl)-$C_6$-$C_{14}$aryl and —($C_0$-$C_4$ alkyl)-3 to 14 heterocyclyl are each optionally substituted by one or more $Z^a$ substituents.

Embodiment 12

A compound of formula (I), according to any preceding Embodiment, wherein $R^2$ is H; $C_1$-$C_4$ alkyl optionally substituted by one or more OH or —$NR^9R^{11}$; $C_1$-$C_4$ haloalkyl; $C_1$-$C_4$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$C(O)NR^9R^{11}$; phenyl; or —($C_0$-$C_4$ alkyl)-5 to 6 membered heterocyclyl; wherein the phenyl and —($C_0$-$C_4$ alkyl)-5 to 6 heterocyclyl are each optionally substituted by one or more $Z^a$ substituents.

Embodiment 13

A compound of formula (I), according to any preceding Embodiment, wherein $R^2$ is H; $C_1$-$C_4$ alkyl optionally substituted by one or more OH or —$NH_2$; $C_1$-$C_4$ alkoxy optionally substituted by one or more —$NR^9R^{11}$ or OH; F; Br; —($C_1$-$C_2$ alkyl)-$NR^9R^{11}$; —$C(O)NR^9R^{11}$; phenyl; or —($C_0$-$C_4$ alkyl)-5 to 6 membered heterocyclyl; wherein the phenyl and —($C_0$-$C_4$ alkyl)-5 to 6 heterocyclyl are each optionally substituted by one or more $Z^a$ substituents.

Embodiment 14

A compound of formula (I), according to any preceding Embodiment, wherein $R^2$ is H; $C_1$-$C_4$ alkyl optionally substituted by one or more OH or —$NH_2$; $C_1$-$C_4$ alkoxy optionally substituted by —$NR^9R^{11}$; F; Br; —($C_1$-$C_2$ alkyl)-$NR^9R^{11}$; —$C(O)NR^9R^{11}$; phenyl; or —($C_0$-$C_4$ alkyl)-5 to 6 membered heterocyclyl; wherein the phenyl and —($C_0$-$C_4$ alkyl)-5 to 6 heterocyclyl are each optionally substituted by one or more $Z^a$ substituents.

Embodiment 15

A compound of formula (I), according to any preceding Embodiment, wherein $R^2$ is H; $C_1$-$C_4$ alkyl optionally substituted by one or more OH; $C_1$-$C_4$ alkoxy optionally substituted by —$NR^9R^{11}$; F; Br; —$C(O)NHR^{11}$; phenyl; or —($C_0$-$C_4$ alkyl)-5 to 6 membered heterocyclyl; wherein the phenyl and —($C_0$-$C_4$ alkyl)-5 to 6 membered heterocyclyl are each optionally substituted by one or more $Z^a$ substituents.

Embodiment 16

A compound of formula (I), according to any preceding Embodiment, wherein $R^2$ is phenyl or —($C_0$-$C_4$ alkyl)-5 to 6 membered heterocyclyl, each optionally substituted by one, two or three $Z^a$ substituents.

Embodiment 17

A compound of formula (I), according to any preceding Embodiment, wherein $R^2$ is phenyl or 5- or 6-membered heterocyclyl, each optionally substituted by one, two or three $Z^a$ substituents.

Embodiment 18

A compound of formula (I), according to any one of Embodiments 1 to 15, wherein $R^2$ is H, F, Br,

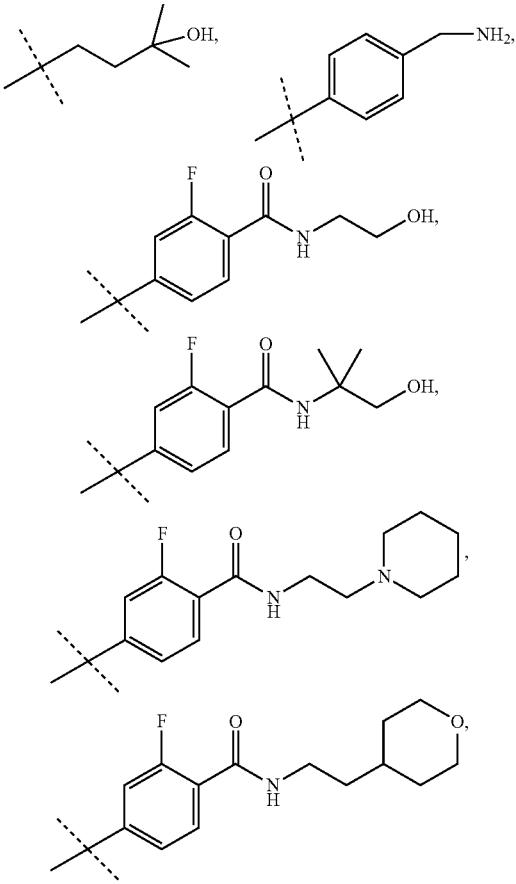

-continued

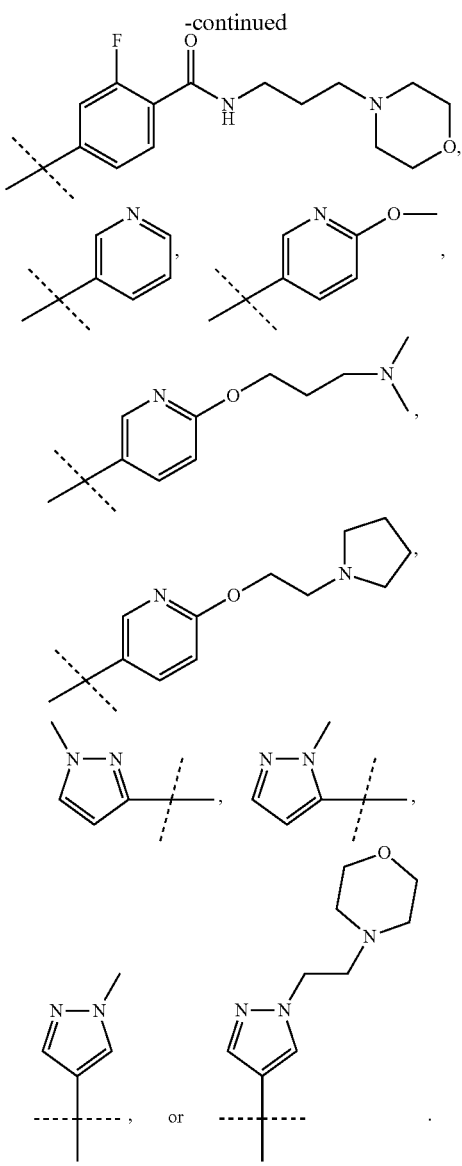

Embodiment 19

A compound of formula (I), according to any preceding Embodiment, wherein $R^3$ is H; $C_1$-$C_4$ alkyl optionally substituted by one or more OH, —$NR^9R^{11}$ or $C_1$-$C_4$alkoxy; $C_1$-$C_4$ haloalkyl; $C_2$-$C_6$ alkynyl substituted by one or more halogen, OH, —$NR^9R^{11}$ or $C_1$-$C_4$alkoxy; $C_3$-$C_6$ cycloalkyl; —($C_1$-$C_4$ alkyl)-$C_3$-$C_8$ cycloalkyl; —$C_1$-$C_4$alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-$C(O)NR^9R^{11}$; —($C_0$-$C_4$ alkyl)-$C_6$aryl; or —($C_0$-$C_4$ alkyl)-5 to 6 membered heterocyclyl; wherein the $C_3$-$C_6$ cycloalkyl, —($C_0$-$C_4$ alkyl)-$C_6$aryl and —($C_0$-$C_4$ alkyl)-5 to 6 heterocyclyl are each optionally substituted by one or more $Z^a$ substituents.

Embodiment 20

A compound of formula (I), according to any preceding Embodiment, wherein $R^3$ is H; $C_1$-$C_4$ alkyl optionally substituted by one or more OH or —$NR^9R^{11}$; $C_1$-$C_4$ haloalkyl; $C_3$-$C_6$ cycloalkyl; $C_1$-$C_4$alkoxy optionally substituted by one or more halogen or —$NR^9R^{11}$; OH; CN; halogen; —($C_0$-$C_4$ alkyl)-$C(O)NR^{19}R^{21}$; phenyl; or -5 to 6 membered heterocyclyl, wherein the $C_3$-$C_6$ cycloalkyl, phenyl and 5 to 6 heterocyclyl are each optionally substituted by one or more $Z^a$ substituents.

Embodiment 21

A compound of formula (I), according to any preceding Embodiment, wherein $R^3$ is H; $C_1$-$C_4$ alkyl; —$C_1$-$C_4$alkoxy; OH; CN; halogen; —$C(O)NR^9R^{11}$; phenyl or −5 to 6 membered heterocyclyl; wherein the phenyl and 5 to 6 heterocyclyl are each optionally substituted by one or more $Z^a$ substituents.

Embodiment 22

A compound of formula (I), according to any preceding Embodiment, wherein $R^3$ is H; $C_1$-$C_4$ alkyl; —$C_1$-$C_4$ alkoxy; halogen or —$C(O)NR^9R^{11}$.

Embodiment 23

A compound of formula (I), according to any preceding Embodiment, wherein $R^3$ is H.

Embodiment 24

A compound of formula (I), according to any preceding Embodiment, wherein $R^4$ is H.

Embodiment 25

A compound of formula (I), according to any preceding Embodiment, wherein $R^5$ is H, $C_1$-$C_4$ alkyl or $C_1$-$C_4$ haloalkyl.

Embodiment 26

A compound of formula (I), according to any preceding Embodiment, wherein $R^5$ is H or methyl.

Embodiment 27

A compound of formula (I), according to any preceding Embodiment, wherein $R^5$ is H.

Embodiment 28

A compound of formula (I), according to any preceding Embodiment, wherein $R^4$ is H and $R^5$ is H.

Embodiment 29

A compound of formula (I), according to any preceding Embodiment, wherein $R^6$ is $C_1$-$C_6$ alkyl optionally substituted by $C_1$-$C_4$ alkoxy; $C_1$-$C_6$ haloalkyl; —($C_0$-$C_4$alkyl)-$C_3$-$C_6$ cycloalkyl; $C_1$-$C_4$ alkoxy optionally substituted by one or more halogen atoms; —$NR^{19}R^{21}$; —($C_0$-$C_4$ alkyl)-$C_6$-$C_{14}$aryl or —($C_0$-$C_4$ alkyl)-3 to 14 membered heterocyclyl; wherein the cycloalkyl, —($C_0$-$C_4$ alkyl)-$C_6$-$C_{14}$ aryl and —($C_0$-$C_4$ alkyl)-3 to 14 heterocyclyl are each optionally substituted by one or more Z substituents.

Embodiment 30

A compound of formula (I), according to any preceding Embodiment, wherein $R^6$ is $C_1$-$C_6$ alkyl optionally substituted by one or more $C_1$-$C_4$ alkoxy; $C_1$-$C_6$ haloalkyl; —($C_0$-$C_1$alkyl)-$C_3$-$C_6$cycloalkyl; $C_1$-$C_4$alkoxy optionally substituted by one or more halogen atoms; —$NR^{19}R^{21}$; —($C_0$-$C_4$ alkyl)-$C_6$-$C_{10}$aryl or —($C_0$-$C_4$ alkyl)-5 to 6 membered heterocyclyl; wherein the —($C_0$-$C_4$alkyl)-$C_3$-$C_6$cycloalkyl, —($C_0$-$C_4$ alkyl)-$C_6$-$C_{14}$aryl and —($C_0$-$C_4$ alkyl)-5 to 6 membered heterocyclyl are each optionally substituted by one or more Z substituents.

Embodiment 31

A compound of formula (I), according to any preceding Embodiment, wherein $R^6$ is $C_1$-$C_6$ alkyl optionally substituted by $C_1$-$C_4$ alkoxy; —($C_0$-$C_2$alkyl)-$C_3$-$C_6$cycloalkyl; $C_1$-$C_4$ alkoxy; —$C_6$-$C_{10}$aryl or —($C_0$-$C_2$ alkyl)-5 to 6 membered heterocyclyl; wherein the —($C_0$-$C_2$alkyl)-$C_3$-$C_6$cycloalkyl, —($C_0$-$C_2$ alkyl)-$C_6$-$C_{10}$aryl and —($C_0$-$C_2$alkyl)-5 to 6 membered heterocyclyl are each optionally substituted by one or more Z substituents.

Embodiment 32

A compound of formula (I), according to any preceding Embodiment, wherein $R^6$ is $C_1$-$C_6$ alkyl optionally substituted by $C_1$-$C_4$ alkoxy; —($C_0$-$C_1$alkyl)-cyclohexyl; phenyl or —($C_0$-$C_4$ alkyl)-5 to 6 membered heterocyclyl; wherein the —($C_0$-$C_1$alkyl)-cyclohexyl, phenyl and —($C_0$-$C_1$ alkyl)-5 to 6 membered heterocyclyl are each optionally substituted by one or more Z substituents.

Embodiment 33

A compound of formula (I), according to any one of Embodiments 1 to 30, wherein $R^6$ is $C_1$-$C_4$ alkyl optionally substituted by one or more $C_1$-$C_4$ alkoxy; phenyl; $C_1$-$C_4$ haloalkyl; tetrahydrofuran; pyrrolidine, —$CH_2$-pyrrolidine or —$CH_2$-piperidine; wherein phenyl, tetrahydrofuran, pyrrolidine, —$CH_2$-pyrrolidine and —$CH_2$-piperidine are each optionally substituted by one or more Z substituents.

Embodiment 34

A compound of formula (I), according to any one of Embodiments 1 to 30, wherein $R^6$ is —($C_0$-$C_2$ alkyl)-5 to 6 membered heterocyclyl, optionally substituted by one, two or three Z substituents.

Embodiment 35

A compound of formula (I), according to any one of Embodiments 1 to 30, wherein $R^6$ is

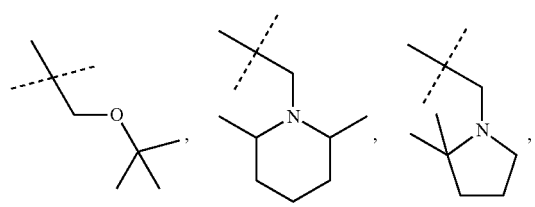

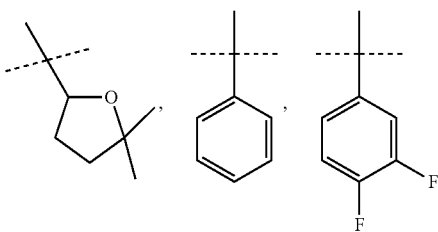

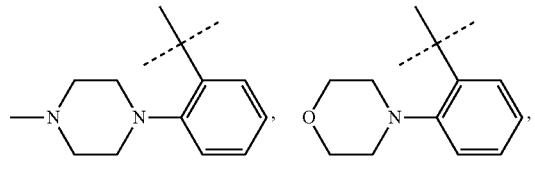

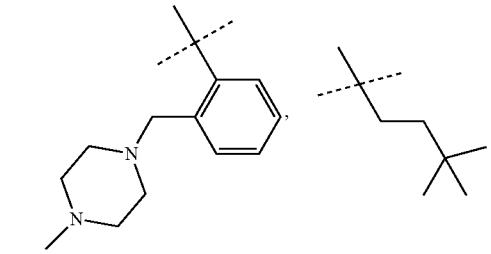

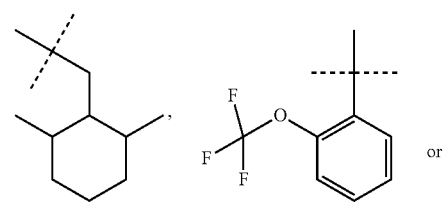

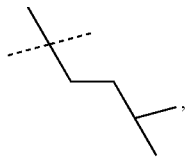

Embodiment 36

A compound of formula (I), according to any one of Embodiments 1 to 30, wherein $R^6$ is

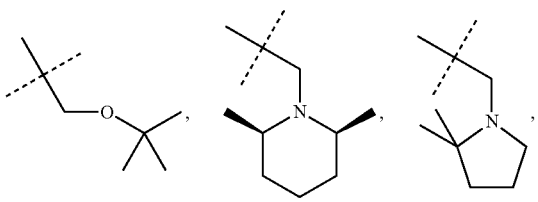

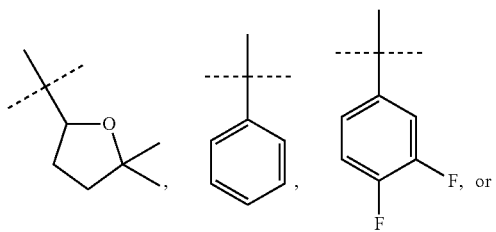

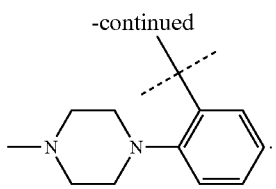

Embodiment 37

A compound of formula (I), according to any preceding Embodiment, wherein each $Z^a$ is independently OH; —($C_0$-$C_4$ alkyl)-$C_6$ aryl; —O—$C_6$ aryl; $C_1$-$C_4$ alkyl optionally substituted by one or more OH, CN or —$NR^{19a}R^{21a}$; $C_1$-$C_4$ haloalkyl; $C_1$-$C_4$ alkoxy optionally substituted by one or more OH, —$CO_2R^{19a}$, —$NR^{19a}R^{21a}$ or $C_1$-$C_4$ alkoxy; —$NR^{18a}C(O)R^{21a}$; —$C(O)NR^{19a}R^{21a}$; —$NR^{19a}C(O)NR^{19a}R^{21a}$; —$NR^{19a}R^{21a}$; —($C_0$-$C_4$ alkyl)-$C(O)OR^{18a}$; —($C_0$-$C_4$ alkyl)-$C(O)R^{19a}$; oxo; CN; $NO_2$; halogen or —($C_0$-$C_4$ alkyl)-4 to 6 membered heterocyclyl; wherein the —($C_0$-$C_4$ alkyl)-$C_6$ aryl, —O—$C_6$ aryl and —($C_0$-$C_4$ alkyl)-4 to 6 membered heterocyclyl are each optionally substituted by halogen, $C_1$-$C_4$ alkyl, $C_1$-$C_4$ haloalkyl or $C_1$-$C_4$ alkoxy optionally substituted by one or more halogens.

Embodiment 38

A compound of formula (I), according to any preceding Embodiment, wherein each $Z^a$ is independently OH; $C_1$-$C_4$ alkyl optionally substituted by one or more OH or —$NR^{19a}R^{21a}$; $C_1$-$C_4$ haloalkyl; $C_1$-$C_4$ alkoxy optionally substituted by one or more OH, $C_1$-$C_4$ alkoxy or —$NR^{19a}R^{21a}$; —$C(O)NR^{19a}R^{21a}$; CN; halogen or —($C_0$-$C_4$ alkyl)-4 to 6 membered heterocyclyl; wherein the —($C_0$-$C_4$ alkyl)-4 to 6 membered heterocyclyl are each optionally substituted by halogen, $C_1$-$C_4$ haloalkyl, or $C_1$-$C_4$ alkoxy optionally substituted by one or more halogens.

Embodiment 39

A compound of formula (I), according to any preceding Embodiment, wherein each $Z^a$ is independently $C_1$-$C_4$ alkyl optionally substituted by one or more OH or —$NR^{19a}R^{21a}$; $C_1$-$C_4$ haloalkyl; $C_1$-$C_4$ alkoxy optionally substituted by one or more OH, $C_1$-$C_4$ alkoxy or —$NR^{19a}R^{21a}$; —$C(O)NR^{19a}R^{21a}$; halogen or —($C_0$-$C_4$ alkyl)-4 to 6 membered heterocyclyl; wherein the —($C_0$-$C_4$ alkyl)-4 to 6 membered heterocyclyl is optionally substituted by halogen, $C_1$-$C_4$ alkyl or $C_1$-$C_4$ haloalkyl.

Embodiment 40

A compound of formula (I), according to any preceding Embodiment, wherein each $Z^a$ is independently $C_1$-$C_4$ alkyl optionally substituted by one or more OH or —$NR^{19a}R^{21a}$.

Embodiment 41

A compound of formula (I), according to any one of Embodiments 1 to 39, wherein each $Z^a$ is independently fluorine, bromine, chlorine, methyl, methoxy, —$CH_2NH_2$,

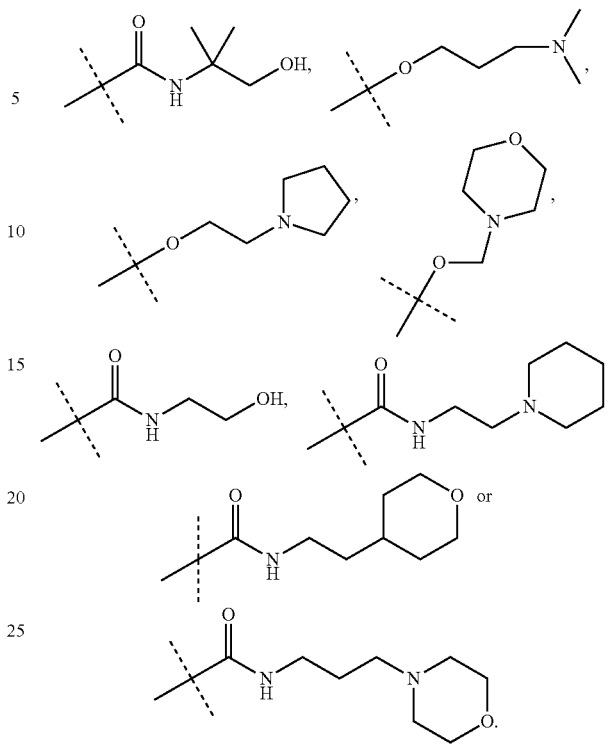

Embodiment 42

A compound of formula (I), according to any preceding Embodiment, wherein each Z is independently —($C_0$-$C_4$ alkyl)-$C_6$ aryl; —O—$C_6$ aryl; $C_1$-$C_4$ alkyl optionally substituted by one or more CN or —$NR^{19}R^{21}$; $C_1$-$C_4$ haloalkyl; $C_1$-$C_4$ alkoxy optionally substituted by one or more —$NR^{19}R^{21}$ or $C_1$-$C_4$ alkoxy; —$NR^{19}R^{21}$; —($C_0$-$C_4$ alkyl)-$C(O)R^{19}$; CN; halogen or —($C_0$-$C_4$ alkyl)-4 to 6 membered heterocyclyl; wherein the —($C_0$-$C_4$ alkyl)-$C_6$ aryl, —O—$C_6$ aryl and —($C_0$-$C_4$ alkyl)-4 to 6 membered heterocyclyl are each optionally substituted by halogen, $C_1$-$C_4$ alkyl, $C_1$-$C_4$ haloalkyl or $C_1$-$C_4$ alkoxy optionally substituted by one or more halogens.

Embodiment 43

A compound of formula (I), according to any preceding Embodiment, wherein each Z is independently $C_1$-$C_4$ alkyl optionally substituted by one or more $NH_2$; $C_1$-$C_4$ haloalkyl; $C_1$-$C_4$ alkoxy optionally substituted by one or more $C_1$-$C_4$ alkoxy or —$NR^{19}R^{21}$; CN; halogen or —($C_0$-$C_4$ alkyl)-4 to 6 membered heterocyclyl; wherein the —($C_0$-$C_4$ alkyl)-4 to 6 membered heterocyclyl is optionally substituted by halogen, $C_1$-$C_4$ alkyl, $C_1$-$C_4$ haloalkyl, or $C_1$-$C_4$ alkoxy optionally substituted by one or more halogens.

Embodiment 44

A compound of formula (I), according to any preceding Embodiment wherein each Z is independently $C_1$-$C_4$ alkoxy, halogen, $C_1$-$C_4$ alkyl or $C_1$-$C_4$ haloalkyl.

Embodiment 45

A compound of formula (I), according to any preceding Embodiment, wherein $R^9$ and $R^{11}$ are each independently H;

$C_1$-$C_6$ alkyl optionally substituted by $C_1$-$C_4$ alkoxy or OH; $C_1$-$C_6$ haloalkyl; —($C_0$-$C_1$alkyl)-$C_3$-$C_6$cycloalkyl; ($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-5- to 6-membered heterocyclyl optionally substituted by one or more groups selected from halogen, oxo, $C_1$-$C_6$ alkyl and C(O)$C_1$-$C_6$ alkyl.

Embodiment 46

A compound of formula (I), according to any one of Embodiments 1 to 44, wherein $R^9$ and $R^{11}$ together with the nitrogen atom to which they attached form a 5- to 6-membered heterocyclyl, the heterocyclyl including 0 to 3 further heteroatoms selected from N, O and S, the heterocyclyl being optionally substituted by one or more substituents selected from OH; halogen; phenyl; 5- to 10-membered heterocyclyl; $C_1$-$C_6$ alkyl; $C_1$-$C_6$ haloalkyl; $C_1$-$C_6$ alkoxy optionally substituted by one or more OH or $C_1$-$C_4$ alkoxy; and C(O)O$C_1$-$C_6$alkyl; wherein the phenyl and heterocyclyl substituent groups are themselves optionally substituted by $C_1$-$C_6$ alkyl, $C_1$-$C_6$ haloalkyl or $C_1$-$C_6$ alkoxy.

Embodiment 47

A compound of formula (I), according to any preceding Embodiment, wherein $R^{15}$ is H; $C_1$-$C_4$ alkyl; $C_1$-$C_4$ haloalkyl; $C_3$-$C_{10}$ cycloalkyl; —($C_1$-$C_4$alkyl)-$C_3$-$C_8$ cycloalkyl; —($C_0$-$C_4$ alkyl)-$C_6$-$C_{14}$aryl or —($C_0$-$C_4$ alkyl)-3 to 14 membered heterocyclyl group; wherein the $C_3$-$C_{10}$ cycloalkyl, —(—$C_1$-$C_4$alkyl)-$C_3$-$C_8$ cycloalkyl, —($C_0$-$C_4$ alkyl)-$C_6$-$C_{14}$aryl and —($C_0$-$C_4$ alkyl)-3 to 14 membered heterocyclyl groups are each optionally substituted by one or more Z substituents.

Embodiment 48

A compound of formula (I), according to any preceding Embodiment, wherein $R^{15}$ is H or $C_1$-$C_4$ alkyl.

Embodiment 49

A compound of formula (I), according to any preceding Embodiment, wherein $R^{18}$ is independently H or $C_1$-$C_4$ alkyl.

Embodiment 50

A compound of formula (I), according to any preceding Embodiment, wherein $R^{19}$ and $R^{21}$ are each independently $C_1$-$C_6$ alkyl optionally substituted by one or more $C_1$-$C_4$ alkoxy; $C_1$-$C_6$ haloalkyl; —($C_0$-$C_4$alkyl)-$C_3$-$C_6$cycloalkyl; ($C_0$-$C_4$ alkyl)-aryl optionally substituted by one or more groups selected from $C_1$-$C_6$ alkyl, $C_1$-$C_6$ alkoxy and halogen; or ($C_0$-$C_4$ alkyl)-5- to 6-membered heterocyclyl optionally substituted by one or more groups selected from halogen, $C_1$-$C_6$ alkyl and C(O)$C_1$-$C_6$ alkyl.

Embodiment 51

A compound of formula (I), according to any one of Embodiments 1 to 49, wherein $R^{19}$ and $R^{21}$ together with the nitrogen atom to which they are attached form a 5- to 6-membered heterocyclyl, which heterocyclyl includes 0 to 3 further heteroatoms selected from N, O and S, the heterocyclyl being optionally substituted by one or more substituents selected from halogen; phenyl; 5- to 10-membered heterocyclyl; $C_1$-$C_4$ alkyl; $C_1$-$C_4$ haloalkyl; $C_1$-$C_6$ alkoxy optionally substituted by one or more OH or $C_1$-$C_4$ alkoxy and C(O)O$C_1$-$C_6$alkyl; wherein the phenyl and heterocyclyl substituent groups are themselves optionally substituted by $C_1$-$C_6$ alkyl, $C_1$-$C_6$ haloalkyl or $C_1$-$C_6$ alkoxy.

Embodiment 52

A compound of formula (I), according to any preceding Embodiment, wherein $R^{18a}$ is independently H or $C_1$-$C_4$ alkyl.

Embodiment 53

A compound of formula (I), according to any preceding Embodiment, wherein $R^{19a}$ and $R^{21a}$ are each independently H; $C_1$-$C_6$ alkyl optionally substituted by $C_1$-$C_4$ alkoxy or OH; $C_1$-$C_6$ haloalkyl; —($C_0$-$C_4$alkyl)-$C_3$-$C_6$cycloalkyl; ($C_0$-$C_4$ alkyl)-aryl optionally substituted by one or more groups selected from $C_1$-$C_6$ alkyl, $C_1$-$C_6$ alkoxy and halogen; or ($C_0$-$C_4$ alkyl)-5- to 6-membered heterocyclyl optionally substituted by one or more groups selected from halogen, oxo, $C_1$-$C_6$ alkyl and C(O)$C_1$-$C_6$ alkyl.

Embodiment 54

A compound of formula (I), according to any one of Embodiments 1 to 52, wherein $R^{19a}$ and $R^{21a}$ together with the nitrogen atom to which they attached form a 5- to 6-membered heterocyclyl which heterocyclyl includes 0 to 3 further heteroatoms selected from N, O and S, the heterocyclyl being optionally substituted by one or more substituents selected from OH; halogen; phenyl; 5- to 10-membered heterocyclyl; $C_1$-$C_4$ alkyl; $C_1$-$C_4$ haloalkyl; $C_1$-$C_6$ alkoxy optionally substituted by one or more OH or $C_1$-$C_4$ alkoxy; and C(O)O$C_1$-$C_6$alkyl; wherein the phenyl and heterocyclyl substituent groups are themselves optionally substituted by $C_1$-$C_6$ alkyl, $C_1$-$C_6$ haloalkyl or $C_1$-$C_6$ alkoxy.

Embodiment 55

A compound of formula (I), according to any preceding Embodiment, wherein the compounds are represented by formula II:

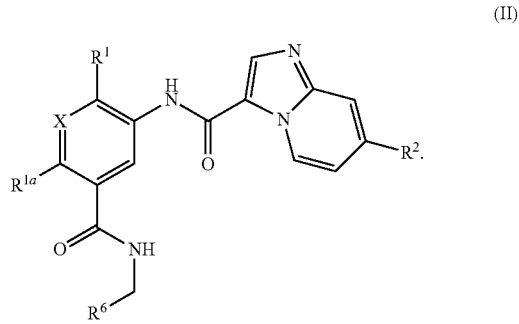

(II)

Embodiment 56

A compound of formula (II), or a pharmaceutically acceptable salt thereof:

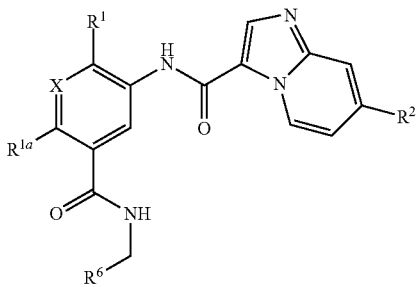

(II)

wherein
$R^1$ is $C_1$-$C_4$ alkyl, $C_1$-$C_4$ alkoxy, CN or halogen;
$R^{1a}$ is H, halogen, $C_1$-$C_4$ alkyl or $C_1$-$C_4$ haloalkyl;
X is N or CH;
$R^2$ is H; $C_1$-$C_4$ alkyl optionally substituted by one or more OH, —$NR^9R^{11}$ or $C_1$-$C_4$ alkoxy; $C_1$-$C_4$ haloalkyl; $C_2$-$C_6$ alkynyl substituted by one or more halogen, OH, —$NR^9R^{11}$ or $C_1$-$C_4$ alkoxy; $C_3$-$C_6$ cycloalkyl; —($C_1$-$C_4$ alkyl)-$C_3$-$C_6$ cycloalkyl; $C_1$-$C_6$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-$C(O)NR^9R^{11}$; —($C_0$-$C_4$ alkyl)-$C_6$-$C_{14}$aryl; or —($C_0$-$C_4$ alkyl)-3 to 14 membered heterocyclyl; wherein the $C_3$-$C_6$cycloalkyl, —($C_0$-$C_4$ alkyl)-$C_6$-$C_{14}$aryl and —($C_0$-$C_4$ alkyl)-3 to 14 heterocyclyl are each optionally substituted by one or more $Z^a$ substituents;
$R^6$ is $C_1$-$C_6$ alkyl optionally substituted by one or more $C_1$-$C_4$ alkoxy; $C_1$-$C_6$ haloalkyl; —($C_0$-$C_1$alkyl)-$C_3$-$C_6$cycloalkyl; $C_1$-$C_6$ alkoxy optionally substituted by one or more halogen atoms; —$NR^{19}R^{21}$; —($C_0$-$C_4$ alkyl)-$C_6$-$C_{10}$aryl; or —($C_0$-$C_4$ alkyl)-5 to 6 membered heterocyclyl; wherein the —($C_0$-$C_1$alkyl)-$C_3$-$C_6$cycloalkyl, —($C_0$-$C_4$ alkyl)-$C_6$-$C_{14}$aryl and —($C_0$-$C_4$ alkyl)-3 to 14 heterocyclyl are each optionally substituted by one or more Z substituents.
each $Z^a$ is independently OH; $C_1$-$C_4$ alkyl optionally substituted by one or more OH or $NH_2$; $C_1$-$C_4$ haloalkyl; $C_1$-$C_4$ alkoxy optionally substituted by one or more OH, $C_1$-$C_4$ alkoxy or —$NR^{19a}R^{21a}$; $C(O)NR^{19a}R^{21a}$; CN; halogen or —($C_0$-$C_4$ alkyl)-4 to 6 membered heterocyclyl; wherein the -heterocyclyl is optionally substituted by halogen, $C_1$-$C_4$ alkyl optionally substituted by one or more halogen atoms, or $C_1$-$C_4$ alkoxy optionally substituted by one or more halogens;
each $Z^a$ is independently $C_1$-$C_4$ alkyl optionally substituted by one or more $NH_2$; $C_1$-$C_4$ haloalkyl; $C_1$-$C_4$ alkoxy optionally substituted by one or more $C_1$-$C_4$ alkoxy or —$NR^{19}R^{21}$; CN; halogen or —($C_0$-$C_4$ alkyl)-4 to 6 membered heterocyclyl; wherein the heterocyclyl contains at least one heteroatom selected from N, O and S, wherein the heterocyclyl is optionally substituted by halogen, $C_1$-$C_4$ alkyl, $C_1$-$C_4$ haloalkyl or $C_1$-$C_4$ alkoxy optionally substituted by one or more halogens;
$R^9$ and $R^{11}$ are each independently H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$cycloalkyl; —($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-5- to 6-membered heterocyclyl optionally substituted by one or more groups selected from halogen, oxo, $C_1$-$C_6$ alkyl and —$C(O)C_1$-$C_6$ alkyl;
$R^{15}$ is H or $C_1$-$C_4$ alkyl;

$R^{19}$ and $R^{21}$ are each independently $C_1$-$C_6$ alkyl optionally substituted by one or more $C_1$-$C_4$ alkoxy; $C_1$-$C_6$ haloalkyl; —($C_0$-$C_4$alkyl)-$C_3$-$C_6$cycloalkyl; —($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-5- to 6-membered heterocyclyl optionally substituted by one or more groups selected from halogen, $C_1$-$C_6$ alkyl and —$C(O)C_1$-$C_6$ alkyl;
$R^{19a}$ and $R^{21a}$ are each independently H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$cycloalkyl; ($C_0$-$C_4$ alkyl)-aryl optionally substituted by one or more groups selected from $C_1$-$C_6$ alkyl, $C_1$-$C_6$ alkoxy and halogen; or ($C_0$-$C_4$ alkyl)-5- to 6-membered heterocyclyl optionally substituted by one or more groups selected from halogen, oxo, $C_1$-$C_6$ alkyl and $C(O)C_1$-$C_6$ alkyl.

Embodiment 57

A compound of formula (I), according to any one of Embodiments 1 to 54, wherein the compounds are represented by formula (III):

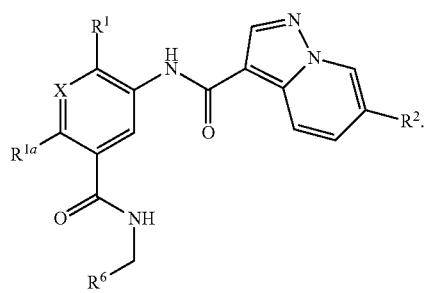

(III)

Embodiment 58

A compound of formula (III), or a pharmaceutically acceptable salt thereof:

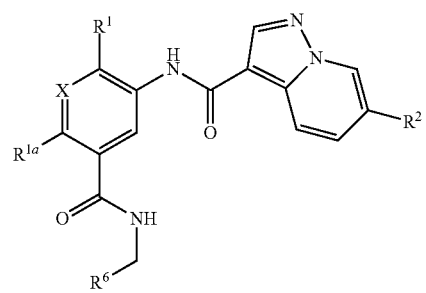

(III)

wherein
$R^1$ is $C_1$-$C_4$ alkyl, $C_1$-$C_4$ alkoxy, CN or halogen;
$R^{1a}$ is H, halogen, $C_1$-$C_4$ alkyl or $C_1$-$C_4$ haloalkyl;
X is N or CH;
$R^2$ is H; $C_1$-$C_4$ alkyl optionally substituted by one or more OH, —$NR^9R^{11}$ or $C_1$-$C_4$ alkoxy; $C_1$-$C_4$ haloalkyl; $C_2$-$C_6$ alkynyl substituted by one or more halogen, OH, —$NR^9R^{11}$ or $C_1$-$C_4$ alkoxy; $C_3$-$C_6$ cycloalkyl; —($C_1$-$C_4$ alkyl)-$C_3$-$C_6$ cycloalkyl; $C_1$-$C_4$ alkoxy optionally substituted by one or more halogen, —$NR^9R^{11}$ or OH; OH; CN; halogen; —($C_0$-

$C_4$ alkyl)-$NR^9R^{11}$; —($C_0$-$C_4$ alkyl)-$CO_2R^{15}$; —($C_0$-$C_4$ alkyl)-C(O)$NR^9R^{11}$; —($C_0$-$C_4$ alkyl)-$C_6$-$C_{14}$aryl; or —($C_0$-$C_4$ alkyl)-3 to 14 membered heterocyclyl; wherein the $C_3$-$C_6$cycloalkyl, —($C_0$-$C_4$ alkyl)-$C_6$-$C_{14}$aryl and —($C_0$-$C_4$ alkyl)-3 to 14 heterocyclyl are each optionally substituted by one or more $Z^a$ substituents;

$R^6$ is $C_1$-$C_6$ alkyl optionally substituted by one or more $C_1$-$C_4$ alkoxy; $C_1$-$C_4$ haloalkyl; —($C_0$-$C_1$alkyl)-$C_3$-$C_6$cycloalkyl; $C_1$-$C_4$alkoxy optionally substituted by one or more halogen atoms; —$NR^{19}R^{21}$; —($C_0$-$C_4$ alkyl)-$C_6$-$C_{10}$aryl or —($C_0$-$C_4$ alkyl)-5 to 6 membered heterocyclyl; wherein the —($C_0$-$C_1$alkyl)-$C_3$-$C_6$cycloalkyl, —($C_0$-$C_4$ alkyl)-$C_6$-$C_{10}$aryl and —($C_0$-$C_4$ alkyl)-5 to 6 membered heterocyclyl are each optionally substituted by one or more Z substituents;

each $Z^a$ is independently OH; $C_1$-$C_4$ alkyl optionally substituted by one or more OH or $NH_2$; $C_1$-$C_4$ alkyl; $C_1$-$C_4$ haloalkyl; $C_1$-$C_4$ alkoxy optionally substituted by one or more OH, $C_1$-$C_4$ alkoxy or —$NR^{19a}R^{21a}$; C(O)$NR^{19a}R^{21a}$; CN; halogen or —($C_0$-$C_4$ alkyl)-4 to 6 membered heterocyclyl; wherein the heterocyclyl is optionally substituted by halogen, $C_1$-$C_4$ alkyl, $C_1$-$C_4$ haloalkyl or $C_1$-$C_4$ alkoxy optionally substituted by one or more halogens;

each Z is independently $C_1$-$C_4$ alkyl optionally substituted by one or more $NH_2$; $C_1$-$C_4$ alkyl; $C_1$-$C_4$ haloalkyl; $C_1$-$C_4$ alkoxy optionally substituted by one or more $C_1$-$C_4$ alkoxy or —$NR^{19}R^{21}$; CN, halogen or —($C_0$-$C_4$ alkyl)-4 to 6 membered heterocyclyl; wherein the heterocyclyl is optionally substituted by halogen, $C_1$-$C_4$ alkyl, $C_1$-$C_4$ haloalkyl or $C_1$-$C_4$ alkoxy optionally substituted by one or more halogens;

$R^9$ and $R^{11}$ are each independently H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$cycloalkyl; —($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-5- to 6-membered heterocyclyl optionally substituted by one or more groups selected from halogen, oxo, $C_1$-$C_6$ alkyl and —C(O)$C_1$-$C_6$ alkyl;

$R^{15}$ is H or $C_1$-$C_4$ alkyl;

$R^{19}$ and $R^{21}$ are each independently $C_1$-$C_6$ alkyl optionally substituted by one or more $C_1$-$C_4$ alkoxy; $C_1$-$C_6$ haloalkyl; —($C_0$-$C_4$alkyl)-$C_3$-$C_6$cycloalkyl; —($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-5- to 6-membered heterocyclyl optionally substituted by one or more groups selected from halogen, $C_1$-$C_6$ alkyl and —C(O)$C_1$-$C_6$ alkyl;

$R^{19a}$ and $R^{21a}$ are each independently H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$cycloalkyl; ($C_0$-$C_4$ alkyl)-aryl optionally substituted by one or more groups selected from $C_1$-$C_6$ alkyl, $C_1$-$C_6$ alkoxy and halogen; or ($C_0$-$C_4$ alkyl)-5- to 6-membered heterocyclyl optionally substituted by one or more groups selected from halogen, oxo, $C_1$-$C_6$ alkyl and C(O)$C_1$-$C_6$ alkyl.

Embodiment 59

A compound of formula (I), (I) or (III), according to any preceding Embodiment, wherein X, $R^1$, $R^{1a}$, $R^2$, $R^3$, $R^4$, $R^5$, $R^6$, Z, $Z^a$ $R^{15}$, $R^{18}$, $R^{19}$ and $R^{19}$ are those defined by the Embodiments above or by the Examples section below.

Embodiment 60

A compound of formula (I), which is selected from:
N-(2-Fluoro-5-(2-(4-methylpiperazin-1-yl)benzylcarbamoyl)phenyl)-7-(1-methyl-1H-pyrazol-5-yl)imidazo[1,2-a]pyridine-3-carboxamide;
7-(3-Fluoro-4-(2-hydroxyethylcarbamoyl)phenyl)-N-(2-fluoro-5-(2-(4-methylpiperazin-1-yl)benzylcarbamoyl)phenyl)imidazo[1,2-a]pyridine-3-carboxamide;
7-Bromo-N-(2-methyl-5-(2-(4-methylpiperazin-1-yl)benzylcarbamoyl)phenyl)imidazo[1,2-a]pyridine-3-carboxamide;
7-(1-Methyl-1H-pyrazol-5-yl)-N-(2-methyl-5-(2-(4-methylpiperazin-1-yl)benzylcarbamoyl)phenyl)imidazo[1,2-a]pyridine-3-carboxamide;
N-(2-Fluoro-5-(2-(4-methylpiperazin-1-yl)benzylcarbamoyl)phenyl)-7-(pyridine-3-yl)imidazo[1,2-a]pyridine-3-carboxamide;
N-(2-Fluoro-5-(2-(4-methylpiperazin-1-yl)benzylcarbamoyl)phenyl)-7-(1-methyl-1H-pyrazol-4-yl)imidazo[1,2-a]pyridine-3-carboxamide;
N-(5-(3,4-difluorobenzylcarbamoyl)-2-fluorophenyl)-7-(1-methyl-1H-pyrazol-5-yl) imidazo[1,2-a]pyridine-3-carboxamide;
N-(5-(benzylcarbamoyl)-2-fluorophenyl)-6-(1-methyl-1H-pyrazol-3-yl)imidazo[1,2-a]pyridine-3-carboxamide;
N-(4-fluoro-2-methyl-5-(2-(4-methyl piperazin-1-yl)benzylcarbamoyl)phenyl)-7-(pyridine-3-yl)imidazo[1,2-a]pyridine-3-carboxamide;
N-(5-(3,4-difluorobenzylcarbamoyl)-2-fluorophenyl)-7-(6-(3-(dimethyl amino) propoxy)pyridine-3-yl)imidazo[1,2-a]pyridine-3-carboxamide;
N-(5-(2-(2,6-cis-dimethylpiperidin-1-yl)ethylcarbamoyl)-2-fluorophenyl)-7-(1-methyl-1H-pyrazol-5-yl)imidazo[1,2-a]pyridine-3-carboxamide;
7-(4-(aminomethyl)phenyl)-N-(2-fluoro-5-(2-(4-methylpiperazin-1-yl)benzylcarbamoyl)phenyl)imidazo[1,2-a]pyridine-3-carboxamide;
N-(5-(2-tert-butoxyethylcarbamoyl)-2-fluorophenyl)-7-(1-(2-morpholinoethyl)-1H-pyrazol-4-yl)imidazo[1,2-a]pyridine-3-carboxamide;
N-(5-((5,5-dimethyltetrahydrofuran-2-yl)methyl carbamoyl)-2-fluorophenyl)-7-(1-(2-morpholinoethyl)-1H-pyrazol-4-yl)imidazo[1,2-a]pyridine-3-carboxamide; N-(2-fluoro-5-(2-(4-methylpiperazin-1-yl)benzylcarbamoyl) phenyl)-7-(6-methoxy pyridine-3-yl)imidazo[1,2-a]pyridine-3-carboxamide;
N-(2-fluoro-5-(2-(4-methylpiperazin-1-yl)benzylcarbamoyl)phenyl)-6-(1-methyl-1H-pyrazol-5-yl)pyrazolo[1,5-a]pyridine-3-carboxamide;
1-(2-(4-fluoro-3-(7-(pyridine-3-yl)imidazo[1,2-a]pyridine-3-carboxamido)benzamido)ethyl)-2,6-cis-dimethylpiperidine;
N-(5-(2-tert-butoxyethylcarbamoyl)-2-fluorophenyl)-6-(6-(3-(dimethylamino) propoxy)pyridine-3-yl)pyrazolo[1,5-a]pyridine-3-carboxamide;
N-(2-methyl-5-(2-(4-methylpiperazin-1-yl)benzylcarbamoyl)phenyl)-7-(pyridine-3-yl)imidazo[1,2-a]pyridine-3-carboxamide;
1-methyl-4-(2-((6-methyl-5-(7-(1-methyl-1H-pyrazol-5-yl)imidazo[1,2-a]pyridine-3-carboxamido)nicotinamido)methyl)phenyl)piperazine;
7-(1-Methyl-1H-pyrazol-4-yl)-imidazo[1,2-a]pyridine-3-carboxylic acid {5-[2-(2,6-cis-dimethyl-piperidin-1-yl)-ethylcarbamoyl]-2-fluoro-phenyl}-amide;
N-(5-(2-tert-Butoxyethylcarbamoyl)-2-fluorophenyl)-7-(6-(3-(dimethylamino)propoxy)pyridin-3-yl)imidazo[1,2-a]pyridine-3-carboxamide;

N-(5-(3,4-Difluorobenzylcarbamoyl)-2-fluorophenyl)-7-(6-(2-(pyrrolidin-1-yl)ethoxy)pyridin-3-yl)imidazo[1,2-a]pyridine-3-carboxamide;

6-(1-Methyl-1H-pyrazol-5-yl)-N-(2-methyl-5-(2-(4-methylpiperazin-1-yl)benzylcarbamoyl)phenyl)pyrazolo[1,5-a]pyridine-3-carboxamide;

N-(2-Bromo-5-(2-(4-methylpiperazin-1-yl)benzylcarbamoyl)phenyl)imidazo[1,2-a]pyridine-3-carboxamide;

N-(2-Bromo-5-(2-(4-methylpiperazin-1-yl)benzylcarbamoyl)phenyl)pyrazolo[1,5-a]pyridine-3-carboxamide;

N-(5-(3,4-Difluorobenzylcarbamoyl)-2-fluorophenyl)-7-(3-hydroxy-3-methyl butyl)imidazo[1,2-a]pyridine-3-carboxamide;

N-(5-(3,4-Difluorobenzylcarbamoyl)-2-fluorophenyl)-7-(3-fluoro-4-(2-(piperidin-1-yl)ethylcarbamoyl)phenyl)imidazo[1,2-a]pyridine-3-carboxamide;

N-(5-(3,4-Difluorobenzylcarbamoyl)-2-fluorophenyl)-7-(3-fluoro-4-(2-(tetrahydro-2H-pyran-4-yl)ethylcarbamoyl)phenyl)imidazo[1,2-a]pyridine-3-carboxamide;

N-(5-(3,4-Difluorobenzylcarbamoyl)-2-fluorophenyl)-7-(3-fluoro-4-(3-morpholino propylcarbamoyl)phenyl)imidazo[1,2-a]pyridine-3-carboxamide;

6-(1-Methyl-1H-pyrazol-5-yl)-N-(2-methyl-5-(2-(4-methylpiperazin-1-yl)benzylcarbamoyl)pyridin-3-yl)pyrazolo[1,5-a]pyridine-3-carboxamide;

N-(5-((5,5-Dimethyltetrahydrofuran-2-yl)methylcarbamoyl)-2-fluorophenyl)-7-(6-(4-methylpiperazin-1-yl)pyridin-3-yl)imidazo[1,2-a]pyridine-3-carboxamide;

N-(5-(3,4-Difluorobenzylcarbamoyl)-2-fluorophenyl)-7-(1-(3-(dimethyl amino)propyl)-1H-pyrazol-4-yl)imidazo[1,2-a]pyridine-3-carboxamide;

N-(5-((5,5-Dimethyltetrahydrofuran-2-yl)methylcarbamoyl)-2-fluorophenyl)-7-(5-((tetrahydro-2H-pyran-4-ylamino)methyl)pyridin-3-yl)imidazo[1,2-a]pyridine-3-carboxamide;

(S)—N-(5-(((5,5-Dimethyltetrahydrofuran-2-yl)methyl)carbamoyl)-2-fluorophenyl)-7-(5-(((2-fluoroethyl)amino)methyl)pyridin-3-yl)imidazo[1,2-a]pyridine-3-carboxamide;

(R)—N-(5-(((5,5-dimethyltetrahydrofuran-2-yl)methyl)carbamoyl)-2-fluorophenyl)-7-(5-(((2-methoxyethyl)(methyl)amino)methyl)pyridin-3-yl) imidazo[1,2-a]pyridine-3-carboxamide;

(R)-7-(5-(((tert-butylamino)methyl)pyridin-3-yl)-N-(5-(((5,5-dimethyltetrahydrofuran-2-yl)methyl)carbamoyl)-2-fluorophenyl) imidazo[1,2-a]pyridine-3-carboxamide;

N-(5-(3,4-Difluorobenzylcarbamoyl)-2-fluorophenyl)-7-(6-(2-(pyrrolidin-1-yl)ethoxy)pyridin-3-yl)imidazo[1,2-a]pyridine-3-carboxamide;

N-(5-((2-(tert-Butoxy)ethyl)carbamoyl)-2-fluoro phenyl)-7-(6-(2-(pyrrolidin-1-yl) ethoxy)pyridin-3-yl) imidazo[1,2-a]pyridine-3-carboxamide;

N-(5-(((5,5-dimethyl tetrahydrofuran-2-yl)methyl)carbamoyl)-2-fluorophenyl)-7-(6-((1-methyl piperidin-4-yl)oxy)pyridin-3-yl)imidazo[1,2-a]pyridine-3-carboxamide;

6-(1-Methyl-1H-pyrazol-5-yl)-N-(2-methyl-5-(2-(4-methylpiperazin-1-yl)benzylcarbamoyl)phenyl)pyrazolo[1,5-a]pyridine-3-carboxamide;

N-(2-Bromo-5-(2-(4-methylpiperazin-1-yl)benzylcarbamoyl)phenyl)imidazo[1,2-a]pyridine-3-carboxamide;

N-(2-Bromo-5-(2-(4-methylpiperazin-1-yl)benzylcarbamoyl)phenyl)pyrazolo[1,5-a]pyridine-3-carboxamide;

N-(5-(3,4-Difluorobenzylcarbamoyl)-2-fluorophenyl)-7-(3-hydroxy-3-methyl butyl)imidazo[1,2-a]pyridine-3-carboxamide;

N-(5-(3,4-Difluorobenzylcarbamoyl)-2-fluorophenyl)-7-(3-fluoro-4-(2-(piperidin-1-yl)ethylcarbamoyl)phenyl)imidazo[1,2-a]pyridine-3-carboxamide;

N-(5-(3,4-Difluorobenzylcarbamoyl)-2-fluorophenyl)-7-(3-fluoro-4-(2-(tetrahydro-2H-pyran-4-yl)ethylcarbamoyl)phenyl)imidazo[1,2-a]pyridine-3-carboxamide;

N-(5-((2-(2,2-Dimethylpyrrolidin-1-yl)ethyl)carbamoyl)-2-fluorophenyl)-7-(1-methyl-1H-pyrazol-4-yl)imidazo[1,2-a]pyridine-3-carboxamide;

N-(5-(2-(2,2-Dimethylpyrrolidin-1-yl)ethylcarbamoyl)-2-fluorophenyl)-7-(3-fluoro-4-((1R,2R)-2-hydroxycyclohexylcarbamoyl)phenyl)imidazo[1,2-a]pyridine-3-carboxamide;

N-(5-(2-(2,2-Dimethylpyrrolidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide;

N-(5-(2-(2,2-Dimethylpyrrolidin-1-yl)ethylcarbamoyl)-2-methylpyridin-3-yl)-6-(3-fluoro-4-(1-hydroxy-2-methylpropan-2-ylcarbamoyl)phenyl)pyrazolo[1,5-a]pyridine-3-carboxamide;

N-(5-(3,4-Difluorobenzylcarbamoyl)-2-fluorophenyl)-7-(3-fluoro-4-(3-morpholino propylcarbamoyl)phenyl)imidazo[1,2-a]pyridine-3-carboxamide;

N-(5-(2-(2,6-cis-Dimethylpiperidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide;

7-(3-Fluoro-4-(2-fluoroethylcarbamoyl)phenyl)-N-(2-fluoro-5-(2-(4-methylpiperazin-1-yl)benzylcarbamoyl)phenyl)imidazo[1,2-a]pyridine-3-carboxamide;

N-(2-Fluoro-5-(2-(4-methylpiperazin-1-yl)benzylcarbamoyl)phenyl)-7-(3-fluoro-5-(2-hydroxy ethylcarbamoyl)phenyl)imidazo[1,2-a]pyridine-3-carboxamide;

N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide;

(S)—N-(2-Fluoro-5-(2-(2-(methoxy methyl) pyrrolidin-1-yl)ethyl carbamoyl)phenyl)-7-(1-methyl-1H-pyrazol-4-yl)imidazo[1,2-a]pyridine-3-carboxamide;

N-(2-Fluoro-5-((2-(3-propylpyrrolidin-1-yl)ethyl)carbamoyl)phenyl)-7-(1-methyl-1H-pyrazol-4-yl)imidazo[1,2-a]pyridine-3-carboxamide;

(R)—N-(2-Fluoro-5-((2-(2-(methoxymethyl) pyrrolidin-1-yl)ethyl) carbamoyl)phenyl)-7-(1-methyl-1H-pyrazol-4-yl)imidazo[1,2-a]pyridine-3-carboxamide;

N-(5-((2-(3,5-Dimethylpiperidin-1-yl)ethyl)carbamoyl)-2-fluorophenyl)-7-(1-methyl-1H-pyrazol-4-yl)imidazo[1,2-a]pyridine-3-carboxamide;

N-(2-fluoro-5-((2-(2,2,6,6-tetra methylpiperidin-1-yl)ethyl)carbamoyl)phenyl)-7-(1-methyl-1H-pyrazol-5-yl)imidazo[1,2-a]pyridine-3-carboxamide;

N-(5-((2-(tert-butyl(methyl)amino)ethyl)carbamoyl)-2-fluorophenyl)-7-(1-methyl-1H-pyrazol-5-yl)imidazo[1,2-a]pyridine-3-carboxamide;

N-(5-((2-(2,2-dimethylpyrrolidin-1-yl)ethyl)carbamoyl)-2-methylpyridin-3-yl)-6-(1-methyl-1H-pyrazol-5-yl)pyrazolo[1,5-a]pyridine-3-carboxamide;

N-(5-((2-(butyl(ethyl)amino)ethyl)carbamoyl)-2-fluoro phenyl)-7-(3-fluoro-4-((2-hydroxyethyl)carbamoyl)phenyl)imidazo[1,2-a]pyridine-3-carboxamide;

7-(3-fluoro-4-((1-hydroxy-2-methylpropan-2-yl)carbamoyl)phenyl)-N-(2-fluoro-5-((2-(3-propylpyrrolidin-1-yl)ethyl)carbamoyl)phenyl)imidazo[1,2-a]pyridine-3-carboxamide;

N-(5-((2-(3,3-dimethylmorpholino)ethyl)carbamoyl)-2-fluorophenyl)-7-(3-fluoro-4-((1-hydroxy-2-methylpropan-2-yl)carbamoyl)phenyl)imidazo[1,2-a]pyridine-3-carboxamide;
(R)-7-(3-fluoro-4-((1-hydroxy-2-methylpropan-2-yl)carbamoyl)phenyl)-N-(2-fluoro-5-((2-(2-(methoxymethyl)pyrrolidin-1-yl)ethyl) carbamoyl)phenyl)imidazo[1,2-a]pyridine-3-carboxamide;
N-(5-((3,4-Difluorobenzyl)carbamoyl)-2-fluorophenyl)-7-(6-((2-(dimethylamino)ethyl)carbamoyl)pyridin-3-yl)imidazo[1,2-a]pyridine-3-carboxamide;
N-(5-((2-(2,2-Dimethylpiperidin-1-yl)ethyl)carbamoyl)-2-methylpyridin-3-yl)-6-(1-methyl-1H-pyrazol-4-yl)pyrazolo[1,5-a]pyridine-3-carboxamide;
N-(5-((2-(2,6-cis-Dimethylpiperidin-1-yl)ethyl)carbamoyl)-2-methylpyridin-3-yl)-6-(1-methyl-1H-pyrazol-4-yl)pyrazolo[1,5-a]pyridine-3-carboxamide;
N-(5-((2-((2S,3R)-2,3-diethylazetidin-1-yl)ethyl) carbamoyl)-2-fluorophenyl)-7-(1-methyl-1H-pyrazol-4-yl)imidazo[1,2-a]pyridine-3-carboxamide;
N-(5-(3,4-Difluorobenzylcarbamoyl)-2-fluorophenyl)-7-(6-(((2-hydroxyethyl)(methylamino)methyl)pyridin-3-yl)imidazo[1,2-a]pyridine-3-carboxamide;
N-(5-((3,4-difluorobenzyl)carbamoyl)-2-fluorophenyl)-7-(6-((methyl(phenethyl)amino)methyl)pyridin-3-yl)imidazo[1,2-a]pyridine-3-carboxamide;
N-(5-((3,4-Difluoro benzyl)carbamoyl)-2-fluorophenyl)-7-(6-((methyl(phenethyl)amino)methyl)pyridin-3-yl)imidazo[1,2-a]pyridine-3-carboxamide;
N-(5-((3,4-Difluoro benzyl)carbamoyl)-2-fluorophenyl)-7-(5-((methylamino)methyl)pyridin-3-yl)imidazo[1,2-a]pyridine-3-carboxamide;
7-(5-((Cyclohexyl amino)methyl)pyridin-3-yl)-N-(5-((3,4-difluorobenzyl) carbamoyl)-2-fluoro phenyl) imidazo[1,2-a]pyridine-3-carboxamide; and
N-(5-((3,4-Difluoro benzyl)carbamoyl)-2-fluorophenyl)-7-(5-(((2-methoxyethyl)(methyl)amino)methyl)pyridin-3-yl)imidazo[1,2-a]pyridine-3-carboxamide;
or a pharmaceutically acceptable salt thereof.

Embodiment 61

A compound of formula (I), which is selected from:
N-(5-((2-(2,2-Dimethylpyrrolidin-1-yl)ethyl)carbamoyl)-2-fluorophenyl)-7-(1-methyl-1H-pyrazol-4-yl)imidazo[1,2-a]pyridine-3-carboxamide;
N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide;
N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide;
7-(1-Methyl-1H-pyrazol-4-yl)-imidazo[1,2-a]pyridine-3-carboxylic acid {5-[2-(2,6-cis-dimethyl-piperidin-1-yl)-ethylcarbamoyl]-2-fluoro-phenyl}-amide; and
N-(5-(2-(2,6-cis-Dimethylpiperidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide;
or a pharmaceutically acceptable salt thereof.

In another embodiment, the individual compounds according to the invention are those listed in the Examples section below, as the free base or as a pharmaceutically acceptable salt thereof.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, malic acid, maleic acid, malonic acid, succinic acid, fumaric acid, L-tartaric acid, citric acid, benzoic acid, 4-hydroxybenzoic acid, mandelic acid, methanesulfonic acid, ethanesulfonic acid, p-toluenesulfonic acid, sulfosalicylic acid, L-glutamic acid, hippuric acid, nicotinic acid, adipic acid, saccharin and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$F $^{36}$Cl, $^{125}$I respectively. The invention includes various isotopically labeled compounds as defined herein, for example those into which radioactive isotopes, such as $^{3}$H and $^{14}$C, or those into which non-radioactive isotopes, such as $^{2}$H and $^{13}$C are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I), (II) or (III) that contain groups capable of acting as donors and/or acceptors for hydrogen bonds may be capable of forming co-crystals with suitable co-crystal formers. These co-crystals may be prepared from compounds of formula (I), (II) or (III) by known co-crystal forming procedures. Such procedures include grinding, heating, co-subliming, co-melting, or contacting in solution compounds of formula (I), (II) or (III) with the co-crystal former under crystallization conditions and isolating co-crystals thereby formed. Suitable co-crystal formers include those described in WO 2004/078163. Hence the invention further provides co-crystals comprising a compound of formula (I), (II) or (III).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by PDGFR or (ii) associated with PDGFR activity, or (iii) characterized by activity (normal or abnormal) of PDGFR; or (2) reducing or inhibiting the activity of PDGFR. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of PDGFR.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

General Synthetic Schemes

The compounds of the invention may be synthesized by the general synthetic routes below, specific examples of which are described in more detail in the Examples.

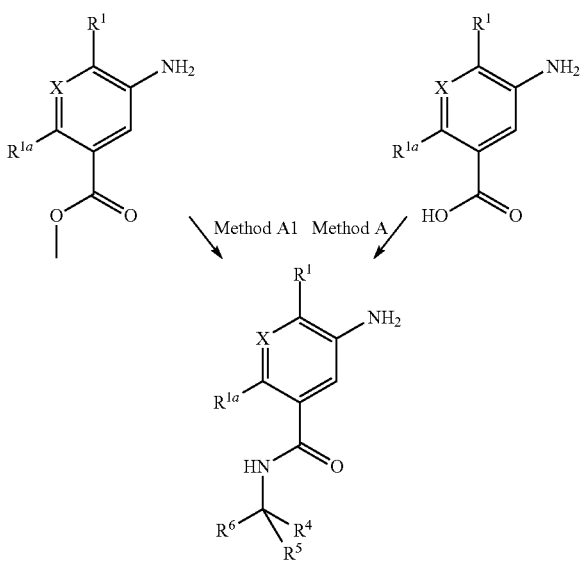

Scheme 1. Method A and A1

In scheme, the formation of the amide bond is shown using either Method A or Method A1. Method a is an amide coupling. Method A1 is a TBD coupling. This amide formation introduces the $R^6$ moeity. X, $R^1$, $R^{1a}$, $R^4$, $R^5$ and $R^6$ are as defined herein.

Method B1 and Method B2 are aniline amide couplings using acid chlorides. In addition, scheme 2 depicts the formation of an amide bond to introduce the $R^6$ moiety using Method A2, which is an amide coupling. One of Y and $Y^2$

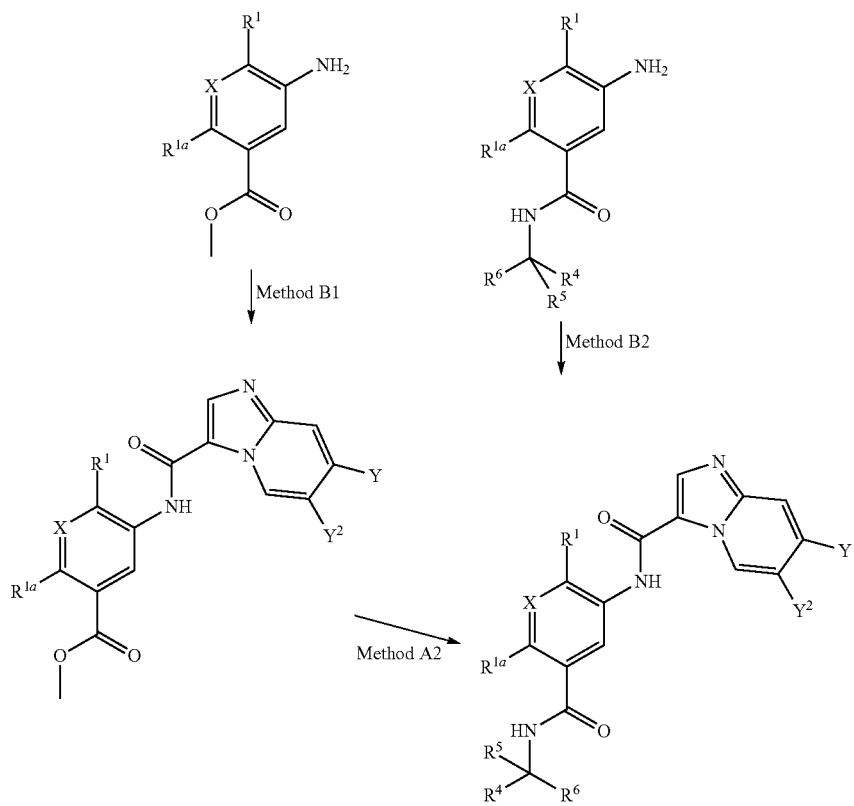

Scheme 2. Imidazopyridines

In scheme 2, the formation of the amide bond at the aniline nitrogen is shown using Method B1 and Method B2. is a halogen, such as bromine, and one of Y and $Y^2$ is hydrogen. X, $R^1$, $R^{1a}$, $R^4$, $R^5$ and $R^6$ are as defined herein.

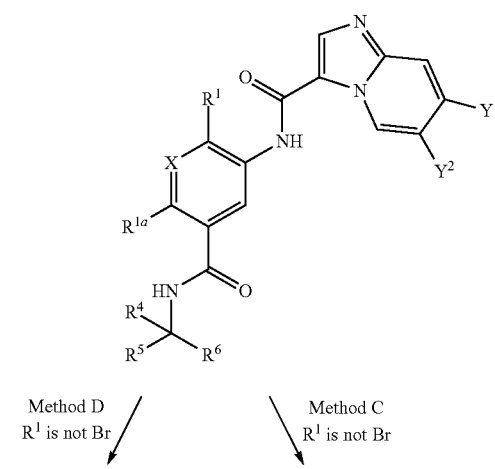

Scheme 3.

-continued

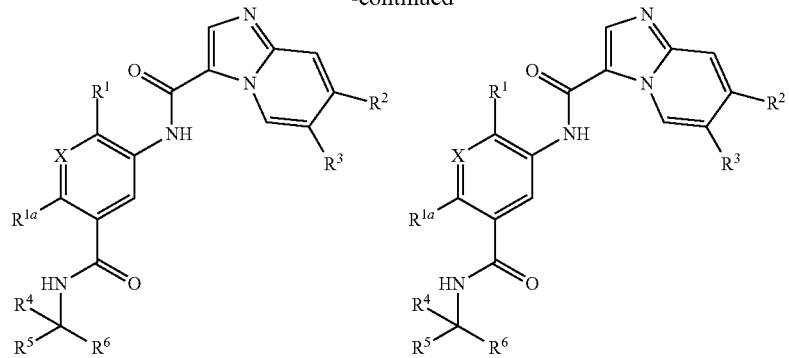

In scheme 3, the introduction of $R^2$ and/or $R^3$ is depicted as a substitution reaction at Y or $Y^2$ using Method C or Method D. Method C is a Suzuki reaction to couple aryl group at $R^2$ or $R^3$. Method D is a Negishi reaction to couple an alkyl group at $R^2$ or $R^3$. $R^1$ cannot be bromine for this reaction. One of Y and $Y^2$ is a halogen, such as bromine, and one of Y and $Y^2$ is hydrogen. X, $R^1$, $R^{1a}$, $R^2$, $R^3$, $R^4$, $R^5$ and $R^6$ are as defined herein.

In scheme 4, the formation of the amide bond at the aniline nitrogen is shown using Method B1 and Method B2. Method B1 and Method B2 are aniline amide couplings using acid chlorides. In addition, scheme 2 depicts the formation of an amide bond to introduce the $R^6$ moiety using Method A2, which is an amide coupling. One of Y and $Y^2$ is a halogen, such as bromine, and one of Y and $Y^2$ is hydrogen. X, $R^1$, $R^{1a}$, $R^4$, $R^5$ and $R^6$ are as defined herein.

Scheme 4. Pyrazolopyridines

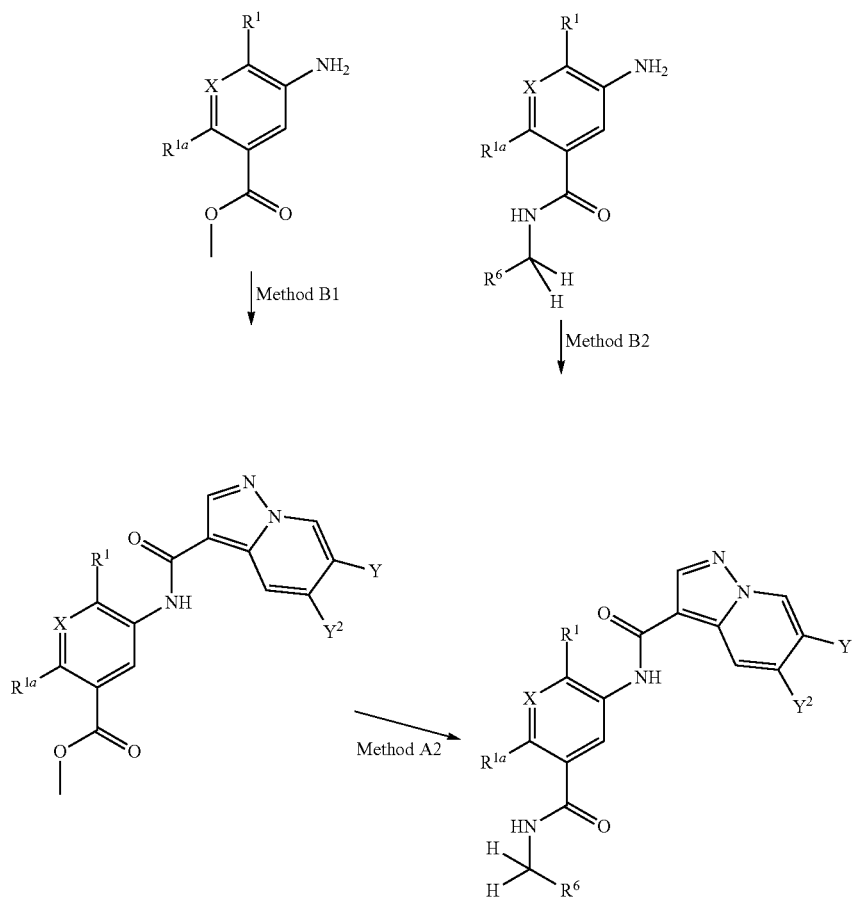

Scheme 5.

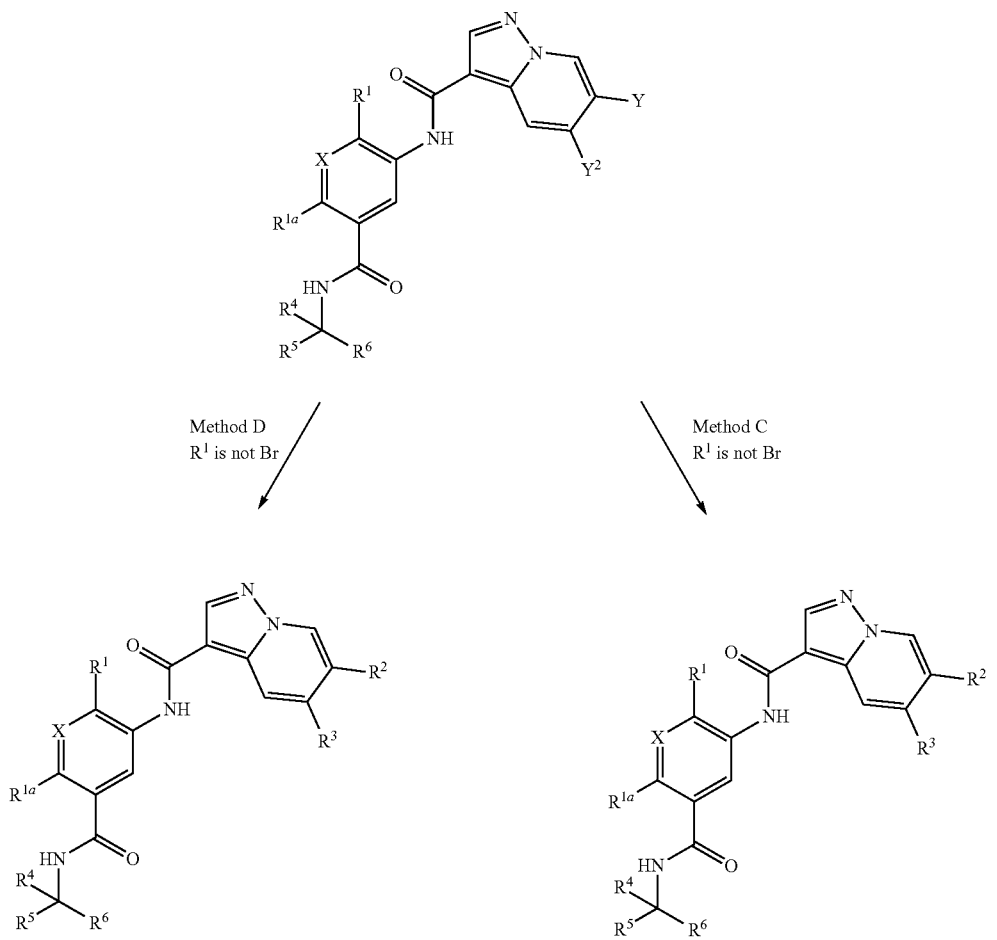

In scheme 5, the introduction of $R^2$ and/or $R^3$ is depicted as a substitution reaction at Y or $Y^2$ using Method C or Method D. Method C is a Suzuki reaction to couple aryl group at $R^2$ or $R^3$. Method D is a Negishi reaction to couple an alkyl group at $R^2$ or $R^3$. $R^1$ cannot be bromine for this reaction. One of Y and $Y^2$ is a halogen, such as bromine, and one of Y and $Y^2$ is hydrogen. X, $R^1$, $R^{1a}$, $R^2$, $R^3$, $R^4$, $R^5$ and $R^6$ are as defined herein.

Scheme 6

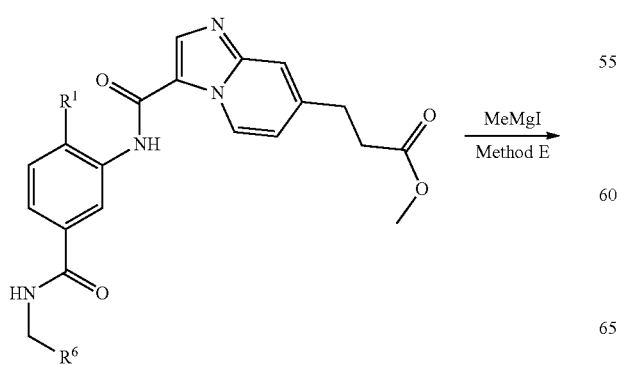

-continued

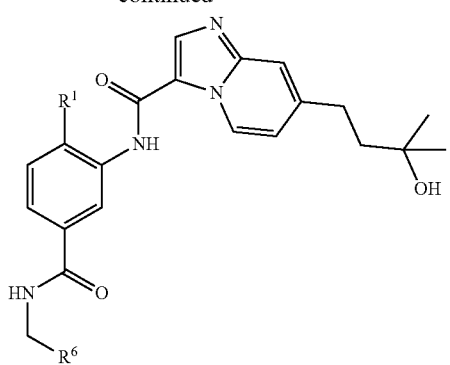

In scheme 6, the introduction of alkyl group alpha to an ester group is depicted using Method E, a Grignard addition, to form tertiary alcohol. $R^1$ and $R^6$ are as defined herein.

Scheme 7

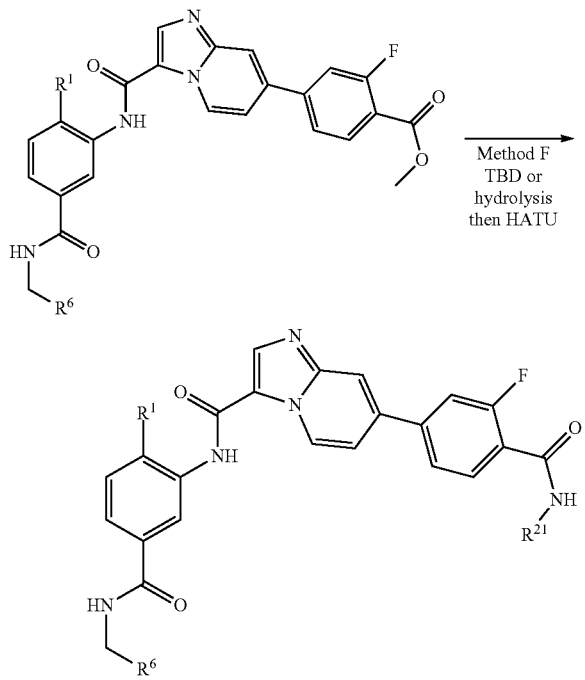

In scheme 7, the introduction of amide bond from an ester group is depicted using Method F. Method F is a TBD reaction. $R^1$, $R^6$, and $R^{21}$ are as defined herein.

Scheme 8

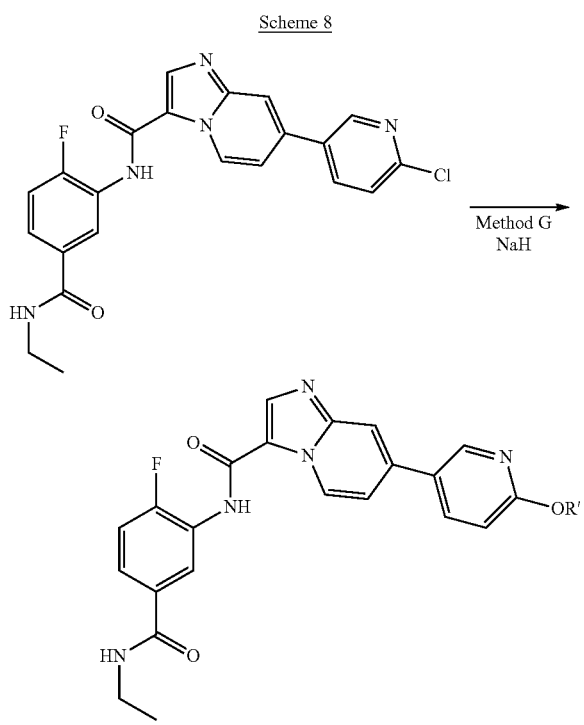

In scheme 8, the introduction of alkoxy moiety is depicted using method G. Method G is a nucleophilic displacement of a halide. R' is $C_1$-$C_4$ alkoxy optionally substituted by one or more OH, —$CO_2R^{18}$, —$NR^{19}R^{21}$ or $C_1$-$C_4$ alkoxy. $R^1$, $R^6$, $R^{18}$, $R^{19}$ and $R^{21}$ are as defined herein.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide and Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Salts of compounds of the present invention having at least one salt-forming group may be prepared in a manner known to those skilled in the art. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted into the free compounds in accordance with methods known to those skilled in the art. Metal and ammonium salts can be converted, for example, by treatment with suitable acids, and acid addition salts, for example, by treatment with a suitable basic agent.

Mixtures of isomers obtainable according to the invention can be separated in a manner known to those skilled in the art into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known to those skilled in the art, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
 a) diluents, e.g., lactose, dextrose, sucrose, mannitol, sorbitol, cellulose and/or glycine;
 b) lubricants, e.g., silica, talcum, stearic acid, its magnesium or calcium salt and/or polyethyleneglycol; for tablets also
 c) binders, e.g., magnesium aluminum silicate, starch paste, gelatin, tragacanth, methylcellulose, sodium carboxymethylcellulose and/or polyvinylpyrrolidone; if desired
 d) disintegrants, e.g., starches, agar, alginic acid or its sodium salt, or effervescent mixtures; and/or
 e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in a mixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

Where the inhalable form of the active ingredient is an aerosol composition, the inhalation device may be an aerosol vial provided with a valve adapted to deliver a metered dose, such as 10 to 100 µl, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

The invention also includes (A) an agent of the invention in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e. g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compound of the present invention may be administered either simultaneously with, or before or after, one or more other therapeutic agent. The compound of the present invention may be administered separately, by the same or different route of administration, or together in the same pharmaceutical composition as the other agents.

Another aspect of this invention relates to the fact that the compounds of formula (I), (II) or (III) and their pharmaceutically acceptable salts have beneficial pharmacological activity and, therefore, are useful as pharmaceuticals.

Therefore, according to a further aspect of the invention a compound of formula (I), (II) or (III) is hereinbefore described as a medicament. The use of compounds of formula (I), (II) or (III) in inhibiting PDGF receptor mediated biological activity is novel per se. Therefore, a compound of formula (I), (II) or (III) or pharmaceutically acceptable salt thereof is an inhibitor of PDGF receptor mediated biological activity. We particularly provide a compound of formula (I), (II) or (III) or a pharmaceutically acceptable salt thereof for the treatment of a respiratory disorder.

According to a further aspect of the invention the use of a compound of formula (I) is hereinbefore described in the manufacture of a medicament. More particularly, the use is hereinbefore described in the manufacture of a medicament for inhibiting PDGF receptor mediated biological activity. Another aspect of the invention is the use of a compound of formula (I) in the manufacture of a medicament for the treatment of a respiratory disorder.

Another aspect provided herein are pharmaceutical compositions that include a therapeutically effective amount of a compound of Formula (I), (II), or (III), or a pharmaceutical salt thereof and a pharmaceutically acceptable carrier. In certain embodiments of such pharmaceutical compositions, the pharmaceutical composition is formulated for intravenous administration, intravitrial administration, intramuscular administration, oral administration, rectal administration, transdermal administration, pulmonary administration, inhalation administration, nasal administration, topical administration, ophthalmic administration or otic administration. In other embodiments, the pharmaceutical compositions are in the form of a tablet, a pill, a capsule, a liquid, an inhalant, a nasal spray solution, a suppository, a solution, an emulsion, an ointment, eye drop or ear drop. In other embodiments, such pharmaceutical compositions further include one or more additional therapeutic agents.

Use and Method of Treating

Another aspect provided herein is the use of the compound of Formula (I), (II) or (III) or a pharmaceutically acceptable salt thereof for the treatment of a disorder or disease in a subject by inhibiting c-kit and/or PDGFR kinase activity, and such use include a therapeutically effective amount of the compound of Formula (I), (II) or (III).

Another aspect provided herein is the use of the compound of Formula (I), (II) or (III) or a pharmaceutically acceptable salt thereof for the treatment of a disorder or disease in a subject by inhibiting c-kit and/or PDGFR kinase activity, and such suc use include a therapeutically effective amount of the compound of Formula (I), (II) or (III), wherein the disease or disorder is a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, cariac hypertro-phy, cancers of the lung or other tissues in which a PDGFR isoform is mutated, overexpressed or acticviated, pulmonary arterial hypertension (PAH) or primary pulmonary hypertension (PPH). In other embodiments of this aspect, the disease is asthma, allergic rhinitis, pulmonary arterial hypertension (PAH), pulmonary fibrosis, hepatic fibrosis, cardiac fibrosis, scleroderma, irritable bowel syndrome (IBS), inflammatory bowel disease (IBD), uticaria, dermatosis, type I diabetes or type II diabetes.

Another aspect provided herein are uses for treating a disease mediated by a kinase in a patient in need therof, and such uses include a therapeutically effective amount of a compound of Formula (I), (II) or (III), the kinase is selected from c-kit, PDGFRO, PDGFRβ, p38, BCR-abl and c-FMS and the disease is a mast-cell associated disease, a respiratory disease, an inflammatory disorder, irritable bowel syndrome (IBS), inflammatory bowel disease (IBD), an autoimmune disorder, a metabolic disease, a fibrosis disease, a dermatological disease, pulmonary arterial hypertension (PAH) or primary pulmonary hypertension (PPH).

In certain embodiments of this aspect, the disease is asthma, allergic rhinitis, pulmonary arterial hypertension (PAH), pulmonary fibrosis, hepatic fibrosis, cardiac fibrosis, cardiac hypertrophy, scleroderma, irritable bowel syndrome (IBS), inflammatory bowel disease (IBD), uticaria, dermatosis, type I diabetes or type II diabetes.

Another aspect provided herein is the use of a compound of Formula (I), (II) or (III), in the manufacture of a medicament for treating a disease or disorder in a patient where modulation of a c-kit and/or PDGFR kinase is implicated.

Another aspect provided herein includes methods for treating a disease or disorder where modulation of c-kit and/or PDGFR kinase is implicated, wherein the method includes administering to a system or subject in need of such treatment an effective amount of a compound of Formula (I), (II) or (III), or pharmaceutically acceptable salts or pharmaceutical compositions thereof, thereby treating the disease or disorder. In such methods, the compound of Formula (I), (II) or (III), is an inhibitor of c-kit and/or PDGFR kinases. In certain embodiments of such methods, the methods include administering the compound to a cell or tissue system or to a human or animal subject. In certain embodiments of such methods, the disease or condition is a metabolic disease, a fibrotic disease, cardiac hypertrophy, a respiratory disease, an inflammatory disease or disorder, a dermatological disease or an autoimmune disease. In certain embodiments of such methods, the disease or condition is asthma, allergic rhinitis, irritable bowel syndrome (IBS), inflammatory bowel disease (IBD), pulmonary arterial hypertension (PAH), pulmonary fibrosis, liver fibrosis, cardiac fibrosis, scleroderma, urticaria, dermatoses, atopic dermatitis, type I diabetes or type II diabetes.

In another embodiment the disease is selected from a a respiratory disease, an inflammatory disorder, irritable bowel syndrome (IBS), inflammatory bowel disease (IBD), aa fibrosis disease, pulmonary arterial hypertension (PAH) and primary pulmonary hypertension (PPH). In other embodiments the diseases is asthma, pulmonary arterial hypertension (PAH), pulmonary fibrosis, hepatic fibrosis, cardiac fibrosis, or cardiac hypertrophy.

Pharmaceutical Composition and Combinations

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods.
Pharmaceutical Use and Assay Compounds of Formula (I), (II) or (III) provided herein were assayed to measure their capacity to inhibit PDGFR kinases using the appropriate assay described below: PDGFR inhibition was evaluated using the Rat A10 cell proliferation.
Rat A10 Cell Proliferation Assay Rat A10 cells (ATCC) were resuspended in DMEM supplemented with 1% FBS and 10 ng/mL recombinant rat PDGF-BB at 20,000 cells/mL. The cells were aliquoted into 384 well plates at 50 µL/well and incubated for 4 hours at 37° C. 0.5 µL of test compound 3-fold serially diluted in DMSO was added to each well. The plates were returned to the incubator for a further 68 hours. 25 µL of CellTiter-Glo (Promega) was added to each well and the plates were incubated on the bench for 15 minutes. Luminescence was then read using a CLIPR CCD camera (Molecular Devices).

Data were analysed using non-linear regression fitted to sigmoidal (variable slope) curves using a four parameter logistic equation to generate IC50 values for each compound.

Compounds of the examples, herein below, generally have PDGFR $K_b$ values in the Rat A10 cell based assay below 10 µM. Table A provides a list of representative compounds with their $IC_{50}$ values.

TABLE A

| Example | PDGFR RAT(A10) $IC_{50}$ /µM |
|---|---|
| 1.1 | 0.009 |
| 1.2 | 0.040 |
| 1.4 | 0.010 |
| 1.5 | 0.004 |
| 1.9 | 0.011 |
| 1.10 | 0.045 |
| 1.15 | 0.007 |
| 1.16 | 0.027 |
| 1.19 | 0.074 |
| 1.20 | 0.013 |
| 1.21 | 0.035 |
| 2.1 | 0.003 |
| 2.6 | 0.016 |
| 3.1 | 0.013 |
| 3.2 | 0.015 |
| 3.3 | 0.01 |
| 4.1 | 0.012 |

TABLE A-continued

| Example | PDGFR RAT(A10) $IC_{50}$ /µM |
|---|---|
| 6.1 | 0.041 |
| 7.3 | 0.002 |
| 7.5 | 0.008 |
| 7.6 | 0.182 |
| 8.1 | 0.004 |
| 8.2 | 0.008 |
| 8.4 | 0.112 |
| 9.0 | 0.003 |
| 9.2 | 0.011 |
| 9.4 | 0.128 |
| 9.13 | 0.007 |
| 9.15 | 0.002 |

PDGFR inhbitors, including the compounds of formula (I), (II) or (III) are also useful as co-therapeutic agents for use in combination with second agents, such as organic nitrates and NO-donors, such as sodium nitroprusside, nitroglycerin, isosorbide mononitrate, isosorbide dinitrate, molsidomine or SIN-1, and inhalational NO; compounds that inhibit the degradation of cyclic guanosine monophosphate (cGMP) and/or cyclic adenosine monophosphate (cAMP), such as inhibitors of phosphodiesterases (PDE) 1, 2, 3, 4 and/or 5, especially PDE 5 inhibitors such as sildenafil, vardenafil and tadalafil; NO-independent, but haem-dependent stimulators of guanylate cyclase, such as in particular the compounds described in WO 00/06568, WO 00/06569, WO 02/42301 and WO 03/095451; NO- and haem-independent activators of guanylate cyclase, such as in particular the compounds described in WO 01/19355, WO 01/19776, WO 01/19778, WO 01/19780, WO 02/070462 and WO 02/070510; compounds which inhibit human neutrophilic elastase, such as sivelestat or DX-890 (Reltran); compounds inhibiting the signal transduction cascade, such as tyrosine kinase and/or serine/threonine kinase inhibitors, in particular imatinib, gefitinib, erlotinib, sorafenib and sunitinib; compounds influencing the energy metabolism of the heart, for example and preferably etomoxir, dichloroacetate, ranolazine or trimetazidine; antithrombotic agents, for example and preferably from the group comprising platelet aggregation inhibitors, anticoagulants or profibrinolytic substances; active substances for lowering blood pressure, for example and preferably from the group comprising calcium antagonists, angiotensin II antagonists, ACE inhibitors, endothelin antagonists, renin inhibitors, aldosterone synthase inhibitors, alpha receptor blockers, beta receptor blockers, mineralocorticoid receptor antagonists, Rho-kinase inhibitors and diuretics; and/or active substances that modify lipid metabolism, for example and preferably from the group comprising thyroid receptor agonists, inhibitors of cholesterol synthesis, for example and preferably HMG-CoA-reductase inhibitors or inhibitors of squalene synthesis, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists, particularly in the treatment of PAH or diseases and disorders such as those mentioned hereinbefore, e.g., as potentiators of therapeutic activity of such drugs or as a means of reducing required dosaging or potential side effects of such drugs.

In particular, an embodiment of this invention is a pharmaceutical combination comprising the compounds of formula (I), (II) or (III) and a second agent wherein the second agent is a PDEV inhibitor or neutral endopeptidase inhibitor.

The compounds of formula (I), (II) or (III) may be mixed with a second agent in a fixed pharmaceutical composition or it may be administered separately, before, simultaneously with or after the other drug substance.

Other useful combinations of PDGFR inhibitor with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

Accordingly, the invention includes as a further aspect a combination of PDGFR inhibitor with agents that inhibit ALK5 and/or ALK4 phosphorylation of Smad2 and Smad3.

Accordingly, the invention includes as a further aspect a combination of PDGFR inhibitor with second agents that are Rho-kinase inhibitors. Accordingly, the invention includes as a further aspect a combination of PDGFR inhibitor with second agents that are TPH1 antagonists.

Accordingly, the invention includes as a further aspect a combination of PDGFR inhibitor with second agents that are IP receptor agonist.

Accordingly, the invention includes as a further aspect a combination of PDGFR inhibitor with second agents that are multi-kinase inhibitors, such as imatinib mysilate (Gleevec®) or nilotinib. Imatinib functions as a specific inhibitor of a number of tyrosine kinase enzymes. It occupies the TK active site, leading to a decrease in activity. TK enzymes in the body, include the insulin receptor. Imatinib is specific for the TK domain in the Abelson proto-oncogene, c-kit and PDGF-R (platelet-derived growth factor receptor).

Accordingly, an embodiment of this invention provides a pharmaceutical combination comprising the compounds of formula (I), (II) or (III), or pharmaceutical salts thereof, and a second agent wherein the second agent is selected from phosphodiesterase V (PDEV) inhibitors, such as sildenafil or tadalafil; neutral endopeptidase inhibitors such as neutral endopeptidase 1 inhibitors; anti-inflammatory drugs including antagonists of chemokine receptors; steroids including corticosteroids such as long-acting corticosteroids; $\beta_2$-agonists including ultra-long-acting $\beta_2$-agonists; bronchodilatory drugs including anticholinergic or antimuscarinic agents, such as long-acting muscarinic antagonists; dual anti-inflammatory and bronchodilatory drugs including dual beta-2 adrenoceptor agonist/muscarinic antagonists; antihistamine drug substances; IP receptor agonists, such as as those disclosed in WO2012/007539; agents that induce pulmonary vascular vasodilation; agents that are tryptophan hydroylase 1 (TPH1) inhibitors; multi-kinase inhibitors such as c-Kit inhibitors; tyrosine kinase inhibitors such as imatinib (Gleevec®) or nilotinib; MAPK (e.g. p38) inhibitors; mTOR inhibitors (alone or in combination with PI3K inhibitors); LPA-1 inhibitors; endothelin antagonists; diuretics; aldosterone receptor blockers; and endothelin receptor blockers.

Formulation and Administration

The compounds of the invention may be administered by any appropriate route, e.g., orally, e.g., in the form of a tablet or capsule; parenterally, e.g., intravenously; by inhalation, e.g., in the treatment of inflammatory or obstructive airways disease; intranasally, e.g., in the treatment of allergic rhinitis; topically to the skin, e.g., in the treatment of atopic dermatitis; topically to the eye, e.g., in the treatment of glaucoma; or rectally, e.g., in the treatment of inflammatory bowel disease.

In a further aspect, the invention also provides a pharmaceutical composition comprising a compound of formula (I), (II), or (III) in free form or in the form of a pharmaceutically acceptable salt, optionally together with a pharmaceutically acceptable adjuvant, diluent or carrier.

The composition may contain a co-therapeutic agent such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomisable formulations or dry powder formulations.

When the composition comprises an aerosol formulation, it preferably contains, e.g., a hydro-fluoro-alkane (HFA) propellant, such as HFA134a or HFA227 or a mixture of these, and may contain one or more co-solvents known in the art such as ethanol (up to 20% by weight), and/or one or more surfactants such as oleic acid or sorbitan trioleate, and/or one or more bulking agents, such as lactose. When the composition comprises a dry powder formulation, it preferably contains, e.g., the compound of formula (I)-(III) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I), (II) or (III) either dissolved, or suspended, in a vehicle containing water, a co-solvent, such as ethanol or propylene glycol and a stabiliser, which may be a surfactant.

Thus, the present invention further includes:
(a) a compound of formula (I)-(III) in inhalable form, e.g., in an aerosol or other atomisable composition or in inhalable particulate, e.g., micronised, form;
(b) an inhalable medicament comprising a compound of formula (I), (II) or (III) in inhalable form;
(c) a pharmaceutical product comprising a compound of formula (I), (II) or (III)) in inhalable form in association with an inhalation device; and
(d) an inhalation device containing a compound of formula (I), (II) or (III) in inhalable form.

Dosages of compounds of formula (I), (II) or (III) employed in practicing the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

The present invention includes all pharmaceutically acceptable isotopically-labelled compounds of formula (I), (II) or (III) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as 2H and 3H, carbon, such as 11C, 13C and 14C, chlorine, such as 36Cl, fluorine, such as 18F, iodine, such as 123I and 125I, nitrogen, such as 13N and 15N, oxygen, such as 15O, 17O and 18O, phosphorus, such as 32P, and sulphur, such as 35S.

Substitution with heavier isotopes such as deuterium, i.e. 2H, may afford certain therapeutic advantages resulting from greater metabolic stability, for example, increased in vivo half-life or reduced dosage requirements, and hence may be preferred in some circumstances.

Isotopically-labeled compounds of formula (I), (II) or (III) can generally be prepared by conventional techniques known to those skilled in the art or by processes analogous to those described in the accompanying Examples and Preparations using an appropriate isotopically-labeled reagents in place of the non-labeled reagent previously employed.

Compounds of formula (I), (II) or (III) may be prepared by the general reactions shown in the examples herein.

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The invention is illustrated by the following Examples.

EXAMPLES

General Conditions

Mass spectra were run on LCMS systems using electrospray ionization. These were either Agilent 1100 HPLC/Micromass Platform Mass Spectrometer combinations or Waters Acquity UPLC with SQD Mass Spectrometer. $[M+H]^+$ refers to mono-isotopic molecular weights.

NMR spectra were run on open access Bruker AVANCE 400 NMR spectrometers using ICON-NMR. Spectra were measured at 298K and were referenced using the solvent peak.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art. If not defined, the terms have their generally accepted meanings.

ABBREVIATIONS aq. aqueous
br broad d doublet
DCM dichloromethane
DMF N,N-dimethylformamide
DMAC dimethylacetamide
DMSO dimethylsulfoxide
EtOAc ethyl acetate
hr hour
HOBt hydroxybenzotriazole
HPLC high pressure liquid chromatography
LC-MS liquid chromatography and mass spectrometry
MeOH methanol
MS mass spectrometry
m multiplet
min minutes
ml milliliter(s)
m/z mass to charge ratio
NMR nuclear magnetic resonance
ppm parts per million
PEAX PE-anion exchange (e.g. Isolute® PE-AX columns from Biotage)
Rt retention time
RT room temperature
s singlet
SCX-2 strong cation exchange (e.g. Isolute® SCX-2 columns from Biotage)
t triplet
TEA triethylamine
TBD 2,3,4,6,7,8-hexahydro-1H-pyrimido[1,2-a]pyrimidine
THF tetrahydrofuran Referring to the examples that follow, compounds of the preferred embodiments were synthesized using the methods described herein, or other methods, which are known in the art.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

If not indicated otherwise, the analytical HPLC conditions are as follows:

Method 2minLC_v001

| Column | Waters BEH C18 100 × 2.1 mm, 1.7 μm |
|---|---|
| Column Temp. | 50° C. |
| Eluents | A: H$_2$O, B: acetonitrile, both containing 0.1% TFA |
| Flow Rate | 0.7 ml/min |
| Gradient | 0.25 min 5% B; 5% to 95% B in 1.00 min, 0.25 min 95% B |

Method 2minLC_v002

| Column | Waters BEH C18 50 × 2.1 mm, 1.7 μm |
|---|---|
| Column Temperature | 50° C. |
| Eluents | A: H$_2$O, B: MeOH, both containing 0.1% TFA |
| Flow Rate | 0.8 ml/min |
| Gradient | 0.20 min 5% B; 5% to 95% B in 1.30 min, 0.25 min 95% B |

Method 2minLC_30_v003

| Column | Waters BEH C18 50 × 2.1 mm, 1.7 μm |
|---|---|
| Column Temperature | 50° C. |
| Eluents | A: H$_2$O, B: acetonitrile, both containing 0.1% TFA |
| Flow Rate | 0.8 ml/min |
| Gradient | 0.25 min 30% B; 30% to 95% B in 1.00 min, 0.25 min 95% B |

Method 10minLC_v003

| Column | Waters BEH C18 50 × 2.1 mm, 1.7 μm |
|---|---|
| Column Temperature | 50° C. |
| Eluents | A: H$_2$O, B: acetonitrile, both containing 0.1% TFA |
| Flow Rate | 0.8 ml/min |
| Gradient | 0.20 min 5% B; 5% to 95% B in 7.80 min, 1.00 min 95% B |

Method LowpH_v002

| Column | Phenomenex Gemini C18 50 × 4.6 mm, 3.0 mm |
|---|---|
| Column Temperature | 50° C. |
| Eluents | A: H2O, B: MeOH, both containing 0.1% TFA |
| Flow Rate | 1.0 ml/min |
| Gradient | 5% to 95% B in 2.0 min, 0.2 min 95% B |

Method A

| Column: | Acquity HSS T3 1.8 μm 2.1 × 50 mm at 50° C. |
|---|---|
| Eluent A: | water + 0.05% formic acid + 3.75 mM ammonium acetate |
| Eluent B: | acetonitrile + 0.04% formic acid |
| Gradient: | 2% to 98% B in 1.4 min-flow 1.2 ml/min |

Method 10 min LC

| Column | Aglient, Poroshell 120 SB-C18 2.7 μm 3.0 × 50 mm |
|---|---|
| Column Temp. | 30° C. |
| Eluents | B: H$_2$O, C: acetonitrile, both containing 0.1% Formic acid |
| Flow Rate | 0.8 ml/min |
| Gradient | 0.50 min 5% C; 5% to 95% C in 6.50 min, 95% to 5% C in 3 min |

Example compounds of the present invention include:

Preparation of Final Compounds

Example 1.1

N-(2-Fluoro-5-(2-(4-methylpiperazin-1-yl)benzyl-carbamoyl)phenyl)-7-(1-methyl-1H-pyrazol-5-yl)imidazo[1,2-a]pyridine-3-carboxamide

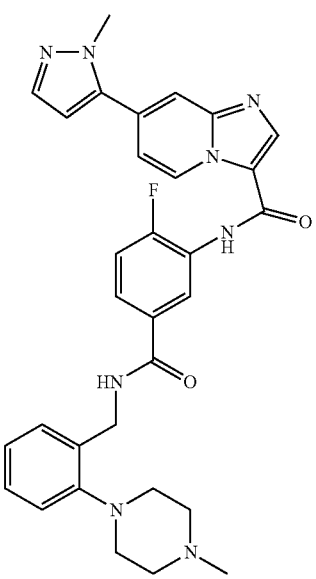 [SMILES: CN1CCN(c2ccccc2CNC(=O)c2ccc(F)c(NC(=O)c3cnc4cc(-c5ccnn5C)ccn34)c2)CC1]

Step 1: 7-Bromo-N-(2-fluoro-5-(2-(4-methylpiperazin-1-yl)benzylcarbamoyl)phenyl)imidazo[1,2-a]pyridine-3-carboxamide Methyl 3-(7-bromoimidazo[1,2-a]pyridine-3-carboxamido)-4-fluorobenzoate (Intermediate 1A)(1.08 g, 2.75 mmol), TBD (0.383 g, 2.75 mmol) and (2-(4-methylpiperazin-1-yl)phenyl)methanamine (0.565 g, 2.75 mmol) in toluene (35 ml) were heated to 80° C. for 6 hrs. A further portion of TBD (0.06 g, 0.431 mmol) and (2-(4-methylpiperazin-1-yl)phenyl)methanamine (0.100 g, 0.487 mmol) were added and the mixture was heated at 80° C. overnight. TBD (0.06 g, 0.431 mmol) was added and heating continued at 110° C. overnight. Toluene was removed in vacuo and the resulting solid was partitioned between aqueous sodium bicarbonate solution and EtOAc. The organic portion was washed with sodium bicarbonate solution (2×50 ml) and concentrated in vacuo. The resulting oil was dissolved in MeOH and purified by chromatography on silica eluting with 0-10% MeOH in DCM. The fractions were combined and the solvent removed in vacuo. The resulting solid was recrystallised from EtOAc (50 ml) to afford the title compound;

LC-MS: Rt 0.85 mins; MS m/z 567.4 {M+H}+; Method 2minLC_v003

1H NMR (400 MHz, d6-DMSO) δ 10.3 (1H, s), 9.4 (1H, d), 8.9 (1H, t), 8.6 (1H, s), 8.2 (1H, d), 8.1 (1H, s), 7.8 (1H, m), 7.4 (1H, d), 7.35 (1H, d), 7.2 (2H, m), 7.1 (1H, d), 7.0 (1H, t), 4.6 (1H, d), 2.9 (4H, m), 2.4 (3H, t), 2.2 (3H, s).

Step 2: N-(2-Fluoro-5-(2-(4-methylpiperazin-1-yl)benzylcarbamoyl)phenyl)-7-(1-methyl-1H-pyrazol-5-yl)imidazo[1,2-a]pyridine-3-carboxamide A mixture comprising 7-bromo-N-(2-fluoro-5-(2-(4-methylpiperazin-1-yl)benzyl carbamoyl)phenyl)imidazo[1,2-a]pyridine-3-carboxamide (step 1) (120 mg, 0.212 mmol), 1-methyl-5-(4,4,5,5-tetramethyl-1,3,2-dioxaborolan-2-yl)-1H-pyrazole (44.2 mg, 0.212 mmol), cesium carbonate (69.1 mg, 0.212 mmol) and PdCl₂(dppf).CH₂Cl₂ adduct (17.33 mg, 0.021 mmol) in DMF (5 ml) under N₂ was heated at 85° C. for 2 hrs. After cooling to RT, the reaction mixture was partitioned between with EtOAc and water. A precipitate formed which was removed by filtration and discuarded. The organic portion was separated and washed with NaHCO₃, water, dried (MgSO₄) and concentrated in vacuo. The crude product was purified by chromatography on silica eluting with 0-20% MeOH/DCM and the product fractions were combined and concentrated in vacuo. The product was dissolved in MeOH and passed through a 1 g 2,4,6-trimercaptotriazine silica column under gravity. The column was washed with MeOH and the combined eluents were concentrated in vacuo. The product was triturated with THF (1% MeOH) followed by ether to afford the title compound;

LC-MS: Rt 0.80 mins; MS m/z 567 {M+H}+; Method 2minLC_v003

1H NMR (400 MHz, MeOD) δ 9.6 (1H, s), 8.6 (1H, s), 8.4 (1H, m), 7.9 (1H, s), 7.8 (1H, m), 7.6 (1H, s), 7.45-7.3 (5H, m), 7.2 (1H, m), 6.7 (1H, s), 4.75 (2H, s), 4.1 (3H, s), 3.4 (4H, s broad), 3.2 (4H, s broad), 2.95 (3H, s).

Example 1.2

7-(3-Fluoro-4-(2-hydroxyethylcarbamoyl)phenyl)-N-(2-fluoro-5-(2-(4-methylpiperazin-1-yl)benzylcarbamoyl)phenyl)imidazo[1,2-a]pyridine-3-carboxamide

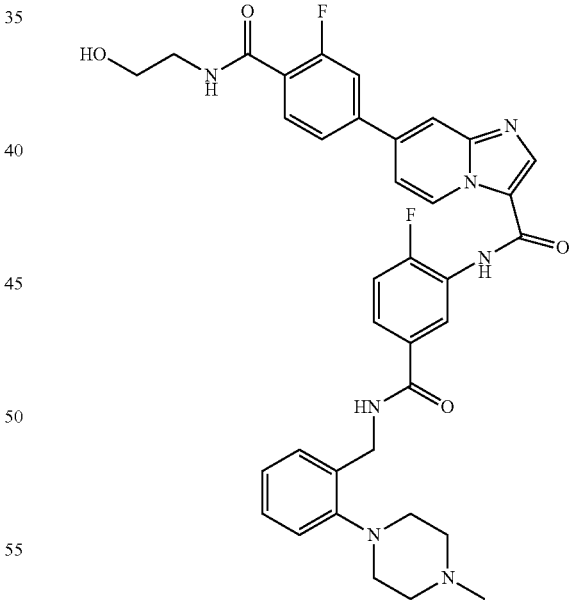

A mixture comprising 7-bromo-N-(2-fluoro-5-(2-(4-methylpiperazin-1-yl)benzylcarbamoyl)phenyl)imidazo[1,2-a]pyridine-3-carboxamide (Ex 1.1, step 1) (120 mg, 0.212 mmol), 3-fluoro-4-(2-hydroxyethylcarbamoyl)phenylboronic acid (48.2 mg, 0.212 mmol), cesium carbonate (69.1 mg, 0.212 mmol) and PdCl₂(dppf).CH₂Cl₂ adduct (17.33 mg, 0.021 mmol) in DMF (3 ml) under N₂ was heated at 85° C. for 2 hrs. Further portions of 3-fluoro-4-(2-hydroxyethylcarbamoyl)phenylboronic acid (48.2 mg, 0.212 mmol), cesium carbonate (69.1 mg, 0.212 mmol) and PdCl$_2$(dppf).CH$_2$Cl$_2$ adduct (17.33 mg, 0.021 mmol) were added and heating continued at 100° C. overnight. The reaction mixture was diluted with EtOAc and water and the biphasic mixture was filtered. The filtercake was washed with MeOH and the filtrate was concentrated under vacuum. Purification of the crude residue by chromatography on silica eluting with 0-20% NH$_3$ MeOH/DCM afforded a beige solid. The solid was triturated with THF/ether and dried in vacuo at 45° C. overnight to afford the title compound;

LC-MS: Rt 0.81 mins; MS m/z 668/669 {M+H}+; Method 2minLC_v003 av55463 1H NMR (400 MHz, CD3OD) δ 9.6 (1H, s), 8.6 (1H, s), 8.4 (1H, d), 8.1 (1H, s), 8.0 (1H, t), 7.8 (3H, m), 7.6 (1H, d), 7.5-7.2 (4H, m), 7.2 (1H, t), 4.7 (2H, s), 3.75 (2H, t), 3.6 (2H, t), 3.1 (4H, s broad), 3.0 (4H, s broad), 2.6 (3H, s).

Example 1.3(i) and 1.3(ii)

Step1: Example 1.3 (i): 7-Bromo-N-(2-methyl-5-(2-(4-methylpiperazin-1-yl)benzylcarbamoyl)phenyl)imidazo[1,2-a]pyridine-3-carboxamide

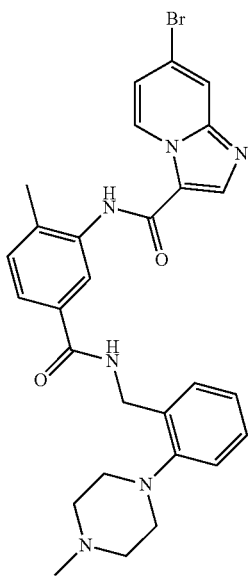 [SMILES: Cc1ccc(C(=O)NCc2ccccc2N2CCN(C)CC2)cc1NC(=O)c1cnc2cc(Br)ccn12]

Methyl 3-(7-bromoimidazo[1,2-a]pyridine-3-carboxamido)-4-methylbenzoate (Intermediate 1B)(400 mg, 1.030 mmol) and TBD (143 mg, 1.030 mmol) in toluene (10 ml) was treated with (2-(4-methylpiperazin-1-yl)phenyl)methanamine (212 mg, 1.030 mmol) and heated at 100° C. under nitrogen overnight. Further TBD (106 mg, 0.82 mmol) was added the mixture was heated at 100° C. for a further 24 hrs. The solvent was removed in vacuo and the residue was partitioned between EtOAc (50 ml) and sodium bicarbonate solution (50 ml). The organic portion was separated and washed with sodium bicarbonate (2×25 ml), dried (MgSO$_4$), filtered and evaporated to dryness to give a yellow solid. Purification by chromatography on silica eluting with 0-20% 2M NH$_3$ in MeOH/DCM afforded a colourless oil. The oil was dissolved in minimum volume of EtOAc and triturated iso-hexane to afford the title compound as a white solid;

LC-MS: Rt 0.85 mins; MS m/z 561.4 {M+H}+; Method 2minLC_v003

1H NMR (400 MHz, DMSO-d6) δ 10.1 (s, 1H), 9.4 (d, 1H), 8.9 (t, 1H), 8.5 (s, 1H), 8.1 (s, 1H), 7.9 (s, 1H), 7.7 (d, 1H), 7.4 (d, 1H), 7.3 (d, 1H), 7.2 (m, 2H), 7.1 (d, 1H), 7.0 (m, 1H), 4.6 (d, 2H), 3.1 (t, 4H), 2.4 (s, 3H), 2.3 (s, 3H)

Step 2 Example 1.3 (ii): 7-(1-Methyl-1H-pyrazol-5-yl)-N-(2-methyl-5-(2-(4-methylpiperazin-1-yl)benzylcarbamoyl)phenyl)imidazo[1,2-a]pyridine-3-carboxamide

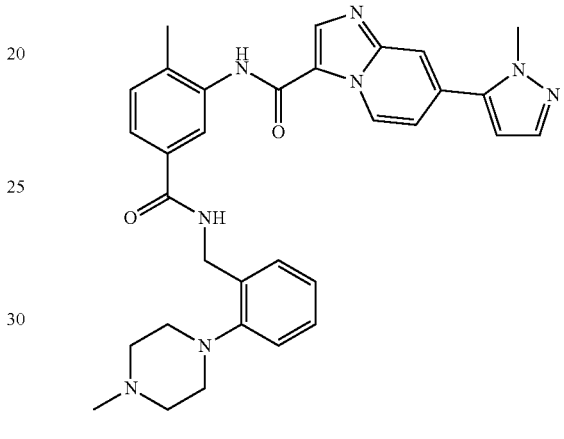

Under nitrogen, a mixture comprising 7-bromo-N-(2-methyl-5-(2-(4-methylpiperazin-1-yl)benzylcarbamoyl)phenyl)imidazo[1,2-a]pyridine-3-carboxamide (step 1) (77.8 mg, 0.125 mmol), 1-methyl-5-(4,4,5,5-tetramethyl-1,3,2-dioxaborolan-2-yl)-1H-pyrazole (51.9 mg, 0.249 mmol) and cesium carbonate (40.6 mg, 0.125 mmol) in DMF (1 ml) was treated with PdCl$_2$(dppf).CH$_2$Cl$_2$ adduct (50.9 mg, 0.062 mmol) and heated at 110° C. for 1 hr. The solvent was removed in vacuo and purification by chromatography on silica eluting with 0-20% 2M NH$_3$ in MeOH/DCM afforded a black solid. The solid was dissolved in 7M NH$_3$ in MeOH (12 ml) and passed through a 1 g Pd scavenger cartridge. The solvent was removed in vacuo and the resulting solid was dried to yield the title compound;

LC-MS: Rt 0.98 mins; MS m/z 563.5 {M+H}+; Method 2minLC_v003 av55760 1H NMR (400 MHz, MeOD) δ 9.5 (1H, d), 8.55 (1H, s), 8.0 (1H, s), 7.8 (1H, s), 7.7 (1H, dd), 7.55 (1H, s), 7.4 (2H, m), 7.2 (3H, m), 7.1 (1H, t), 6.6 (1H, d), 4.7 (2H, t), 4.0 (3H, s), 3.1 (7H, b), 2.7 (4H, s), 2.4 (3H, s)

Example 1.4

N-(2-Fluoro-5-(2-(4-methylpiperazin-1-yl)benzyl-carbamoyl)phenyl)-7-(pyridine-3-yl)imidazo[1,2-a]pyridine-3-carboxamide

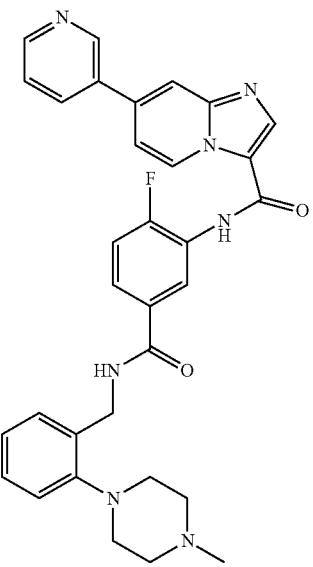 [SMILES: CN1CCN(c2ccccc2CNC(=O)c2ccc(F)c(NC(=O)c3cnc4cc(-c5cccnc5)ccn34)c2)CC1]

Under nitrogen, 7-bromo-N-(2-fluoro-5-(2-(4-methylpiperazin-1-yl)benzylcarbamoyl)phenyl)imidazo[1,2-a]pyridine-3-carboxamide (Ex 1.1, step 1) (120 mg, 0.212 mmol), pyridine-3-ylboronic acid (33.8 mg, 0.212 mmol), triethylamine (0.030 ml, 0.212 mmol), cesium carbonate (69.1 mg, 0.212 mmol) and PdCl$_2$(dppf).CH$_2$Cl$_2$ adduct (17.33 mg, 0.021 mmol) in DMF (3 ml) were heated at 85° C. overnight. A further portion of cesium carbonate (24.34 mg, 0.075 mmol) and PdCl$_2$(dppf).CH$_2$Cl$_2$ adduct (6.10 mg, 7.47 μmol) were added along with 3-(1,3,2-dioxaborinan-2-yl)pyridine (34.6 mg, 0.212 mmol) and heated continued at 85° C. for 26 hrs. A further portion of cesium carbonate (24.34 mg, 0.075 mmol) and PdCl$_2$(dppf).CH$_2$Cl$_2$ adduct (6.10 mg, 7.47 μmol) and 3-(1,3,2-dioxaborinan-2-yl)pyridine (34.6 mg, 0.212 mmol) were added. The reaction was heated at 100° C. for 2 hrs. The reaction mixture was diluted with EtOAc and water and the resulting product which precipitated out was collected by filtration. Further product was contained in the organic phase, which was washed with sat. NaHCO$_3$, brine, dried (MgSO$_4$) and concentrated in vacuo. The crude residue was combined with the precipitated product and purified by chromatography on silica eluting with 0-20% MeOH/DCM. The resulting solid was purified by preparative LC-MS eluting with 0.1% diethylamine 30-70% acetonitrile/water. The product fractions were partitioned between EtOAc and NaHCO$_3$. The organic portion was separated, dried (MgSO$_4$) and concentrated in vacuo to afford the title compound;

LC-MS: Rt 1.79/1.81 mins; MS m/z 564/565 {M+H}+; Method 10minLC_v003

1H NMR (400 MHz, CD$_3$OD) δ 9.7 (1H, d), 9.1 (1H, d), 8.7 (1H, m), 8.6 (1H, s), 8.4 (1H, m), 8.3 (1H, m), 8.2 (1H, s), 8.1 (1H, s), 7.8 (1H, m), 7.7-7.5 (2H, m), 7.4-7.1 (5H, m), 4.3 (2H, s), 3.1 (4H, m), 2.8 (4H, s broad), 2.5 (3H, t).

Example 1.5

N-(2-Fluoro-5-(2-(4-methylpiperazin-1-yl)benzyl-carbamoyl)phenyl)-7-(1-methyl-1H-pyrazol-4-yl)imidazo[1,2-a]pyridine-3-carboxamide hydrochloride

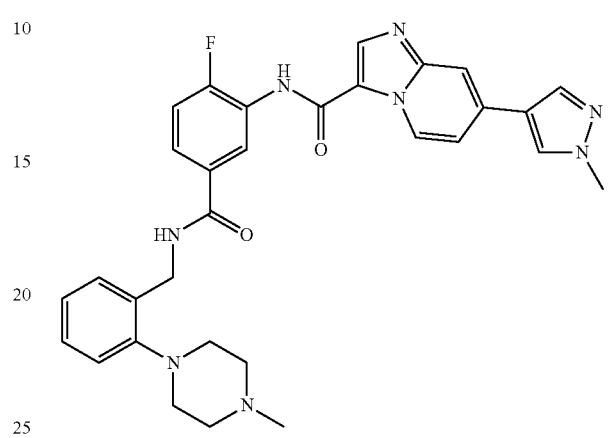

Step 1: N-(2-Fluoro-5-(2-(4-methylpiperazin-1-yl)benzylcarbamoyl)phenyl)-7-(1-methyl-1H-pyrazol-4-yl)imidazo[1,2-a]pyridine-3-carboxamide A mixture comprising 7-bromo-N-(2-fluoro-5-(2-(4-methylpiperazin-1-yl)benzylcarbamoyl)phenyl)imidazo[1,2-a]pyridine-3-carboxamide (Ex 1.1, step 1) (100 mg, 0.177 mmol) and cesium carbonate (230 mg, 0.707 mmol) in DME (2.5 ml) and water (1 ml) under nitrogen was treated with 1-methyl-4-(4,4,5,5-tetramethyl-1,3,2-dioxaborolan-2-yl)-1H-pyrazole followed by PdCl$_2$(dppf).CH$_2$Cl$_2$ adduct (7.22 mg, 8.84 μmol) and heated using microwave radiation at 100° C. for 1 hr. After cooling to RT, the reaction mixture was partitioned between water (4 ml) and EtOAc (10 ml)/MeOH (1 ml). The organic portion was separated, dried (MgSO$_4$) and concentrated in vacuo. Puriifcation by chromatography on silica eluting with 0-20% MeOH in DCM followed by trituration of the resulting solid with EtOAc afforded the title compound;

LC-MS: Rt 0.89 mins; MS m/z 567 {M+H}+; Method 2minLC_v003

Step 2: N-(2-Fluoro-5-(2-(4-methylpiperazin-1-yl)benzylcarbamoyl)phenyl)-7-(1-methyl-1H-pyrazol-4-yl)imidazo[1,2-a]pyridine-3-carboxamide hydrochloride N-(2-Fluoro-5-(2-(4-methylpiperazin-1-yl)benzylcarbamoyl)phenyl)-7-(1-methyl-1H-pyrazol-4-yl)imidazo[1,2-a]pyridine-3-carboxamide (step 1) (30 mg, 0.053 mmol) in MeOH (2 ml) was treated with HCl in ether (0.053 ml, 0.053 mmol) and the solution was evaporated to dryness and dried in vacuo overnight to afford the title compound;

LC-MS: Rt 0.82 mins; MS m/z 56, [M+H]+; Method 2minLC_v003

The compounds of the following tabulated Examples (Table 1) were prepared by a similar methods to that of Example 1.1-1.5 from the appropriate starting compounds, the preparations of which are detailed in the 'Preparation of Intermediates' section.

TABLE 1

| Ex. | Structure Name | [M + H]+/NMR |
|---|---|---|
| 1.6 | 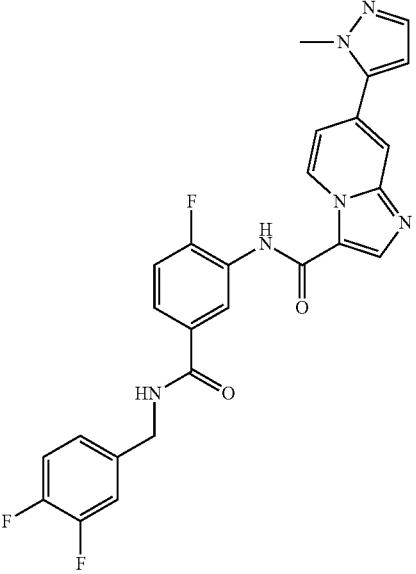 [SMILES: Cn1nccc1-c1ccn2c(C(=O)Nc3cc(C(=O)NCc4ccc(F)c(F)c4)ccc3F)cnc2c1]<br>N-(5-(3,4-difluorobenzylcarbamoyl)-2-fluorophenyl)-7-(1-methyl-1H-pyrazol-5-yl)imidazo[1,2-a]pyridine-3-carboxamide | Rt = 3.16 mins; MS m/z 505.4 [M + H]+; Method 10 minLC_v003<br>1H NMR (400 MHz, DMSO) δ 10.35 (1H, s), 9.50 (1H, d), 9.17 (1H, t), 8.68 (1H, s), 8.19 (1H, d), 8.00 (1H, s), 7.75 (1H, m), 7.56 (1H, s), 7.42-7.50 (3H, m), 7.18 (1H, m), 4.48 (2H, d), 4.01 (3H, s). |
| 1.7 | 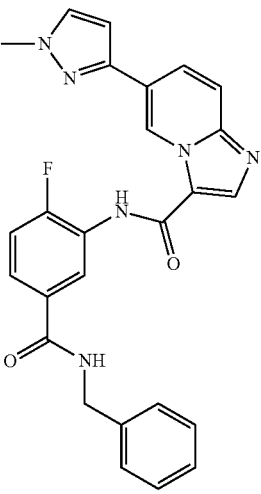 [SMILES: Cn1ccc(-c2ccc3ncc(C(=O)Nc4cc(C(=O)NCc5ccccc5)ccc4F)n3c2)n1]<br>N-(5-(benzylcarbamoyl)-2-fluorophenyl)-6-(1-methyl-1H-pyrazol-3-yl)imidazo[1,2-a]pyridine-3-carboxamide | Rt 0.93 mins; MS m/z 469/470/471 {M + H}+; Method 2 minLC_v003<br>1H NMR (400 MHz, DMSO-d6) δ10.3 (1H, s), 10.0 (1H, s), 9.1 (1H, t), 8.6 (1H, s), 8.2 (1H, m), 7.9 (1H, d), 7.8 (3H, m), 7.5 (1H, t), 7.35 (4H, m), 7.3 (1H, m), 6.7 (1H, s), 4.5 (2H, d), 3.9 (3H, s). |

TABLE 1-continued

| Ex. | Structure Name | [M + H]⁺/NMR |
|---|---|---|
| 1.8 | 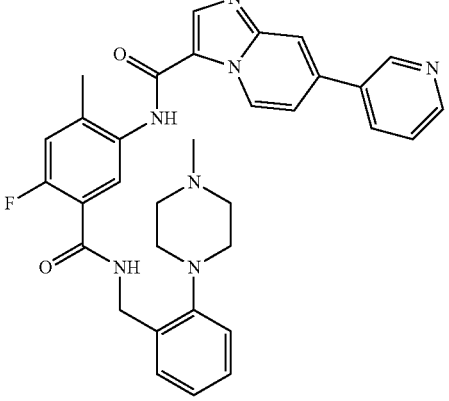<br>N-(4-fluoro-2-methyl-5-(2-(4-methylpiperazin-1-yl)benzylcarbamoyl)phenyl)-7-(pyridine-3-yl)imidazo[1,2-a]pyridine-3-carboxamide | Rt = 0.78 mins; MS m/z 578.5 [M + H]+; Method 2 minLC_v003<br>1H NMR (400 MHz, DMSO) δ 9.60 (1H, s), 8.93 (1H, s), 8.62 (1H, d), 8.49 (1H, s), 8.18 (1H, d), 7.98 (1H, s), 7.87 (1H, d), 7.57 (3H, m), 7.42 (1H, d), 7.36 (1H, d), 7.30 (1H, dd), 7.22 (1H, d), 7.13 (2H, m), 4.73 (2H, d), 3.05 (4H, m), 2.90-2.75 (4H, m), 2.48 (3H, s), 2.39 (3H, s). |
| 1.9 | 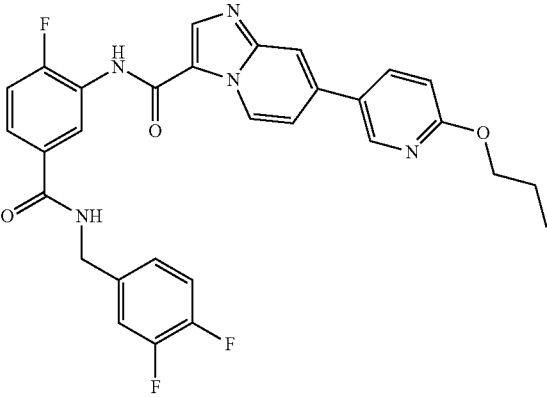<br>N-(5-(3,4-difluorobenzylcarbamoyl)-2-fluorophenyl)-7-(6-(3-(dimethylamino)propoxy)pyridine-3-yl)imidazo[1,2-a]pyridine-3-carboxamide | Rt 0.92 mins; MS m/z 603.6 {M + H}+; Method 2 minLC_v003<br>1H NMR (400 MHz, MeOD) δ 9.6 (1H, s), 8.6 (1H, d), 8.5 (1H, s), 8.4 (1H, dd), 8.2 (1H, dd), 8.0 (1H, s), 7.8 (1H, m), 7.5 (1H, d), 7.4 (1H, d), 4.3 (3H, m), 7.0 (1H, d), 4.6 (2H, s), 4.5 (2H, d), 2.6 (2H, t), 2.3 (6H, s), 2.0 (2H, m) |
| 1.10 | 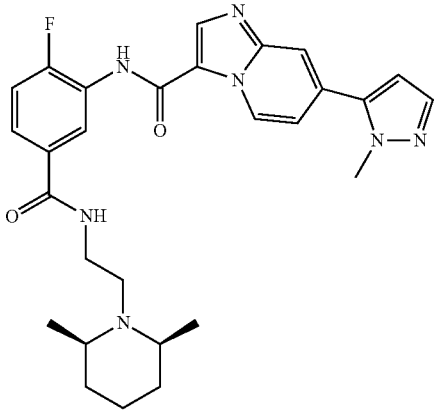 [SMILES: C[C@@H]1CCC[C@H](C)N1CCNC(=O)c1ccc(F)c(NC(=O)c2cnc3cc(-c4ccnn4C)ccn23)c1]<br>N-(5-(2-(2,6-cis-dimethylpiperidin-1-yl)ethylcarbamoyl)-2-fluorophenyl)-7-(1-methyl-1H-pyrazol-5-yl)imidazo[1,2-a]pyridine-3-carboxamide | Rt 1.91 mins; MS m/z 518.40 [M + H]+; Method 10 minLC_v003<br>1H NMR (400 MHz, DMSO-d6) δ 10.7 (1H, s), 10.0 (1/2H, m), 9.5 (1H, d), 9 (1H, t), 8.8 (1H, s), 8.2 (1H, m) 8.1 (1H, s), 7.6 (1H, s), 7.5 (2H, d), 6.6 (1H, s) 4 (3H, s), 3.6 (2H, m), 3.4 (2H, m), 3.3 (2H, m), 3.1 (1H, m), 1.9 (1H, m), 1.6 (2H, m), 1.5 (2H, m), 1.4 (4H, d), 1.3 (2H, d) |

TABLE 1-continued

| Ex. | Structure Name | [M + H]+/NMR |
|---|---|---|
| 1.11 | 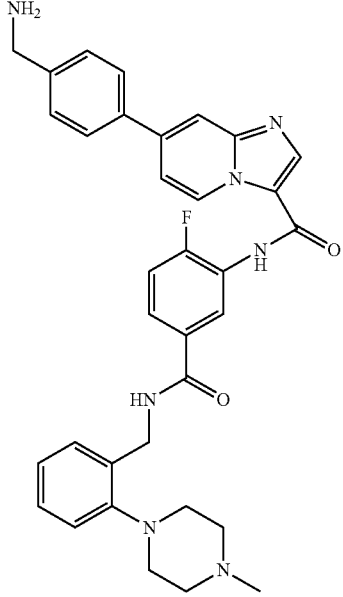 [SMILES: CN1CCN(c2ccccc2CNC(=O)c2ccc(F)c(NC(=O)c3cnc4cc(-c5ccc(CN)cc5)ccn34)c2)CC1]<br>7-(4-(aminomethyl)phenyl)-N-(2-fluoro-5-(2-(4-methylpiperazin-1-yl)benzylcarbamoyl)phenyl)imidazo[1,2-a]pyridine-3-carboxamide | Rt 0.83 mins; MS m/z 592 {M + H}+; Method 2 minLC_v003<br>1H NMR (400 MHz, DMSO-d6) δ10.3 (broad 1H, s), 9.5 (1H, d), 9.0 (1H, t), 8.7 (1H, s), 8.25 (1H, d), 8.1 (1H, s), 7.9 (2H, d), 7.6 (1H, d), 7.5-7.4 (3H, m), 7.25-7.2 (2H, m), 7.15 (1H, d), 7.1 (1H, t), 4.6 (2H, d), 3.8 (2H, s), 2.9 (4H, s), 2.5 (4H, s), 2.25 (3H, s), 2.1 (2H, s broad). |
| 1.12 | 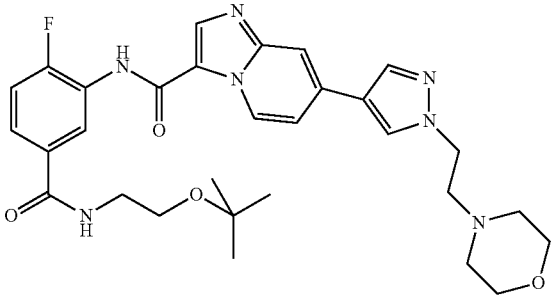 [SMILES: CC(C)(C)OCCNC(=O)c1ccc(F)c(NC(=O)c2cnc3cc(-c4cnn(CCN5CCOCC5)c4)ccn23)c1]<br>N-(5-(2-tert-butoxyethylcarbamoyl)-2-fluorophenyl)-7-(1-(2-morpholinoethyl)-1H-pyrazol-4-yl)imidazo[1,2-a]pyridine-3-carboxamide | Rt = 0.83 mins; MS m/z 578.5, [M + H]+; Method 2 minLC_v003<br>1H NMR (400 MHz, DMSO) δ 10.25 (1H, s), 9.35 (1H, d), 8.60-8.43 (2H, m), 8.15 (2H, s), 7.97 (1H, s), 7.77 (1H, m), 7.60-7.35 (3H, m), 4.28 (2H, m), 3.55 (4H, m), 3.40 (2H, m), 2.50-2.80 (8H, m), 1.00-1.21 (9H, m). |
| 1.13 | 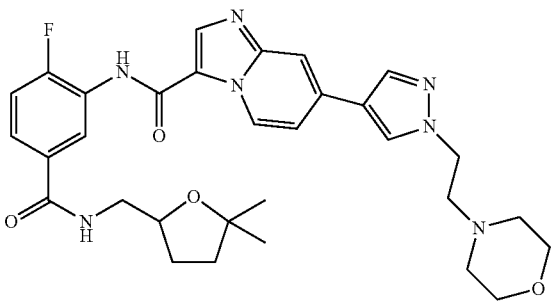 [SMILES: CC1(C)CCC(CNC(=O)c2ccc(F)c(NC(=O)c3cnc4cc(-c5cnn(CCN6CCOCC6)c5)ccn34)c2)O1]<br>N-(5-((5,5-dimethyltetrahydrofuran-2-yl)methylcarbamoyl)-2-fluorophenyl)-7-(1-(2-morpholinoethyl)-1H-pyrazol-4-yl)imidazo[1,2-a]pyridine-3-carboxamide | Rt = 0.96 mins; MS m/z 590.5, [M + H]+; Method 2 minLC_v003<br>1H NMR (400 MHz, DMSO) δ 10.20 (1H, s), 9.38 (1H, d), 8.61 (2H, m), 8.45 (2H, s), 8.16 (2H, m), 7.98 (1H, s), 7.79 (1H, m), 7.48-7.37 (2H, m), 4.28 (2H, t), 4.07 (1H, m), 3.57 (4H, m), 2.76 (2H, t), 2.52 (2H, m), 2.45 (4H, m), 2.02 (1H, m), 1.70 (3H, m), 1.21 (3H, s), 1.17 (3H, s). |

TABLE 1-continued

| Ex. | Structure Name | [M + H]⁺/NMR |
|---|---|---|
| 1.14 | 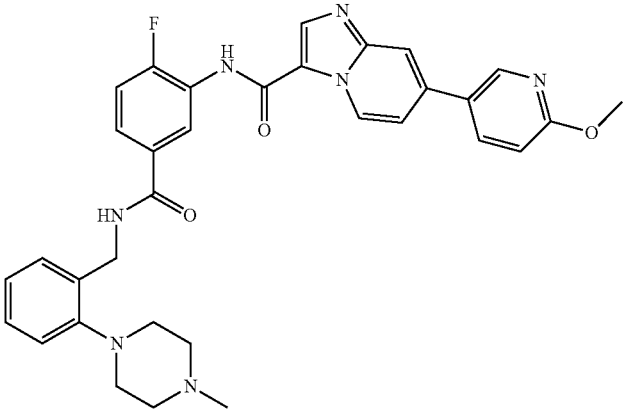 [SMILES: COc1ccc(-c2ccn3c(C(=O)Nc4cc(C(=O)NCc5ccccc5N5CCN(C)CC5)ccc4F)cnc3c2)cn1]<br>N-(2-fluoro-5-(2-(4-methylpiperazin-1-yl)benzylcarbamoyl)phenyl)-7-(6-methoxy-pyridine-3-yl)imidazo[1,2-a]pyridine-3-carboxamide | Rt = 1.03 mins; MS m/z 594.4, [M + H]+; Method 2 minLC_v003<br>1H NMR (400 MHz, DMSO) δ 10.30(1H, s), 9.50 (1H, d), 8.99 (1H, t), 8.76 (1H, s), 8.65 (1H, s), 8.30 (1H, d), 8.23 (1H, d), 8.17 (1H, s), 7.85 (1H, m), 7.63 (1H, d), 7.52-7.36 (3H, m), 7.27 (1H, m), 7.05 (2H, m), 4.58 (2H, d), 3.32 (3H, s), 2.87 (4H, m), 2.52 (4H, m), 2.23 (3H, s). |
| 1.15 | 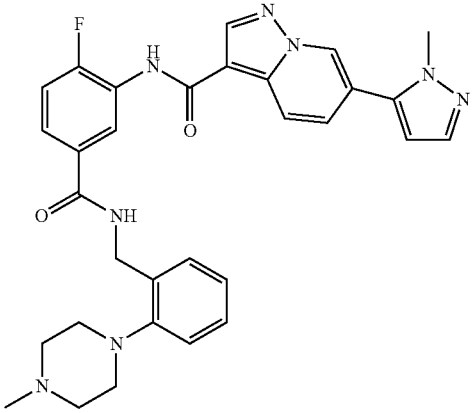 [SMILES: CN1CCN(c2ccccc2CNC(=O)c2ccc(F)c(NC(=O)c3cnn4cc(-c5ccnn5C)ccc34)c2)CC1]<br>N-(2-fluoro-5-(2-(4-methylpiperazin-1-yl)benzylcarbamoyl)phenyl)-6-(1-methyl-1H-pyrazol-5-yl)pyrazolo[1,5-a]pyridine-3-carboxamide | Rt 0.89 mins; MS m/z 567/568/569 {M + H}+; Method 2 minLC_v003<br>1H NMR (400 MHz, DMSO-d6) δ 10.0 (1H, s), 9.9 (1H, m), 9.1 (1H, s), 9.0 (1H, t), 8.9 (1H, s), 8.3 (2H, m), 7.8 (1H, m), 7.7 (1H, d), 7.55 (1H, s), 7.4 (1H, t), 7.3 (2H, m), 7.2 (2H, m), 6.6 (1H, s), 4.6 (2H, d), 4.0 (3H, s), 3.6-3.0 (8H, m), 2.9 (3H, d). |
| 1.16 | 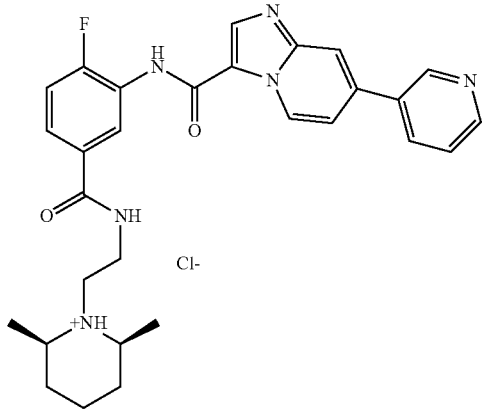 [SMILES: C[C@@H]1CCC[C@H](C)[NH+]1CCNC(=O)c1ccc(F)c(NC(=O)c2cnc3cc(-c4cccnc4)ccn23)c1 ; [Cl-]]<br>1-(2-(4-fluoro-3-(7-(pyridine-3-yl)imidazo[1,2-a]pyridine-3-carboxamido)benzamido)ethyl)-2,6-cis-dimethylpiperidinium chloride | Rt 0.70 mins; MS m/z 515{M + H}+; Method 2 minLC_v003<br>1H NMR (400 MHz, DMSO) δ 10.71 (1H, s), 10.01 (1H, t), 9.72 (1H, d), 9.33 (1H, s), 9.05 (1H, m), 8.90 (1H, s), 8.85 (1H, d), 8.70 (1H, m), 8.47 (1H, s), 8.23 (1H, m), 7.89 (3H, m), 7.51 (1H, m), 3.55 (2H, m), 3.50-3.33 (2H, m), 1.83 (1H, m), 1.70 (2H, m), 1.50 (2H, m), 1.40 and 1.30 (6H, 2 × d). |

TABLE 1-continued

| Ex. | Structure Name | [M + H]⁺/NMR |
|---|---|---|
| 1.17 | 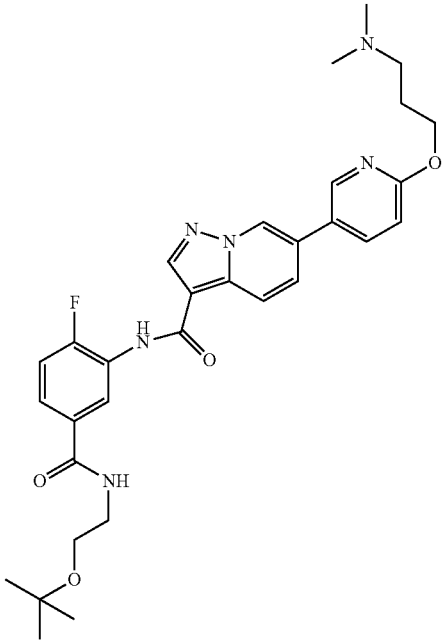 [SMILES: CN(C)CCCOc1ccc(-c2ccc3c(C(=O)Nc4cc(C(=O)NCCOC(C)(C)C)ccc4F)cnn3c2)cn1]<br>N-(5-(2-tert-butoxyethylcarbamoyl)-2-fluorophenyl)-6-(6-(3-(dimethylamino)propoxy)pyridine-3-yl)pyrazolo[1,5-a]pyridine-3-carboxamide | Rt 0.92 mins; MS m/z 577{M + H}+; Method 2 minLC_v003<br>1H NMR (400 MHz, MeOD) δ 9.0 (1H, s), 837 (1H, s), 8.5 (1H, d), 8.4 (1H, d), 8.3 (1H, d), 8.1 (1H, dd), 7.85 (1H, d), 7.75 (1H, m), 7.35 (1H, t), 6.95 (1H, d), 4.4 (2H, t), 3.6 (2H, m), 3.5 (2H, m), 2.6 (2H, t), 2.3 (6H, s), 2.0 (2H, m), 1.25 (9H, s) |
| 1.18 | 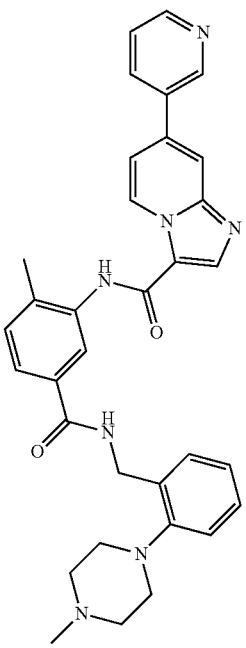 [SMILES: Cc1ccc(C(=O)NCc2ccccc2N2CCN(C)CC2)cc1NC(=O)c1cnc2cc(-c3cccnc3)ccn12]<br>N-(2-methyl-5-(2-(4-methylpiperazin-1-yl)benzylcarbamoyl)phenyl)-7-(pyridine-3-yl)imidazo[1,2-a]pyridine-3-carboxamide | Rt 0.75 mins; MS m/z 560.5 {M + H}+; Method 2 minLC_v003<br>1H NMR (400 MHz, MeOD), δ 9.6 (1H, d), 9.0 (1H, d), 8.6 (1H, dd), 8.5 (1H, s), 8.3 (1H, d), 8.05 (1H, s), 7.95 (1H, d), 7.7 (1H, dd), 7.6 (1H, s), 7.55 (1H, dd), 7.4 (1H, d), 7.35 (1H, d), 7.25 (2H, m), 7.1 (1H, t), 4.7 (2H, s), 3.0 (4H, b), 2.8 (4H, b), 2.5 (3H, s), 2.4 (3H, s). |

| Ex. | Structure Name | [M + H]+/NMR |
|---|---|---|
| 1.19 | 1-methyl-4-(2-((6-methyl-5-(7-(1-methyl-1H-pyrazol-5-yl)imidazo[1,2-a]pyridine-3-carboxamido)nicotinamido)methyl)phenyl)piperazin-1-ium chloride | Rt 0.76 mins; MS m/z 564.5 {M + H}+; Method 2 minLC_v003 1H NMR (400 MHz, MeOD) δ 9.60 (1H, d), 8.85 (1H, d), 8.59 (1H, s), 8.40 (1H, d), 7.91 (1H, s), 7.59 (1H, d), 7.39 (2H, m), 7.30 (2H, m), 7.16 (1H, t), 6.65 (1H, d), 4.76 (2H, s), 4.04 (3H, s), 3.10 (4H, m), 2.96 (4H, b), 2.66 (3H, s), 2.59 (3H, s) |

Example 1.10

N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide

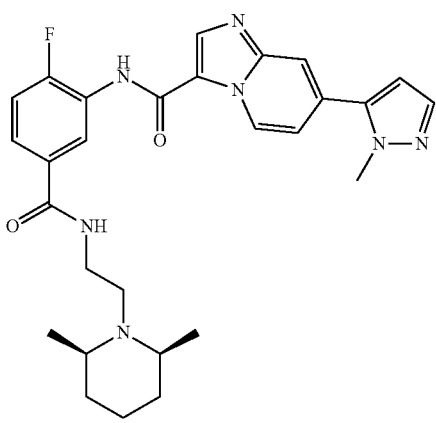 [SMILES: C[C@@H]1CCC[C@H](C)N1CCNC(=O)c1ccc(F)c(NC(=O)c2cnc3cc(-c4ccnn4C)ccn23)c1]

PdCl$_2$(dppf).CH$_2$Cl$_2$ adduct (39.5 mg, 0.048 mmol) was added to a mixture comprising 1-methyl-3-(4,4,5,5-tetramethyl-1,3,2-dioxaborolan-2-yl)-1H-pyrazole (commercially available) (212 mg, 1.017 mmol), 7-bromo-N-(5-(2-(2,6-cis-dimethylpiperidin-1-yl)ethylcarbamoyl)-2-fluorophenyl) imidazo[1,2-a]pyridine-3-carboxamide (Intermediate 4C) (500 mg, 0.968 mmol), Cs$_2$CO$_3$ (1262 mg, 3.87 mmol) in 1,2-dimethoxyethane (10 ml) and water (4.29 ml). The mixture was degassed thoroughly refilling with nitrogen (×3). The mixture was heated using microwave radiation at 100° C. for 1 hour. The water was removed by pipette and the organic portion was concentrated in vacuo. The residue was dissolved in MeOH and dry loaded onto silica. The crude product was purified by chromatography on silica eluting with 0-20% MeOH in DCM to afford the title compound. (See Table 1 for characterising data).

The citrate salt of N-(5-(2-(2,6-cis-dimethylpiperidin-1-yl)ethylcarbamoyl)-2-fluorophenyl)-7-(1-methyl-1H-pyrazol-5-yl)imidazo[1,2-a]pyridine-3-carboxamide was prepared according to the following procedure:

Step 1: 3-[(7-Bromo-imidazo[1,2-a]pyridine-3-carbonyl)-amino]-4-fluoro-benzoic acid methyl ester To the solution of compound 7-bromoimidazo[1,2-a]pyridine-3-carboxylic acid (Intermediate A step 3) (1.26 Kg, 5.23 mol) in DMAC (15 L) was added dropwise SOCl$_2$ (1.86 kg, 15.6 mol) at 10° C. in 30 min. To the resulting mixture warmed to 20° C. was added compound methyl 3-amino-4-fluorobenzoate (884 g, 5.23 mol) in DMAC (3.0 L) over 30 min. After addition, the reaction temperature went up to 30° C. HPLC showed the reaction went to completion within 5 min. To the reaction mixture was added water (20 L) over 20 min. The mixture was filtered and dried under vacuum to afford the title compound as a white solid;

$^1$H NMR (400 MHz, DMSO-d$_6$) δ 3.87 (s, 3H) 7.57 (dd, J=7.28, 2.01 Hz, 1H) 7.51 (dd, J=10.16, 8.66 Hz, 1H) 7.90 (td, J=4.33, 2.38 Hz, 1H) 8.29 (m, 2H) 8.90 (s, 1H) 9.43 (d, J=7.53 Hz, 1H) 10.78 (s, 1H) Rt 6.90 mins; MS m/z 394.0 {M+H}+; Method 10 min LC Step 2: 4-Fluoro-3-{[7-(2-methyl-2H-pyrazol-3-yl)-imidazo[1,2-a]pyridine-3-carbonyl]-amino}-benzoic acid 3-[(7-Bromo-imidazo[1,2-a]pyridine-3-carbonyl)-amino]-4-fluoro-benzoic acid methyl ester (step 1)(1200 g, 3.060 mol), 1-methyl-3-(4,4,5,5-tetramethyl-1,3,2-dioxaborolan-2-yl)-1H-pyrazole (commercially available) (764 g, 3.67 mol), PdCl$_2$(dppf).CH$_2$Cl$_2$ (75.0 g, 91.8 mmol) in dioxane (10 L) and aqueous Na$_2$CO$_3$ (2 N, 4.6 L) were heated to reflux for 6 hr. The reaction mixture was cooled to 50° C. and filtered. The filtrate was heated to reflux, to which was added AcOH (600 g, 10.0 mol) was added dropwise. During the course of addition solids came out of solution to give pale pink slurry. After addition the mixture was slowly cooled to RT and filtered. To the filter cake was added dioxane (20 L) followed by heating to reflux to obtain a solution. The solution was cooled to RT and filtered to provide the title compound as a white solid;

$^1$H NMR (400 MHz, DMSO-d$_6$) δ 4.00 (s, 3H) 6.67 (s, 1H) 7.46 (t, J=9.41 Hz, 1H) 7.40 (d, J=7.03 Hz, 1H) 7.54 (s, 1H) 7.85 (d, J=2.26 Hz, 1H) 7.99 (s, 1H) 8.28 (d, J=6.27 Hz, 1H) 8.67 (s, 1H) 9.47 (d, J=7.03 Hz, 1H) 10.35 (s, 1H).

Rt 5.40 mins; MS m/z 380.1 {M+H}+; Method 10 min LC

Step 3: 7-(2-Methyl-2H-pyrazol-3-yl)-imidazo[1,2-a]pyridine-3-carboxylic acid {5-[2-(2,6-dimethyl-piperidin-1-yl)-ethylcarbamoyl]-2-fluoro-phenyl}-amide 4-Fluoro-3-{[7-(2-methyl-2H-pyrazol-3-yl)-imidazo[1,2-a]pyridine-3-carbonyl]-amino}-benzoic acid (step 2) (450 g, 1.19 mol), EDC.HCl (454.8 g, 2.372 mol) and HOBt (181.6 g, 1.186 mol) in DMF (3.2 L) at 25° C. were stirred for 1.5 hr. The reaction was monitored by HPLC. To the reaction mixture was dropwise added cis 2-(2,6-dimethyl-piperidin-1-yl)-ethylamine (222.5 g, 1.423 mol) over 10 min and stirring continued for 30 min. To the reaction mixture was dropwise an aqueous solution of Na$_2$CO$_3$ (5%, 6 L) over 120 min and the resulting solid was collected by filtration and washed with water (5 L). To the solid was added ethanol (5 L) followed by heating to 70° C. to obtain a clear solution. Water (1.5 L) was dropwise added at 70° C. and stirred for 30 min. The clear solution was slowly cooled to 25° C. over 2 hr. The solid was filtered, washed with ethanol (500 mL) and dried under vacuum at 50° C. overnight to afford the title compound as a white solid;

$^1$H NMR (400 MHz, DMSO-d$_6$) δ 1.03-1.19 (m, 3H) 1.10 (d, J=6.02 Hz, 6H) 1.55 (br. s., 1H) 1.50 (d, J=12.30 Hz, 2H) 2.42 (br. s., 2H) 2.71 (br. s., 2H) 3.27 (d, J=5.77 Hz, 2H) 4.00 (s, 3H) 6.60 (s, 1H) 7.41 (d, J=6.02 Hz, 2H) 7.54 (s, 1H) 7.77 (s, 1H) 8.00 (s, 1H) 8.14 (d, 1H) 8.54 (s, 1H) 8.67 (s, 1H) 9.48 (d, 1H) 10.35 (s, 1H).

Rt 4.80 mins; MS m/z 518.2 {M+H}+; Method 10 min LC

Step 4: N-(5-((2-(2,6-cis-Dimethylpiperidin-1-yl)ethyl)carbamoyl)-2-fluorophenyl)-7-(1-methyl-1H-pyrazol-5-yl)imidazo[1,2-a]pyridine-3-carboxamide citric acid (1:1)

7-(2-Methyl-2H-pyrazol-3-yl)-imidazo[1,2-a]pyridine-3-carboxylic acid {5-[2-(2,6-dimethyl-piperidin-1-yl)-ethylcarbamoyl]-2-fluoro-phenyl}-amide (step 3)(480 g) was suspended in ethanol (2300 mL) in a 5000 mL four-necked flask equipped with thermometer, reflux condenser and a nitrogen inlet. The mixture was heated to 55° C. and the suspension gradually became clear. A solution of citric acid (180 g) in acetone (2.4 L) was added over 1 h and the internal temperature was controlled at 45-50° C. The clear solution was stirred at 50° C. for 2 h. A crystal seed (1 g) was added to the reactor and the internal temperature was cooled to 20° C. at a speed of 8° C./h. The mixture was stirred at 20° C. for 60 h. The resulting solid was filtered and the filter cake was washed with acetone (1 L) and dried in vacuum (under 4 mbar at 55° C.) for 24 h to afford the title compound;

$^1$H NMR (400 MHz, DMSO-d$_6$) δ 1.46 (m, 3H) 1.29 (d, J=6.02 Hz, 6H) 1.65 (s., 1H) 1.73 (d, 2H) 2.59 (m, 4H) 3.18 (m, 4H) 3.53 (d, 2H) 4.00 (s, 3H) 6.68 (s, 1H) 7.41 (d, 1H) 7.48 (d, 1H) 7.54 (s, 1H) 7.80 (s, 1H) 8.00 (s, 1H) 8.20 (d, 1H) 8.68 (s, 1H) 8.90 (s, 1H) 9.48 (d, 1H) 10.36 (s, 1H).

Example 1.20

7-(1-Methyl-1H-pyrazol-4-yl)-imidazo[1,2-a]pyridine-3-carboxylic acid {5-[2-(2,6-cis-dimethyl-piperidin-1-yl)-ethylcarbamoyl]-2-fluoro-phenyl}-amide hydrochloride

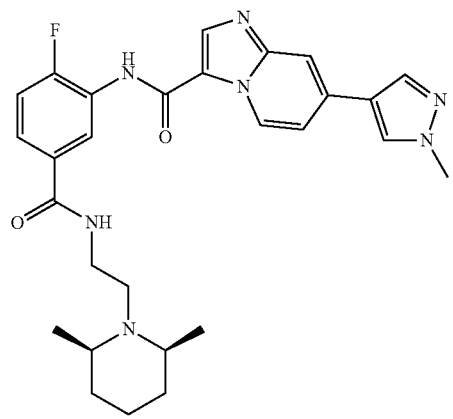 [SMILES: C[C@@H]1CCC[C@H](C)N1CCNC(=O)c1ccc(F)c(NC(=O)c2cnc3cc(-c4cnn(C)c4)ccn23)c1]

7-Bromo-N-(5-(2-(2,6-cis-dimethylpiperidin-1-yl)ethylcarbamoyl)-2-fluorophenyl) imidazo[1,2-a]pyridine-3-carboxamide (Intermediate 4C) (50 mg, 0.097 mmol), 1-methyl-1H-pyrazol-4-ylboronic acid (24.38 mg, 0.194 mmol) and cesium carbonate (126 mg, 0.387 mmol) was dissolved in DME (215 μl)/water (108 μl) to form a solution. Nitrogen was bubbled though the reaction mixture for 2 minutes. PdCl$_2$(dppf).CH$_2$Cl$_2$ adduct (3.95 mg, 4.84 μmol) was added and the mixture was heated using microwave radiation at 100° C. for 15 mins. The water was removed and the organic portion was dry loaded onto silica. The crude product was purified by chromatography on silica eluting with 0-20% 2M NH$_3$ in MeOH and the product fractions were combined and concentrated in vacuo. The product was dissolved in MeOH and passed through a 1 g 2,4,6-trimercaptotriazine silica. The solvent was removed in vacuo and the residue was triturated with ether. The resulting precipitate was filtered and dried in the oven to afford the title compound;

LC-MS: Rt 0.30 mins; MS m/z 517{M+H}+; Method 2minLC_v003

1H NMR (400 MHz, DMSO) δ 10.4 (1H, s), 10 (1H, d), 9.4 (1H, d), 8.9 (1H, t), 8.7 (1H, s), 8.55 (1H, s), 8.2 (2H, d), 8 (1H, s), 7.85 (1H, m), 7.6 (1H, d), 7.5 (1H, t), 4.2 (2H, q), 3.55 (2H, m), 3.4 (4H, m), 3.3 (2H, m), 3.1 (1H, m) 1.9 (1H, d), 1.7 (2H, m), 1.5 (2H, m), 1.4 (4H, m), 1.3 (2H, d), 1.1 (1H t).

Example 1.21

6-(1-Methyl-1H-pyrazol-5-yl)-N-(2-methyl-5-(2-(4-methylpiperazin-1-yl)benzylcarbamoyl)pyridin-3-yl)pyrazolo[1,5-a]pyridine-3-carboxamide

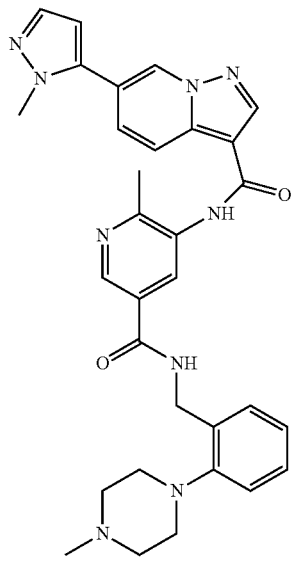 [SMILES: Cc1ncc(C(=O)NCc2ccccc2N2CCN(C)CC2)cc1NC(=O)c1cnn2cc(-c3ccnn3C)ccc12]

The title compound was prepared from Intermediate 1D and (2-(4-methylpiperazin-1-yl)phenyl)methanamine analogously to Example 1.1 step 1;

LC-MS: Rt 0.66 mins; MS m/z 564.7{M+H}+; Method 2minLowpH

Example 2.1

N-(5-(2-tert-Butoxyethylcarbamoyl)-2-fluorophenyl)-7-(6-(3-(dimethylamino)propoxy)pyridin-3-yl)imidazo[1,2-a]pyridine-3-carboxamide

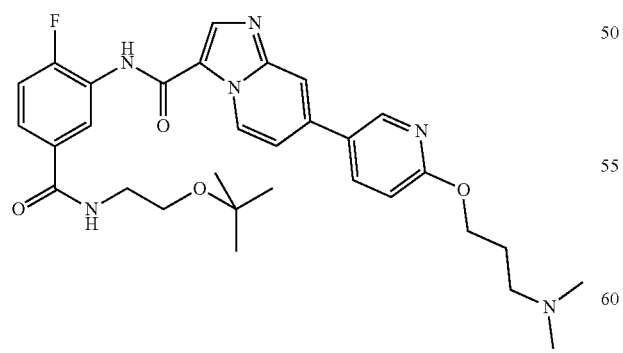

7-Bromo-N-(5-(2-tert-butoxyethylcarbamoyl)-2-fluorophenyl)imidazo[1,2-a]pyridine-3-carboxamide (Intermediate 2A) (300 mg, 0.629 mmol), N,N-dimethyl-3-(5-(4,4,5,5-tetramethyl-1,3,2-dioxaborolan-2-yl)pyridin-2-yloxy)propan-1-amine (202 mg, 0.660 mmol) and cesium carbonate (819 mg, 2.51 mmol) were combined in 1,2-dimethoxyethane (7 ml) and water (3 ml). The mixture was degassed thoroughly refilling with nitrogen and treated with PdCl$_2$(dppf).CH$_2$Cl$_2$ adduct (25.7 mg, 0.031 mmol). The mixture was once again degassed thoroughly refilling with nitrogen and heated using microwave radiation at 100° C. for 1 hr. The aqueous was removed by pipette and the organic portion was absorbed onto silica and purified by chromatography eluting with 0-20% MeOH in DCM. The resulting solid was recrystallised from EtOAc to afford the title compound;

LC-MS: Rt 2.55 mins; MS m/z 577.5, [M+H]+; Method 10minLC_v003

1H NMR (400 MHz, DMSO) δ 10.25 (1H, s), 9.46 (1H, d), 8.73 (1H, s), 8.65 (1H, s), 8.55 (1H, t), 8.24 (1H, d), 8.16 (2H, m), 7.80 (1H, m), 7.63 (1H, d), 7.45 (1H, t), 6.95 (1H, d), 4.36 (2H, t), 3.45 (2H, m), 3.35 (2H, m), 2.35 (2H, m), 2.15 (6H, s), 1.87 (2H, m), 1.16 (9H, s).

Example 2.2

N-(5-((5,5-Dimethyltetrahydrofuran-2-yl)methylcarbamoyl)-2-fluorophenyl)-7-(6-(4-methylpiperazin-1-yl)pyridin-3-yl)imidazo[1,2-a]pyridine-3-carboxamide

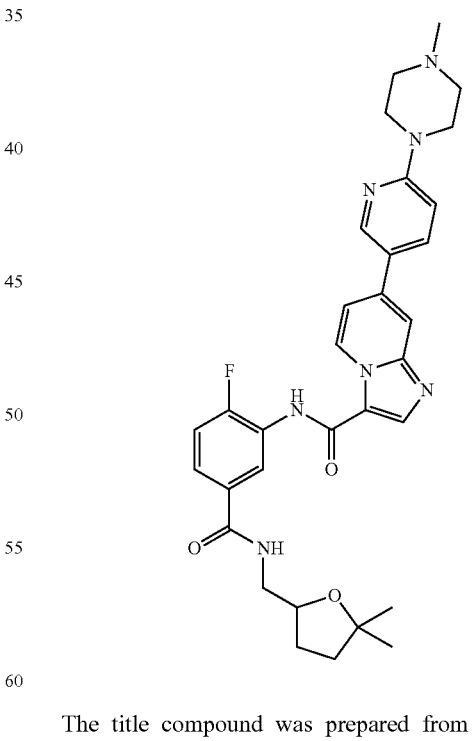

The title compound was prepared from commercially available 1-methyl-4-(5-(4,4,5,5-tetramethyl-1,3,2-dioxaborolan-2-yl)pyridin-2-yl)piperazine and Intermediate 4E analogously to Example 2.1;

LC-MS: Rt 0.71 mins; MS m/z 586/587 {M+H}+; Method 2minLC_v003

Example 2.3

N-(5-(3,4-Difluorobenzylcarbamoyl)-2-fluorophenyl)-7-(1-(3-(dimethyl amino)propyl)-1H-pyrazol-4-yl)imidazo[1,2-a]pyridine-3-carboxamide The title compound was prepared from commercially available N,N-dimethyl-3-(4-(4,4,5,5-tetramethyl-1,3,2-dioxaborolan-2-yl)-1H-pyrazol-1-yl)propan-1-amine and Intermediate 3A analogously to Example 2.1;

LC-MS: Rt 0.69 mins; MS m/z 576/577/578 {M+H}+; Method 2minLC_v003

Example 2.4

N-(5-(((5,5-Dimethyltetrahydrofuran-2-yl)methylcarbamoyl)-2-fluorophenyl)-7-(5-(((tetrahydro-2H-pyran-4-ylamino)methyl)pyridin-3-yl)imidazo[1,2-a]pyridine-3-carboxamide

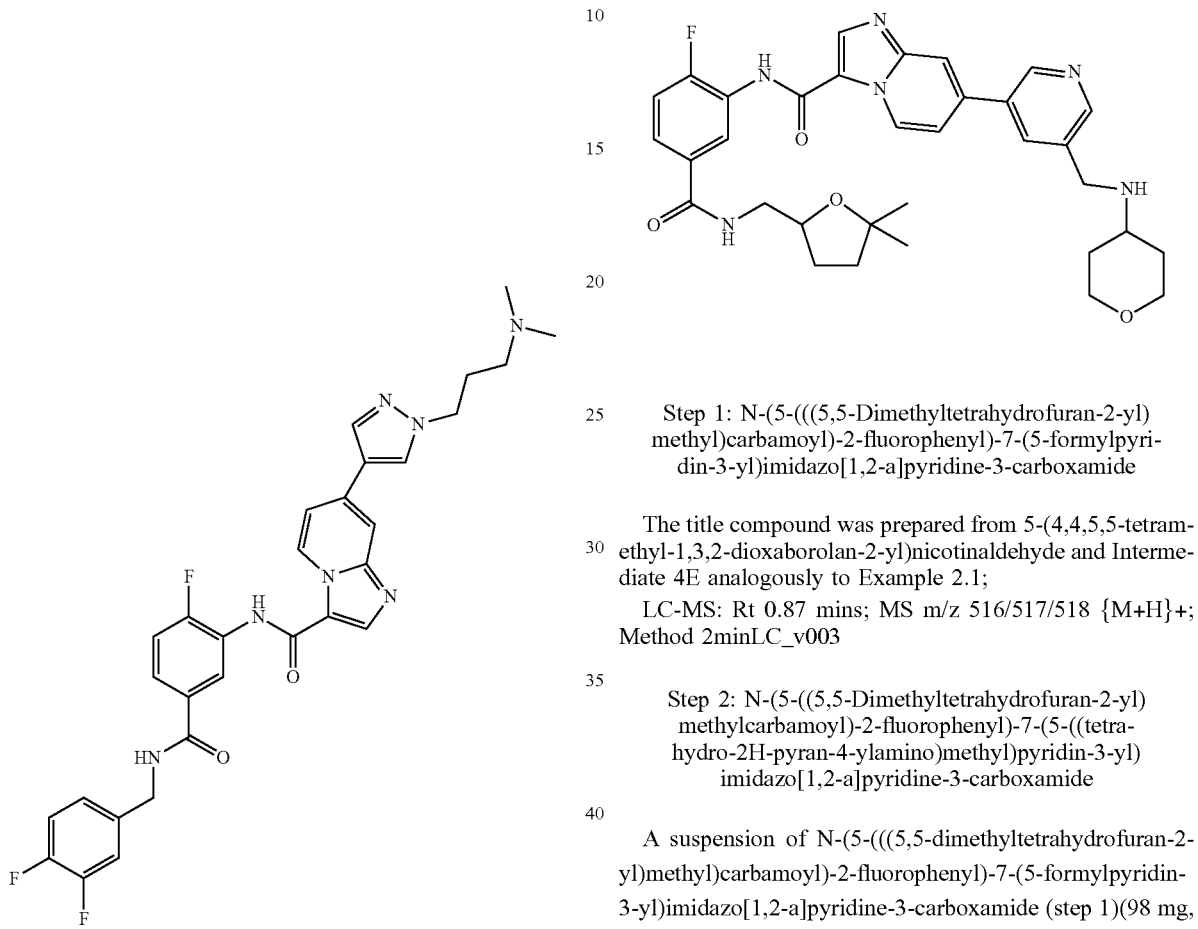

Step 1: N-(5-(((5,5-Dimethyltetrahydrofuran-2-yl)methyl)carbamoyl)-2-fluorophenyl)-7-(5-formylpyridin-3-yl)imidazo[1,2-a]pyridine-3-carboxamide The title compound was prepared from 5-(4,4,5,5-tetramethyl-1,3,2-dioxaborolan-2-yl)nicotinaldehyde and Intermediate 4E analogously to Example 2.1;

LC-MS: Rt 0.87 mins; MS m/z 516/517/518 {M+H}+; Method 2minLC_v003

Step 2: N-(5-((5,5-Dimethyltetrahydrofuran-2-yl)methylcarbamoyl)-2-fluorophenyl)-7-(5-((tetrahydro-2H-pyran-4-ylamino)methyl)pyridin-3-yl)imidazo[1,2-a]pyridine-3-carboxamide A suspension of N-(5-(((5,5-dimethyltetrahydrofuran-2-yl)methyl)carbamoyl)-2-fluorophenyl)-7-(5-formylpyridin-3-yl)imidazo[1,2-a]pyridine-3-carboxamide (step 1)(98 mg, 0.19 mmol), tetrahydro-2H-pyran-4-amine (38.4 mg, 0.380 mmol), acetic acid (0.2 ml, 3.49 mmol) and 2-picoline borane (24.16 mg, 0.228 mmol) in MeOH (2 ml) was heated at 50° C. for 3 hrs. The reaction mixture was concentrated under vacuum and the residue was redissolved in 10% MeOH/EtOAc. The mixture was washed with sat. NaHCO$_3$ and H$_2$O. The organic portion was dried MgSO$_4$ and concentrated in vacuo. The crude product was purified by chromatography on silica eluting with 0-20% 2M NH$_3$ in MeOH/DCM. The product fractions were combined and concentrated in vacuo. The residue was triturated with EtOAc/iso-hexane to afford the title compound;

LC-MS: Rt 0.69 mins; MS m/z 601/602 {M+H}+; Method 2minLC_v003

The compounds of the following tabulated Examples (Table 2) were prepared by a similar method to that of Example 2.4 from the appropriate starting compounds, the preparations of which are detailed in the 'Preparation of Intermediates' section.

TABLE 2

| Ex. | Structure Name | LC-MS/NMR |
|---|---|---|
| 2.5 | 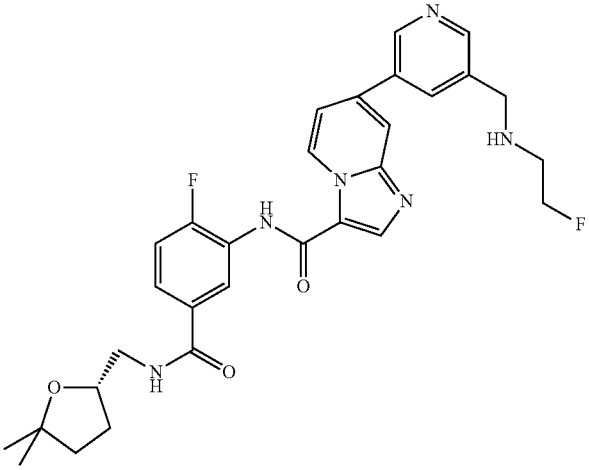 [SMILES: CC1(C)CC[C@@H](CNC(=O)c2ccc(F)c(NC(=O)c3cnc4cc(-c5cncc(CNCCF)c5)ccn34)c2)O1]<br>(S)-N-(5-(((5,5-Dimethyltetrahydrofuran-2-yl)methyl) carbamoyl)-2-fluorophenyl)-7-(5-(((2-fluoroethyl) amino)methyl)pyridin-3-yl)imidazo[1,2-a]pyridine-3-carboxamide | LCMS: Rt 0.66 mins; MS m/z 563/564 {M + H}+; Method 2 minLC_v003 |
| 2.6 | 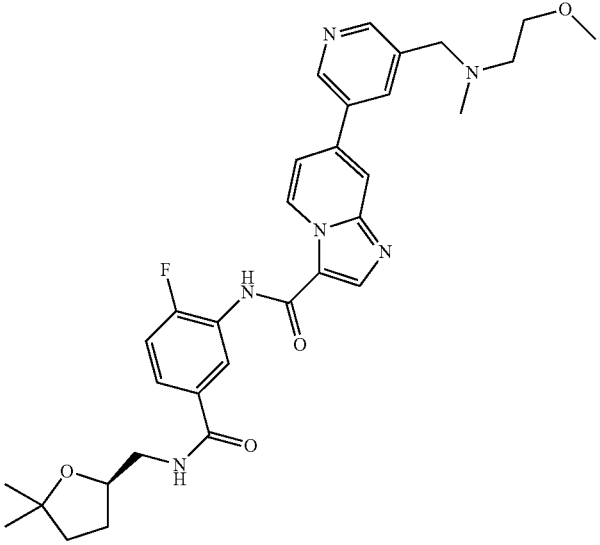<br>(R)-N-(5-(((5,5-dimethyltetrahydrofuran-2-yl)methyl) carbamoyl)-2-fluorophenyl)-7-(5-(((2-methoxyethyl) (methyl)amino)methyl)pyridin-3-yl)imidazo[1,2-a] pyridine-3-carboxamide | LCMS: Rt 0.68 mins; MS m/z 589 {M + H}+; Method 2 minLC_v003 |

TABLE 2-continued

| Ex. | Structure Name | LC-MS/NMR |
|---|---|---|
| 2.7 | 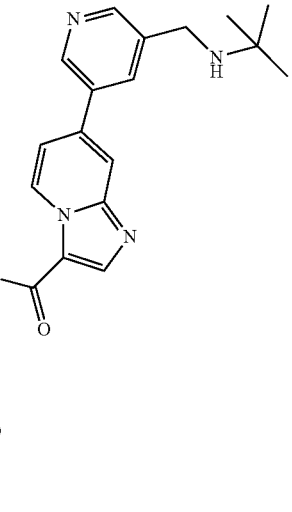<br>(R)-7-(5-((tert-butylamino)methyl)pyridin-3-yl)-N-(5-(((5,5-dimethyltetrahydrofuran-2-yl)methyl)carbamoyl)-2-fluorophenyl)imidazo[1,2-a]pyridine-3-carboxamide | LCMS: Rt 0.69 mins; MS m/z 573 {M + H}+; Method 2 minLC_v003 |

Example 3.1

N-(5-(3,4-Difluorobenzylcarbamoyl)-2-fluorophenyl)-7-(6-(2-(pyrrolidin-1-yl)ethoxy)pyridin-3-yl)imidazo[1,2-a]pyridine-3-carboxamide hydrochloride

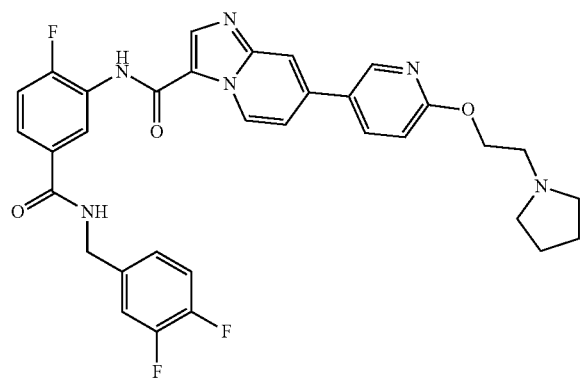 [SMILES: O=C(NCc1ccc(F)c(F)c1)c1ccc(F)c(NC(=O)c2cnc3cc(-c4ccc(OCCN5CCCC5)nc4)ccn23)c1]

Step 1: 7-(6-Chloropyridin-3-yl)-N-(5-(3,4-difluorobenzylcarbamoyl)-2-fluorophenyl)imidazo[1,2-a]pyridine-3-carboxamide A mixture comprising 7-bromo-N-(5-(3,4-difluorobenzylcarbamoyl)-2-fluorophenyl)imidazo[1,2-a]pyridine-3-carboxamide (Intermediate 3A) 100 mg, 0.199 mmol), 6-chloropyridin-3-ylboronic acid (31.3 mg, 0.199 mmol) and cesium carbonate (259 mg, 0.795 mmol) in DME (631 µL)/water (31.5 µL) was purged with nitrogen and treated with PdCl$_2$(dppf).CH$_2$Cl$_2$ adduct (8.11 mg, 9.93 µmol) The resulting mixture was heated using microwave radiation at 100° C. for 15 mins. The water was removed by pipette and the reaction mixture was diluted with MeOH. Purification of the mixture by chromatography on silica eluting with 0-20% 2M NH$_3$ in MeOH/DCM afforded the title compound;

LC-MS: Rt 0.75 mins; MS m/z 536 {M+H}+; Method 2minLC_30_v003

Step 2: N-(5-(3,4-Difluorobenzylcarbamoyl)-2-fluorophenyl)-7-(6-(2-(pyrrolidin-1-yl)ethoxy)pyridin-3-yl)imidazo[1,2-a]pyridine-3-carboxamide hydrochloride A solution of 2-(pyrrolidin-1-yl)ethanol (30.5 mg, 0.265 mmol) and sodium hydride (6.36 mg, 0.265 mmol) in toluene (442 µl) was stirred at RT for 30 mins and treated with 7-(6-chloropyridin-3-yl)-N-(5-(3,4-difluorobenzylcarbamoyl)-2-fluorophenyl)imidazo[1,2-a]pyridine-3-carboxamide (step 1). The reaction mixture was heated at 60° C. for 1 hour and the reaction was quenched with wet MeOH. Purification of the mixture by chromatography on silica eluting with 0-20% (2M NH$_3$ in MeOH)/DCM afforded a yellow solid. The solid was dissolved in MeOH and treated with 2M HCl in diethyl ether (1 eq). The solvent was removed in vacuo and purification of the crude product by chromatography on silica eluting with 2M NH$_3$ in MeOH/TBME afforded a solid. The solid was treated again with 2M HCl in diethyl ether and concentrated in vacuo to afford the title compound;

LC-MS: Rt 0.52 mins; MS m/z 615 [M+H]+; Method 2minLC_30_v003

1H NMR (400 MHz, DMSO-d6) δ10.5 (1H, s), 9.6 (1H, s), 8.8 (2H, d) 8.4 (1H, d), 8.2 (1H, d), 7.9 (1H, m), 7.7 (1H, d), 7.45 (1H, t), 7.4 (1H, m), 7.3 (1H, s), 7.2 (1H, m), 7.15 (1H, s), 7.1 (1H, d), 7 (1H, s), 4.7 (2H, d), (4.5 (2H, d), 3.3 (4H, m), 3.1 (2H, m), 2.05 (2H, m), 1.95 (2H, m).

The compounds of the following tabulated Examples (Table 3) were prepared by a similar method to that of Example 3.1 from the appropriate starting compounds, the preparations of which are detailed in the 'Preparation of Intermediates' section.

TABLE 3

| Ex. | Structure Name | LC-MS/NMR |
|---|---|---|
| 3.2 | N-(5-((2-(tert-Butoxy)ethyl)carbamoyl)-2-fluorophenyl)-7-(6-(2-(pyrrolidin-1-yl)ethoxy)pyridin-3-yl)imidazo[1,2-a]pyridine-3-carboxamide | LC-MS: Rt 0.87 mins; MS m/z 589 [M + H]+; Method 2 minLC_v003 |
| 3.3 | N-(5-(((5,5-dimethyltetrahydrofuran-2-yl)methyl)carbamoyl)-2-fluorophenyl)-7-(6-((1-methyl-piperidin-4-yl)oxy)pyridin-3-yl)imidazo[1,2-a]pyridine-3-carboxamide | LC-MS: Rt 0.71 mins; MS m/z 601/602 {M + H}+; Method 2 minLC_v003. |

Example 4.1

6-(1-Methyl-1H-pyrazol-5-yl)-N-(2-methyl-5-(2-(4-methylpiperazin-1-yl)benzylcarbamoyl)phenyl)pyrazolo[1,5-a]pyridine-3-carboxamide hydrochloride

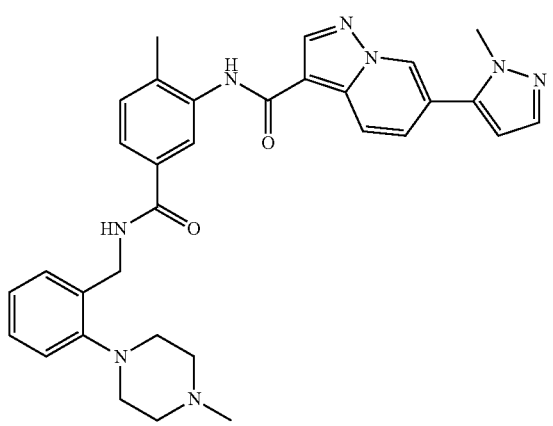 [SMILES: Cc1ccc(C(=O)NCc2ccccc2N2CCN(C)CC2)cc1NC(=O)c1cnn2cc(-c3ccnn3C)ccc12]

6-Bromo-N-(2-methyl-5-(2-(4-methylpiperazin-1-yl)benzylcarbamoyl)phenyl)pyrazolo[1,5-a]pyridine-3-carboxamide (169 mg, 0.301 mmol), 5-(1,5-dimethyl-2,4-dioxa-3-borabicyclo[3.1.0]hexan-3-yl)-1-methyl-1H-pyrazole (75 mg, 0.391 mmol) and cesium carbonate (392 mg, 1.204 mmol) in DME (3209 μL) and water (1284 ul) were combined to give a yellow solution. PdCl$_2$(dppf).CH$_2$Cl$_2$ adduct (6.15 mg, 7.52 μmol) was added and the mixture was heated using microwave radiation at 100° C. for 1 hr. A further portion of PdCl$_2$(dppf).CH$_2$Cl$_2$ adduct (6.15 mg, 7.52 μmol) was added and heating continued using microwave radiation at 100° C. for 1 hr. 5-(1,5-Dimethyl-2,4-dioxa-3-borabicyclo[3.1.0]hexan-3-yl)-1-methyl-1H-pyrazole (75 mg, 0.391 mmol), PdCl$_2$(dppf).CH$_2$Cl$_2$ adduct (6.15 mg, 7.52 μmol) and cesium carbonate (392 mg, 1.204 mmol) were added. The mixture was heated using microwave radiation at 100° C. for 2 hrs. The product was purified by chromatography on silica eluting with 0-20% 2M NH$_3$ in MeOH/DCM followed by a second column using 0-15% 2M NH$_3$ in MeOH/DCM. The resulting residue was dissolved in MeOH/DCM, filtered through a glass fibre filter paper and purified by preparative chromatography eluting with 20-50% MeCN/water (0.1% TFA). The appropriate fractions were partitioned between with NaHCO$_3$ and EtOAc and the organic portion was dried (MgSO$_4$) and concentrated to afford a colourless oil. HCl (1 equiv.) in dioxane was added and trituration with EtOAc/EtOH afforded the title compound as a solid;

LC-MS: Rt 2.66 mins; MS m/z 563/564/565 {M+H}+; Method 10minLC_v003

1H NMR (400 MHz, CD$_3$OD) δ 8.9 (1H, s), 8.7 (1H, s), 8.4 (1H, d), 7.95 (1H, s), 7.7 (1H, d), 7.65 (1h, d), 7.6 (1H, s), 7.4 (1H, d), 7.35 (1H, d), 7.3 (1H, m), 7.2 (1H, m), 7.1 (1H, t), 6.6 (1H, s), 4.7 (2H, s), 4.0 (3H, s), 3.0 (4H, m), 2.7 (4H, s broad), 2.45 (6H, d).

Example 5.1

N-(2-Bromo-5-(2-(4-methylpiperazin-1-yl)benzylcarbamoyl)phenyl)imidazo[1,2-a]pyridine-3-carboxamide

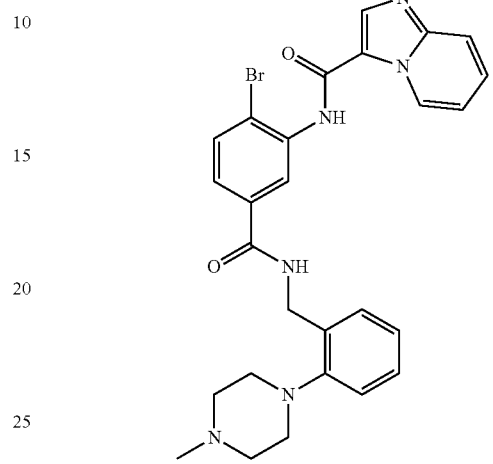

Step 1: 3-Amino-4-bromo-N-(2-(4-methylpiperazin-1-yl)benzyl)benzamide

N1,N1-dimethyl-N2-((propylimino)methylene)ethane-1,2-diamine (0.70 ml, 3.99 mmol) was added to a stirred solution/suspension of 3-amino-4-bromobenzoic acid (719 mg, 3.33 mmol), (2-(4-methylpiperazin-1-yl)phenyl)methanamine (820 mg, 3.99 mmol) and HOBt (140 mg, 1.0 mmol) in dry DCM (20 ml) under argon. After 24 hrs the reaction mixture was diluted with DCM and washed several times with water. The solvent was removed in vacuo and the resulting yellow oil was triturated with DCM/diethyl to give a yellow crystalline powder;

LCMS: Rt 0.85 min; MS m/z 403.2 [M+H]+; Method 2minLC_v003

1H NMR (400 MHz, CDCl3) δ 6.48 (1H, d), 6.42 (1H, br s), 7.30 (3H, m), 7.20 (1H, d), 7.14 (1H, t), 6.92 (1H, d), 4.72 (2H, d), 4.23 (2H, br s), 3.02 (4H, br s), 2.62 (4H, br s), 2.35 (3H, s)

Step 2: N-(2-Bromo-5-(2-(4-methylpiperazin-1-yl)benzylcarbamoyl)phenyl)imidazo[1,2-a]pyridine-3-carboxamide Imidazo[1,2-a]pyridine-3-carbonyl chloride hydrochloride (0.97 mg, 4.46 mmol) was slowly added in portions to a stirred solution of 3-amino-4-bromo-N-(2-(4-methylpiperazin-1-yl)benzyl)benzamide (step 1)(900 mg, 2.23 mmol) in dry pyridine (15 ml). The reaction was stirred at RT for 18 hrs and quenched with water. The solvent removed in vacuo. The residue was treated with a small amount of MeOH to dissolve insoluble material then partitioned between aq. NaHCO$_3$ and DCM. The organic extract was washed with brine, dried over MgSO$_4$ and concentrated in vacuo. The crude product mixture was crystallised from MeOH to give a white solid;

LCMS: Rt 0.78 min; MS m/z 549.2 [M+H]+; Method 2minLC_v003

1H NMR (400 MHz, MeOD) δ 9.52 (1H, s), 8.53 (1H, s), 8.25 (1H, s), 7.85 (1H, d), 7.77 (1H, d), 7.68 (1H, d), 7.60 (1H, t), 7.35 (1H, d), 7.22 (3H, m), 7.10 (1H, t), 4.72 (2H, d), 3.0 (4H, br s), 2.67 (4H, br s), 2.37 (3H, s).

Example 5.2

N-(2-Bromo-5-(2-(4-methylpiperazin-1-yl)benzyl-carbamoyl)phenyl)pyrazolo[1,5-a]pyridine-3-carboxamide

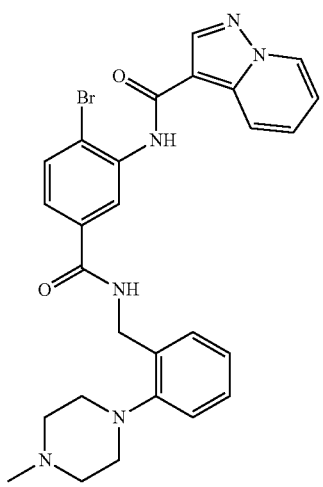 [SMILES: CN1CCN(c2ccccc2CNC(=O)c2ccc(Br)c(NC(=O)c3cnn4ccccc34)c2)CC1]

The title compound was prepared from 3-amino-4-bromo-N-(2-(4-methylpiperazin-1-yl)benzyl)benzamide (Ex 5.1, step 1) and pyrazolo[1,5-a]pyridine-3-carbonyl chloride (commercially available) analogously to Example 5.1;

LCMS: Rt 2.12 min; MS m/z 547.3, 549.3 [M+H]+; Method LowpH_v002.

1H NMR (500 MHz, d6-DMSO) δ 9.90 (1H, s), 9.05 (1H, t), 8.85 (1H, d), 8.79 (1H, s), 8.22 (1H, d), 8.14 (1H, d), 7.84 (1H, d), 7.74 (1H, dd), 7.54 (1H, m), 7.23 (2H, m), 7.13 (2H, m), 7.05 (1H, m), 4.57 (2H, d), 2.87 (4H, m), 2.50 (4H, m), 2.23 (3H, s).

Example 6.1

N-(5-(3,4-Difluorobenzylcarbamoyl)-2-fluorophenyl)-7-(3-hydroxy-3-methyl butyl)imidazo[1,2-a]pyridine-3-carboxamide

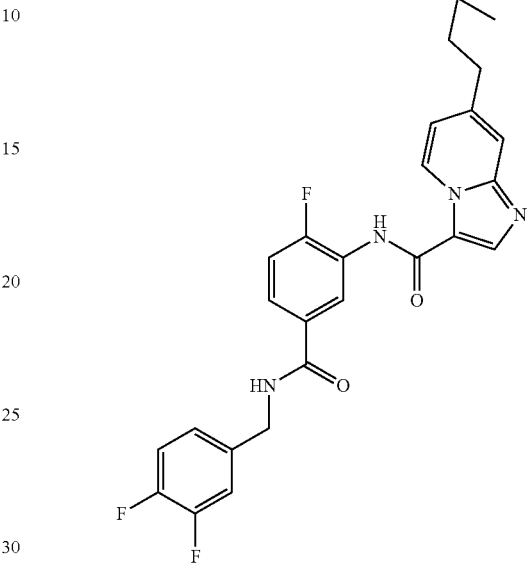

Step 1: Ethyl 3-(3-(5-(3,4-difluorobenzylcarbamoyl)-2-fluorophenylcarbamoyl) imidazo[1,2-a]pyridin-7-yl)propanoate 7-Bromo-N-(5-(3,4-difluorobenzylcarbamoyl)-2-fluorophenyl)imidazo[1,2-a]pyridine-3-carboxamide (Intermediate 3A)(1 g, 1.987 mmol), Pd$_2$(dba)$_3$ (0.091 g, 0.099 mmol) and tritertbutylphosphonium tetrafluoroborate (0.058 g, 0.199 mmol) were combined in THF (60 ml) under nitrogen and the mixture was degassed thoroughly refilling with nitrogen (×3). (3-Ethoxy-3-oxopropyl)zinc(II) bromide (19.87 ml, 9.93 mmol) was added and the mixture was heated at 60° C. for 100 mins. After cooling to RT, the mixture was absorbed onto silica and purification by chromatography eluting with 0-6% MeOH in DCM afforded a yellow oil which was triturated with EtOAc to give the title compound;

LCMS: Rt 0.99 min; MS m/z 525 [M+H]+; Method 2minLC_v003

Step 2: N-(5-(3,4-Difluorobenzylcarbamoyl)-2-fluorophenyl)-7-(3-hydroxy-3-methyl butyl)imidazo[1,2-a]pyridine-3-carboxamide Ethyl 3-(3-(5-(3,4-difluorobenzylcarbamoyl)-2-fluorophenylcarbamoyl)imidazo[1,2-a]pyridin-7-yl)propanoate (step 1)(50 mg, 0.095 mmol) was suspended in dry ether and cooled to 0° C. Methylmagnesium bromide (0.318 ml, 3.0M in ether, 0.953 mmol) was added and the mixture was stirred and allowed to warm to RT over 16 hrs. The mixture was partitioned between 10% aq. Citric acid and EtOAc. The organics were separated, dried (MgSO$_4$), filtered and evaporated to dryness. The residue was purified by chromatography on silica eluting with 0-10% MeOH in DCM to afford the title product;

LCMS: Rt 0.97 min; MS m/z 511.4 [M+H]+; Method 2minLC_v003

1H NMR (400 MHz, MeOD) δ 9.45 (2H, d), 9.08 (1H, t), 8.45 (1H, s), 8.35 (1H, d), 7.75 (1H, m), 7.55 (1H, s), 7.15-7.38 (3H, m), 7.10 (1H, d), 4.58 (2H, s), 2.88 (2H, m), 1.85 (2H, m), 1.30 (6H, s).

Example 7.1

N-(5-(3,4-Difluorobenzylcarbamoyl)-2-fluorophenyl)-7-(3-fluoro-4-(2-(piperidin-1-yl)ethylcarbamoyl)phenyl)imidazo[1,2-a]pyridine-3-carboxamide hydrochloride

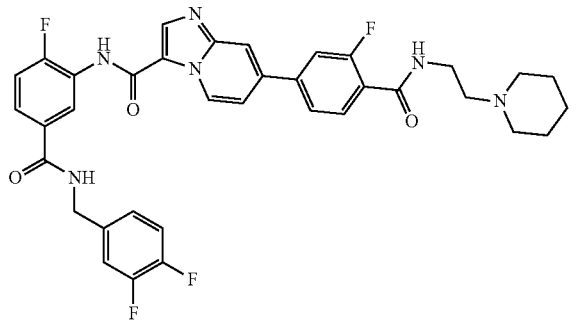 [SMILES: O=C(NCc1ccc(F)c(F)c1)c1ccc(F)c(NC(=O)c2cnc3cc(-c4ccc(C(=O)NCCN5CCCCC5)c(F)c4)ccn23)c1]

Step 1: Methyl 4-(3-(5-(3,4-difluorobenzylcarbamoyl)-2-fluorophenylcarbamoyl) imidazo[1,2-a]pyridin-7-yl)-2-fluorobenzoate 7-Bromo-N-(5-(3,4-difluorobenzylcarbamoyl)-2-fluorophenyl)imidazo[1,2-a]pyridine-3-carboxamide (Intermediate 3A)(500 mg, 0.993 mmol), methyl 2-fluoro-4-(4,4,5,5-tetramethyl-1,3,2-dioxaborolan-2-yl)benzoate (306 mg, 1.093 mmol) and cesium carbonate (1295 mg, 3.97 mmol) in water (2 ml)/DME (5 ml) were mixed to give a suspension. The mixture was degassed with nitrogen and PdCl₂(dppf).CH₂Cl₂ adduct (40.6 mg, 0.050 mmol) was added. The reaction mixture was heated using microwave radiation at 100° C. for 1 hr and partitioned between EtOAc and water. The organic portion was separated, dried (MgSO₄) and concentrated in vacuo. The crude product was triturated with MeOH/diethyl ether to afford the title compound; LCMS: Rt 1.09 min; MS m/z 567. [M+H]+; Method 2minLC_v003

Step 2: N-(5-(3,4-Difluorobenzylcarbamoyl)-2-fluorophenyl)-7-(3-fluoro-4-(2-(piperidin-1-yl)ethylcarbamoyl)phenyl)imidazo[1,2-a]pyridine-3-carboxamide Methyl 4-(3-(5-(3,4-difluorobenzylcarbamoyl)-2-fluorophenylcarbamoyl)imidazo[1,2-a]pyridin-7-yl)-2-fluorobenzoate (step 1)(50 mg, 0.087 mmol), 2-piperidin-1-yl-ethylamine (0.260 mmol), and TBD (12.07 mg, 0.087 mmol) in THF (289 μl) were heated to 70° C. for 2 days. The mixture was diluted with water (4 ml) and extracted with DCM using a phase separator. The organic portion was concentrated in vacuo and the residue was dissolved in DMSO. Puriication of the crude product was carried out by preparative LC-MS. The resulting fractions were loaded onto a pre-wetted (MeOH) Isolute® SCX-2 cartridge and washed with MeOH. The product was eluted with 7M ammonia in MeOH. The resulting residue was treated with 2M HCl (in EtOH, 1 equiv) and the concentrated in vacuo to afford the title compound as a hydrochloride salt;

LS-MS: Rt 3.79 mins; MS m/z 673 [M+H]+; Method 10minLC_v003

1H NMR (400 MHz, DMSO-d6) δ 9.1 (1H, s), 9 (1H, bs), 8.6 (1H, d), 8.4 (1H, s), 8.2 (2H, m), 7.9-7.7 (3H, m), 7.6 (1H, s), 7.4 (2H, m), 7.2 (1H, m), 4.5 (2H, d), 3.4 (2H, m), 3.2 (2H, s), 2.4 (4H, m), 1.5 (4H, m) 1.4 (2H, m).

Example 7.2

N-(5-(3,4-Difluorobenzylcarbamoyl)-2-fluorophenyl)-7-(3-fluoro-4-(2-(tetrahydro-2H-pyran-4-yl)ethylcarbamoyl)phenyl)imidazo[1,2-a]pyridine-3-carboxamide hydrochloride

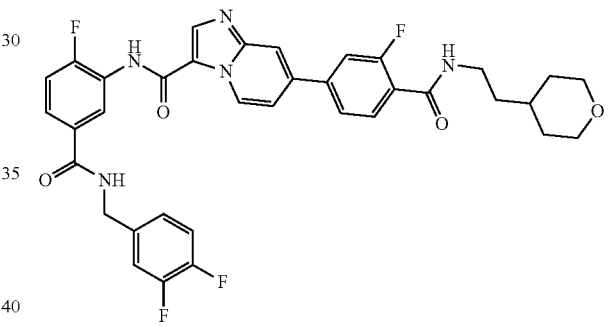

The title compound was prepared analogously to Example 7.1 using the appropriate amine in step 2. The hydrochloride salt was obtained by treating N-(5-(3,4-difluorobenzylcarbamoyl)-2-fluorophenyl)-7-(3-fluoro-4-(2-(tetrahydro-2H-pyran-4-yl)ethylcarbamoyl)phenyl)imidazo[1,2-a]pyridine-3-carboxamide with 2M HCl (in diethyl ether) and removing the solvent in vacuo;

LC-MS: Rt 3.49 mins; MS m/z 674 [M+H]+; Method 10minLC_v003

1H NMR (400 MHz, DMSO-d6) δ 9.1 (1H, s) 8.4 (2H, m), 8.25 (2H, m), 7.9 (1H, d), 7.8 (1H, d), 7.7 (1H, t), 7.65 (2H, d), 7.4 (3H, m), 7.2 (1H, m), 4.5 (2H, d), 3.8 (2H, M), 3.3 (3H, m) 3.15 (1H, s), 1.6 (3H, m), 1.5 (2H, m), 1.1 (2H, m).

Example 7.3

N-(5-((2-(2,2-Dimethylpyrrolidin-1-yl)ethyl)carbamoyl)-2-fluorophenyl)-7-(1-methyl-1H-pyrazol-4-yl)imidazo[1,2-a]pyridine-3-carboxamide

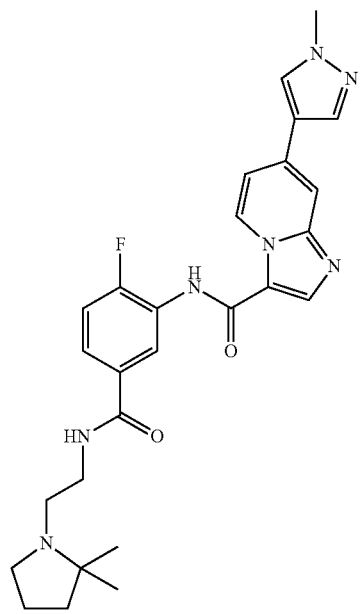 [SMILES: Cn1cc(-c2ccn3c(C(=O)Nc4cc(C(=O)NCCN5CCCC5(C)C)ccc4F)cnc3c2)cn1]

Step 1: 4-Fluoro-3-(7-(1-methyl-1H-pyrazol-4-yl)imidazo[1,2-a]pyridine-3-carboxamido)benzoic acid A mixture comprising methyl 3-(7-bromoimidazo[1,2-a]pyridine-3-carboxamido)-4-fluorobenzoate (Intermediate 1A)(5.41 g, 13.79 mmol), 1-methyl-1H-pyrazol-4-ylboronic acid (1.911 g, 15.17 mmol), Pd(dppf)Cl$_2$.DCM (1.127 g, 1.379 mmol) and cesium carbonate (13.48 g, 41.4 mmol) in DME (100 ml) and water (10 ml) was heated at 100° C. for 4 hrs. 3 equivalents of sodium carbonate were added and the mixture was heated to 100° C. for 6 hrs. A further 3 equivalents of sodium carbonate were added and the reaction was heated at 100° C. overnight.

The reaction mixture was cooled to 50° C. and filtered through glass fiber filter paper. The filtrate was acidified to pH3 and allowed to cool to room temperature. A brown precipitate formed which was collected by vacuum filtration and dried at 45° C. to afford the title compound;

LC-MS: Rt 0.68 mins; MS m/z 380/381 {M+H}+; Method 2minLC_v003.

Step 2: N-(5-((2-(2,2-Dimethylpyrrolidin-1-yl)ethyl)carbamoyl)-2-fluorophenyl)-7-(1-methyl-1H-pyrazol-4-yl)imidazo[1,2-a]pyridine-3-carboxamide A solution of 4-fluoro-3-(7-(1-methyl-1H-pyrazol-4-yl)imidazo[1,2-a]pyridine-3-carboxamido)benzoic acid (step 1)(6.31 g, 16.63 mmol), 2-(2,2-dimethylpyrrolidin-1-yl)ethanamine (2.84 g, 19.96 mmol) and triethylamine (6.96 ml, 49.9 mmol) in DMF (36.9 ml) and EtOAc (2 ml) was treated dropwise with®T3P (propylphosphonic anhydride) (50% w/w in EtOAc) (15.88 g, 24.95 mmol). The resulting mixture was stirred at RT for 16 hrs and diluted with 10% MeOH/EtOAc (62.7 ml). The mixture was washed with 0.5 M LiCl, H$_2$O and sat. NaHCO$_3$. The aqueous layer was back-extracted with 10% MeOH EtOAc (62.7 ml) (3×100 ml). The combined organic extracts was dried MgSO$_4$, filtered and concentrated in vacuo. The resulting solid was triturated with EtOAc and dried at 45° C. to afford the title compound;

LC-MS: Rt 0.59 mins; MS m/z 504/505/506 {M+H}+; Method 2minLC_v003

Further purification was carried out by loading the product onto 2 pre-washed 10 g Isolute SCX-2 columns and washing through with MeOH. The product was eluted with 2N NH$_3$ in MeOH to afford a brown solution which was triturated with EtOAc to the title compound;

1H NMR (400 MHz), CD$_3$OD) δ 9.4 (1H, d), 8.45 (1H, s), 8.3 (1H, m), 8.2 (1H, s), 8.0 (1H, s), 7.85 (1H, s), 7.8 (1H, m), 7.4 (1H, m), 7.3 (1H, t), 4.0 (3H, s), 3.5 (2H, m), 2.9 (2H, t), 2.7 (2H, t), 1.8 (2H, m), 1.7 (2H, m), 1.0 (6H, s).

Example 7.4

N-(5-(2-(2,2-Dimethylpyrrolidin-1-yl)ethylcarbamoyl)-2-fluorophenyl)-7-(3-fluoro-4-((1R,2R)-2-hydroxycyclohexylcarbamoyl)phenyl)imidazo[1,2-a]pyridine-3-carboxamide

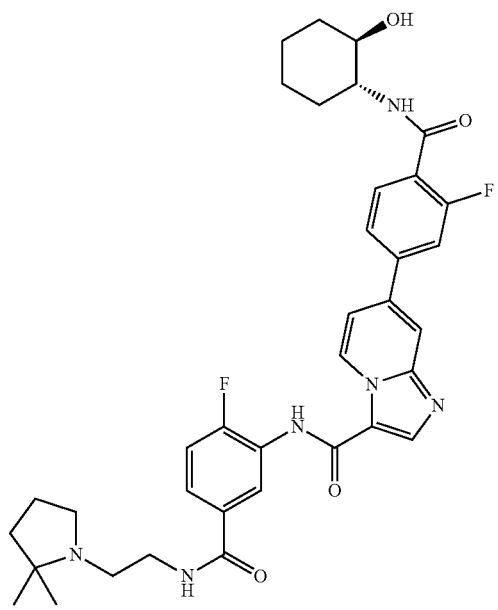 [SMILES: CC1(C)CCCN1CCNC(=O)c1ccc(F)c(NC(=O)c2cnc3cc(-c4ccc(C(=O)N[C@@H]5CCCC[C@H]5O)c(F)c4)ccn23)c1]

Step 1: 7-Bromo-N-(5-(2-(2,2-dimethylpyrrolidin-1-yl)ethylcarbamoyl)-2-fluorophenyl)imidazo[1,2-a]pyridine-3-carboxamide 3-(7-Bromoimidazo[1,2-a]pyridine-3-carboxamido)-4-fluorobenzoic acid (prepared by hydrolysis of methyl 3-(7-bromoimidazo[1,2-a]pyridine-3-carboxamido)-4-fluorobenzoate (Intermediate 1A) using NaOH) (700 mg, 1.851 mmol), 2-(2,2-dimethylpyrrolidin-1-yl)ethanamine (290 mg, 2.036 mmol) and triethylamine (0.774 ml, 5.55 mmol) were dissolved in EtOAc (7.284 ml) and DMF (1.28 ml) to give a yellow solution.®T3P (propylphosphonic anhydride) (1.620 ml, 2.036 mmol) was added and the mixture was stirred at room temperature for 90 mins. The reaction mixture was diluted with EtOAc and washed with 0.5M LiCl in H₂O and sat NaHCO₃. The organic portion was dried MgSO₄, filtered and concentrated in vacuo. The residue was triturated with EtOAc/iso-hexane to afford the title compound as a white solid;

LC-MS: Rt 0.67 mins; MS m/z 503/504/505 {M+H}+; Method 2minLC_v003

Step 2: Methyl 4-(3-(5-(2-(2,2-dimethylpyrrolidin-1-yl)ethylcarbamoyl)-2-fluorophenylcarbamoyl) imidazo[1,2-a]pyridin-7-yl)-2-fluorobenzoate The title compound was prepared from 4-(methoxycarbonyl)phenylboronic acid and 7-bromo-N-(5-(2-(2,2-dimethylpyrrolidin-1-yl)ethylcarbamoyl)-2-fluorophenyl) imidazo[1,2-a]pyridine-3-carboxamide (step 1) analogously to Example 7.3 step 1;

LC-MS: Rt 0.75 mins; MS m/z 576/577 [M+H]+; Method 2minLC_v003

Step 3: 4-(3-(5-(2-(2,2-Dimethylpyrrolidin-1-yl) ethylcarbamoyl)-2-fluorophenyl carbamoyl)imidazo [1,2-a]pyridin-7-yl)-2-fluorobenzoic acid A mixture comprising methyl 4-(3-(5-(2-(2,2-dimethylpyrrolidin-1-yl)ethylcarbamoyl)-2-fluorophenylcarbamoyl) imidazo[1,2-a]pyridin-7-yl)-2-fluorobenzoate (step 2)(409 mg, 0.711 mmol) and sodium hydroxide (142 mg, 3.55 mmol) in MeOH (5 ml) was heated at 60° C. overnight. The reaction mixture was concentrated under vacuum and the resulting residue was dissolved in water and adjusted to pH 5 using 1M HCl. The solid precipitate was collected by filtration and dried at 45° C. The aqueous portion was concentrated in vacuo and the residue was sonicated in 5% MeOH inDCM. The resulting suspension was filtered and the filtrate was combined with the solid precipitate from the first filtration. The combined product were evaporated to dryness and dried at 45° C. in the vacuum oven.

LC-MS: Rt 0.68 mins; MS m/z 562/563 {M+H}+; Method 2minLC_v003

Step 4: N-(5-(2-(2,2-Dimethylpyrrolidin-1-yl)ethylcarbamoyl)-2-fluorophenyl)-7-(3-fluoro-4-((1R,2R)-2-hydroxycyclohexylcarbamoyl)phenyl)imidazo[1,2-a]pyridine-3-carboxamide The title compound was prepared from (1R,2R)-2-aminocyclohexanol and 4-(3-(5-(2-(2,2-dimethylpyrrolidin-1-yl) ethylcarbamoyl)-2-fluorophenylcarbamoyl)imidazo[1,2-a] pyridin-7-yl)-2-fluorobenzoic acid (step 3) analogously to Example 7.3 step 2; LC-MS: Rt 0.70 mins; MS m/z 659/660 {M+H}+; Method 2minLC_v003

Example 7.5

N-(5-(2-(2,2-Dimethylpyrrolidin-1-yl)ethylcarbamoyl)-2-fluorophenyl)-7-(3-fluoro-4-(1-hydroxy-2-methylpropan-2-ylcarbamoyl)phenyl)imidazo[1,2-a] pyridine-3-carboxamide The title compound was prepared analogously to Example 7.4 from 4-(3-(5-(2-(2,2-dimethylpyrrolidin-1-yl)ethylcarbamoyl)-2-fluorophenylcarbamoyl)imidazo[1,2-a]pyridin-7-yl)-2-fluorobenzoic acid (step 3) and 2-amino-2-methylpropan-1-ol; LC-MS: Rt 0.69 mins; MS m/z 633/634/635 [M+H]+; Method 2minLC_v003.

Example 7.6

N-(5-(2-(2,2-Dimethylpyrrolidin-1-yl)ethylcarbamoyl)-2-methylpyridin-3-yl)-6-(3-fluoro-4-(1-hydroxy-2-methylpropan-2-ylcarbamoyl)phenyl)pyrazolo[1,5-a]pyridine-3-carboxamide

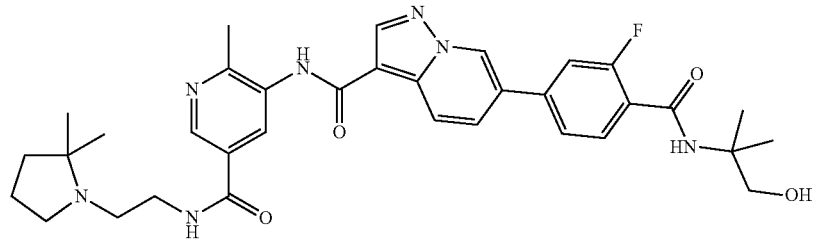 [SMILES: Cc1ncc(C(=O)NCCN2CCCC2(C)C)cc1NC(=O)c1cnn2cc(-c3ccc(C(=O)NC(C)(C)CO)c(F)c3)ccc12]

Steps 1, 2 and 3: 4-(3-(5-(2-(2,2-Dimethylpyrrolidin-1-yl)ethylcarbamoyl)-2-methylpyridin-3-ylcarbamoyl)pyrazolo[1,5-a]pyridin-6-yl)-2-fluorobenzoic acid The title compound was prepared from Intermediate 1E analogously to Example 7.4 steps 1, 2 and 3;

LC-MS: Rt 0.72 mins; MS m/z 559 {M+H}+; Method 2minLowpHv01.

Step 4: N-(5-(2-(2,2-Dimethylpyrrolidin-1-yl)ethylcarbamoyl)-2-methylpyridin-3-yl)-6-(3-fluoro-4-(1-hydroxy-2-methylpropan-2-ylcarbamoyl)phenyl)pyrazolo[1,5-a]pyridine-3-carboxamide A solution of 2-amino-2-methylpropan-1-ol (12.64 mg, 0.142 mmol), 4-(3-(5-(2-(2,2-dimethylpyrrolidin-1-yl)ethylcarbamoyl)-2-methylpyridin-3-ylcarbamoyl)pyrazolo[1,5-a]pyridin-6-yl)-2-fluorobenzoic acid (72 mg, 0.129 mmol) and triethylamine (0.054 ml, 0.387 mmol) in DCM (5 ml) was treated with HATU (53.9 mg, 0.142 mmol) and DMF (1 ml). After stirring at RT for 3 hrs, the reaction mixture was diluted with DCM and washed with sat NaHCO₃ and H₂O. The organic portion was separated, dried MgSO₄ and concentrated in vacuo. The product was purified by flash column chromatography on silica eluting with 0-25% 2M NH₃ in MeOH/DCM. The product fractions were combined and concentrated to afford an orange oil which was triturated with EtOAc/hexane to afford a pale brown soid.

LC-MS: Rt 0.74 mins; MS m/z 630/631/632 {M+H}+; Method 2minLowpHv01

Example 8.1

N-(5-(3,4-Difluorobenzylcarbamoyl)-2-fluorophenyl)-7-(3-fluoro-4-(3-morpholino propylcarbamoyl)phenyl)imidazo[1,2-a]pyridine-3-carboxamide hydrochloride

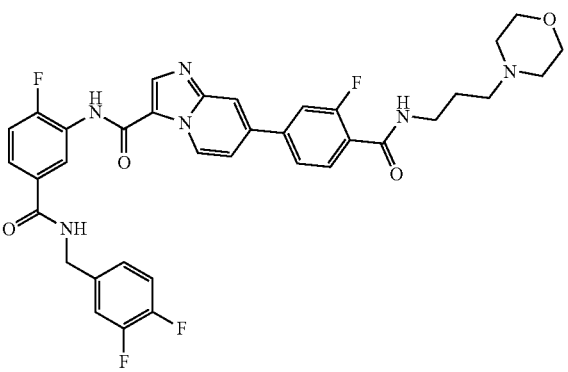 [SMILES: O=C(NCc1ccc(F)c(F)c1)c1ccc(F)c(NC(=O)c2cnc3cc(-c4ccc(C(=O)NCCCN5CCOCC5)c(F)c4)ccn23)c1]

Step 1: 4-(3-(5-(3,4-Difluorobenzylcarbamoyl)-2-fluorophenylcarbamoyl)imidazo[1,2-a]pyridin-7-yl)-2-fluorobenzoic acid A solution of methyl 4-(3-(5-(3,4-difluorobenzylcarbamoyl)-2-fluorophenylcarbamoyl) imidazo[1,2-a]pyridin-7-yl)-2-fluorobenzoate (Example 7.1, step 1) (497 mg, 0.862 mmol) and 2M NaOH (4311 µL, 8.62 mmol) in MeOH (2874 µL) was stirred at RT overnight. The solvent was removed in vacuo and the residue was acidified with 2M HCl to pH 2 and extracted with DCM. The organic extracts were dried over MgSO₄, filtered and concentrated in vacuo to afford the title compound;

LCMS: Rt 0.66 min; MS m/z 563 [M+H]+; Method 2minLC_30_v003

Step 2: N-(5-(3,4-Difluorobenzylcarbamoyl)-2-fluorophenyl)-7-(3-fluoro-4-(3-morpholino propylcarbamoyl)phenyl)imidazo[1,2-a]pyridine-3-carboxamide hydrochloride A mixture comprising 4-(3-(5-(3,4-difluorobenzylcarbamoyl)-2-fluorophenyl carbamoyl)imidazo[1,2-a]pyridin-7-yl)-2-fluorobenzoic acid (100 mg, 0.178 mmol), 3-morpholinopropan-1-amine (51.3 mg, 0.356 mmol), HATU (74.4 mg, 0.196 mmol) and Hunig's base (34.2 μL, 0.196 mmol) in THF (593 μL) was stirred at room temperature overnight. The solvent was removed in vacuo and the residue was partitioned between water and DCM. The organic portion was dried over MgSO₄, filtered and concentrated in vacuo. The residue was purified by chromatography on silica eluting with 0-20% 2M NH3 in Methanol in TBME. The resulting solid was treated with 2M HCl in diethyl ether and concentrated in vacuo to afford the title compound;

LCMS: Rt 3.09 mins; MS m/z 688 [M+H]+; Method 10minLC_v003

1H NMR (400 MHz, DMSO-d6) δ 10.5 (1H, s), 10.4 (1H, bs), 9.5 (1H, d), 9.2 (1H, t), 8.8 (1H, s), 8.6 (1H, bs), 8.3 (1H, s), 8.2 (1H, d), 7.9 (1H, d) 7.8 (1H, m), 7.7 (1H, d), 7.5 (1H, m) m 7.4 (1H, m) 7.2 (1H, m) 4.5 (2H, d), 4 (2H, d), 3.75 (2H, t), 3.45 (4H, m), 3.1 (4H, m) 2 (2H, m).

Example 8.2

N-(5-(2-(2,6-cis-Dimethylpiperidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide

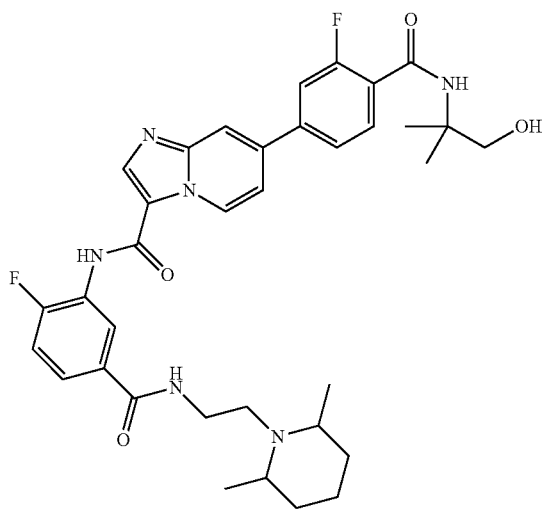 [SMILES: CC1CCCC(C)N1CCNC(=O)c1ccc(F)c(NC(=O)c2cnc3cc(-c4ccc(C(=O)NC(C)(C)CO)c(F)c4)ccn23)c1]

Step 1: 4-(3-(5-(2-(2,6-cis-Dimethylpiperidin-1-yl)ethylcarbamoyl)-2-fluorophenyl carbamoyl)imidazo[1,2-a]pyridin-7-yl)-2-fluorobenzoic acid The title compound was prepared from 7-bromo-N-(5-(2-(2,6-cis-dimethylpiperidin-1-yl)ethylcarbamoyl)-2-fluorophenyl)imidazo[1,2-a]pyridine-3-carboxamide (Intermediate 4C) and 3-fluoro-4-(methoxycarbonyl)phenylboronic acid analogously to Example 1.20;

LCMS: Rt 0.50 mins; MS m/z 294 [M+H]+; Method 2minLowpH

Step 2: N-(5-(2-(2,6-cis-Dimethylpiperidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide The title compound was prepared from 4-(3-(5-(2-(2,6-cis-dimethylpiperidin-1-yl)ethylcarbamoyl)-2-fluorophenyl carbamoyl)imidazo[1,2-a]pyridin-7-yl)-2-fluorobenzoic acid (step 1) and 2-amino-2-methylpropan-1-ol analogously to Example 8.1, step 2;

LCMS: Rt 0.73 mins; MS m/z 647 [M+H]+; Method 2minLowpH

Example 8.3

7-(3-Fluoro-4-(2-fluoroethylcarbamoyl)phenyl)-N-(2-fluoro-5-(2-(4-methylpiperazin-1-yl)benzylcarbamoyl)phenyl)imidazo[1,2-a]pyridine-3-carboxamide

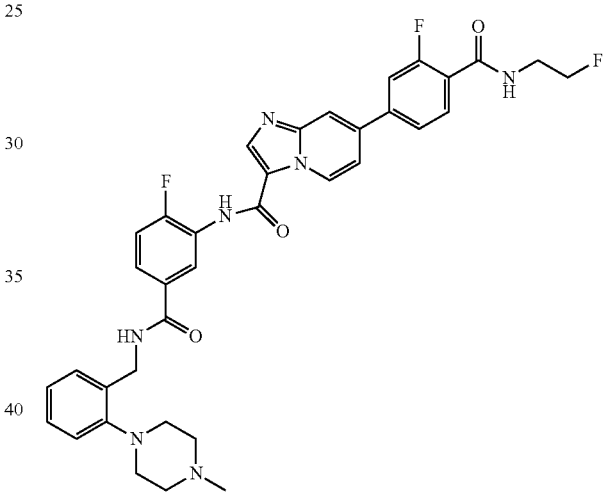

Step 1: Methyl 2-fluoro-4-(3-(2-fluoro-5-(2-(4-methylpiperazin-1-yl)benzylcarbamoyl)phenylcarbamoyl)imidazo[1,2-a]pyridin-7-yl)benzoate The title compound is prepared from 7-Bromo-N-(2-fluoro-5-(2-(4-methylpiperazin-1-yl)benzylcarbamoyl)phenyl)imidazo[1,2-a]pyridine-3-carboxamide (Example 1.1 step 1) and 3-fluoro-4-(methoxycarbonyl)phenylboronic acid analogously to Example 1.1 step 2;

LC-MS: Rt 0.79 mins; MS m/z 639/640 {M+H}+; Method 2minLC_v003

Step 2 and 3: 7-(3-Fluoro-4-(2-fluoroethylcarbamoyl)phenyl)-N-(2-fluoro-5-(2-(4-methylpiperazin-1-yl)benzylcarbamoyl)phenyl)imidazo[1,2-a]pyridine-3-carboxamide The title compound was prepared from methyl 2-fluoro-4-(3-(2-fluoro-5-(2-(4-methylpiperazin-1-yl)benzylcarbamoyl)phenylcarbamoyl)imidazo[1,2-a]pyridin-7-yl)benzoate (step) and 2-fluoroethanamine analogously Example 8.1 steps 1 and 2;

LC-MS: Rt 0.74 mins; MS m/z 670/671 {M+H}+; Method 2minLC_v003

Example 8.4

N-(2-Fluoro-5-(2-(4-methylpiperazin-1-yl)benzyl-carbamoyl)phenyl)-7-(3-fluoro-5-(2-hydroxy ethyl-carbamoyl)phenyl)imidazo[1,2-a]pyridine-3-carboxamide

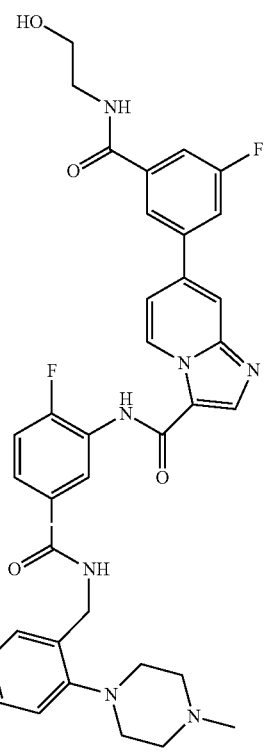

The title compound was prepared from 7-bromo-N-(2-fluoro-5-(2-(4-methylpiperazin-1-yl)benzylcarbamoyl)phenyl)imidazo[1,2-a]pyridine-3-carboxamide (Example 1.1 step1 and 2-aminoethanol analogously to Example 8.2 steps 1 and 2;

LC-MS: Rt 0.71 mins; MS m/z 668/669/670 [M+H]+; Method 2minLC_v003.

Example 9.0

N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide

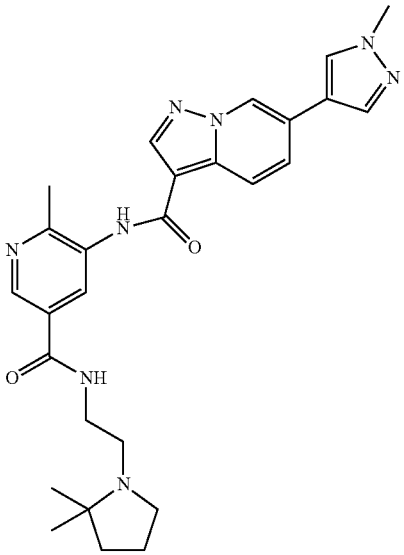 [SMILES: Cc1ncc(C(=O)NCCN2CCCC2(C)C)cc1NC(=O)c1cnn2cc(-c3cnn(C)c3)ccc12]

Step 1: Methyl 5-(6-bromopyrazolo[1,5-a]pyridine-3-carboxamido)-6-methylnicotinate 6-Bromopyrazolo[1,5-a]pyridine-3-carboxylic acid (7.71 g, 32.0 mmol) in toluene (80 ml) was treated with thionyl chloride (18.67 ml, 256 mmol) and was heated to 110° C. for 6 hr. The solvent was removed in vacuo and the residue was treated with pyridine (80 ml), methyl 5-amino-6-methylnicotinate (4.25 g, 25.6 mmol) and oven dried molecular sieves. The reaction mixture was stirred at RT overnight and then treated with MeOH (250 ml). The resulting suspension was removed by filtration. The filtrate was triturated with methanol and the solid produced was isolated to afford the title compound;

LCMS: Rt 0.91 mins; MS m/z 391.4 [M+H]+; Method 2minLowpH

Step 2: 6-Methyl-5-(6-(1-methyl-1H-pyrazol-4-yl)pyrazolo[1,5-a]pyridine-3-carboxamido)nicotinic acid Methyl 5-(6-bromopyrazolo[1,5-a]pyridine-3-carboxamido)-6-methylnicotinate (step 1) (7 g, 17.99 mmol), 1-methyl-4-(4,4,5,5-tetramethyl-1,3,2-dioxaborolan-2-yl)-1H-pyrazole (4.49 g, 21.58 mmol) and cesium carbonate (23.44 g, 71.9 mmol) were stirred in 1,2-dimethoxyethane (60 ml) and water (25.00 ml). The mixture was degassed thoroughly refilling with nitrogen. PdCl$_2$(dppf).CH$_2$Cl$_2$ adduct (0.350 g, 0.429 mmol) was added and the mixture was degassed thoroughly refilling with nitrogen, The mixture was stirred at 100° C. for 7 hrs and then cooled to 50° C. and filtered through glass-fiber paper. The filtrate was acidified to pH 5 by the addition of 2M HCl and filtered. The foam residue was dissolved in DCM/MeOH (1:1) and azeotroped with toluene (×2). The resulting solid was dried in a vacuum oven to afford the title compound;

LCMS: Rt 0.69 mins; MS m/z 377.5 [M+H]+; Method 2minLowpH

Step 3: N-(5-(2-(2,2-Dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide 6-Methyl-5-(6-(1-methyl-1H-pyrazol-4-yl)pyrazolo[1,5-a]pyridine-3-carboxamido)nicotinic acid (6.6 g, 1.1 equiv) and 2-(2,2-dimethylpyrrolidin-1-yl)ethanamine (2.397 g, 11.14 mmol) were combined in DMF (100 ml) and treated with DIPEA (8.34 ml, 47.7 mmol) followed by HATU (4.44 g, 11.67 mmol). After strring at RT for 90 mins, the mixture was partitioned between water (1 L) and EtOAc (750 ml). The resulting suspension was removed by filtration and the organic portion was washed with aqueous sodium bicarbonate, 0.5M lithium chloride, brine, dried MgSO₄, filtered and evaporated to dryness. Purification by chromatography on silica eluting with 0-20% 2M NH₃ in MeOH/TBME afforded residue which was recrystallised from acetone to afford the title compound;

LCMS: Rt 0.61 mins; MS m/z 501 [M+H]+; Method 2minLowpH

1H NMR (400 MHz, DMSO) δ 9.75 (1H, s), 9.15 (1H, s), 8.75 (2H, m), 8.58 (1H, t), 8.32 (1H, s), 8.25 (1H, s), 8.21 (1H, d), 8.07 (1H, s), 7.82 (1H, d), 3.89 (3H, s), 3.34 (4H, m), 2.76 (2H, t), 2.56 (3H, s), 1.69 (2H, m), 1.53 (2H, m) 0.92 (6H, s)

The compounds of the following tabulated Examples (Table 4) were prepared by a similar methods to that of Example 9 from the appropriate starting compounds, the preparations of which are detailed herein and in the 'Preparation of Intermediates' section.

TABLE 4

| Ex. | Structure Name | [M + H]⁺/NMR |
|---|---|---|
| 9.1 | 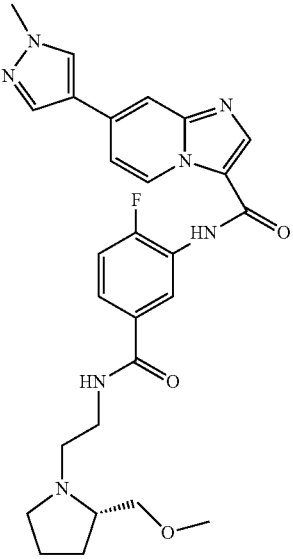 [SMILES: COC[C@@H]1CCCN1CCNC(=O)c1ccc(F)c(NC(=O)c2cnc3cc(-c4cnn(C)c4)ccn23)c1]<br>(S)-N-(2-Fluoro-5-(2-(2-(methoxymethyl)pyrrolidin-1-yl)ethylcarbamoyl)phenyl)-7-(1-methyl-1H-pyrazol-4-yl)imidazo[1,2-a]pyridine-3-carboxamide | Rt 0.59 mins; MS m/z 520 [M + H]+; Method 2 minLowpHv01 |

TABLE 4-continued

| Ex. | Structure Name | [M + H]+/NMR |
|---|---|---|
| 9.2 | 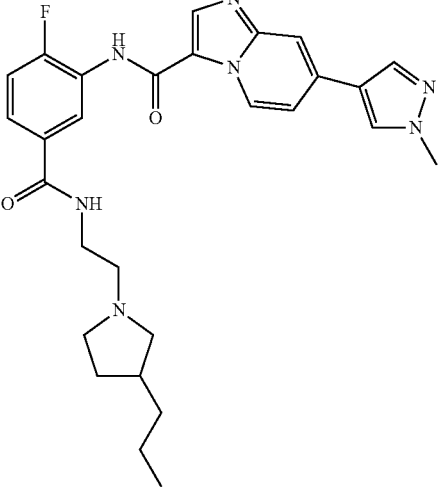<br>N-(2-Fluoro-5-((2-(3-propylpyrrolidin-1-yl)ethyl)carbamoyl)phenyl)-7-(1-methyl-1H-pyrazol-4-yl)imidazo[1,2-a]pyridine-3-carboxamide | Rt 2.40 mins: MS m/z 516.5[M + H]+ Method 10 minLowpHv01 |
| 9.3 | 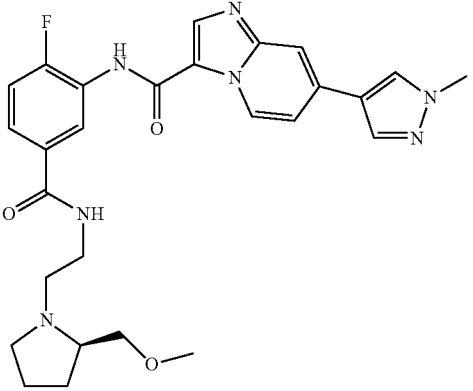 [SMILES: COC[C@H]1CCCN1CCNC(=O)c1ccc(F)c(NC(=O)c2cnc3cc(-c4cnn(C)c4)ccn23)c1]<br>(R)-N-(2-Fluoro-5-((2-(2-(methoxymethyl)pyrrolidin-1-yl)ethyl)carbamoyl)phenyl)-7-(1-methyl-1H-pyrazol-4-yl)imidazo[1,2-a]pyridine-3-carboxamide | Rt 0.57 mins; MS m/z 520/521 [M + H]+; Method 2 minLowpHv01 |
| 9.4 | 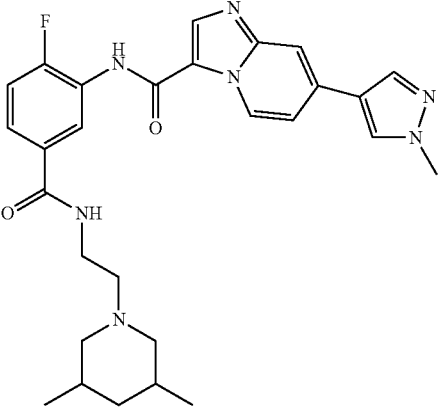 [SMILES: CC1CC(C)CN(CCNC(=O)c2ccc(F)c(NC(=O)c3cnc4cc(-c5cnn(C)c5)ccn34)c2)C1]<br>N-(5-((2-(3,5-Dimethylpiperidin-1-yl)ethyl)carbamoyl)-2-fluorophenyl)-7-(1-methyl- | Rt 2.36 mins: MS m/z 516 [M + H]+ Method 10 minLowpHv01 |

TABLE 4-continued

| Ex. | Structure Name | [M + H]⁺/NMR |
|---|---|---|
| | 1H-pyrazol-4-yl)imidazo[1,2-a]pyridine-3-carboxamide | |
| 9.5 | 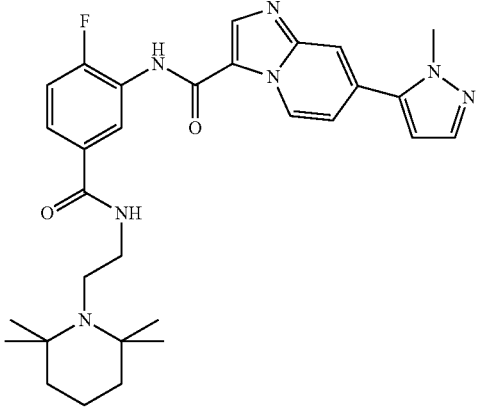 [SMILES: Cn1nccc1-c1ccn2c(C(=O)Nc3cc(C(=O)NCCN4C(C)(C)CCCC4(C)C)ccc3F)cnc2c1]<br>N-(2-fluoro-5-((2-(2,2,6,6-tetramethylpiperidin-1-yl)ethyl)carbamoyl)phenyl)-7-(1-methyl-1H-pyrazol-5-yl)imidazo[1,2-a]pyridine-3-carboxamide hydrochloride salt | LCMS: Rt 0.81 mins; MS m/z 546.4 [M + H]+; Method 2 minLowpH |
| 9.6 | 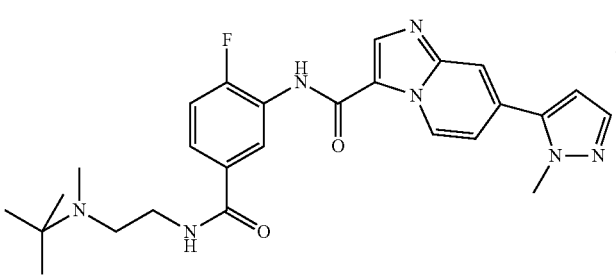 [SMILES: CN(CCNC(=O)c1ccc(F)c(NC(=O)c2cnc3cc(-c4ccnn4C)ccn23)c1)C(C)(C)C]<br>N-(5-((2-(tert-butyl(methyl)amino)ethyl)carbamoyl)-2-fluorophenyl)-7-(1-methyl-1H-pyrazol-5-yl)imidazo[1,2-a]pyridine-3-carboxamide hydrochloride salt | LCMS: Rt 0.75 mins; MS m/z 492.3 [M + H]+; Method 2 minLC_v003 |
| 9.7 | 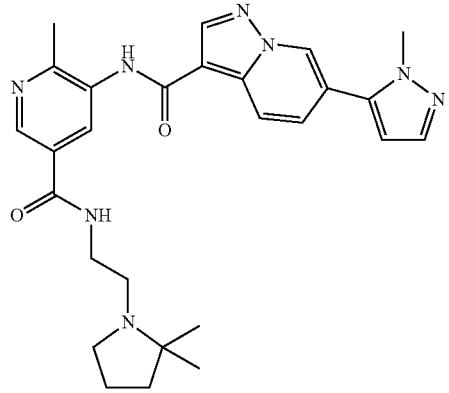 [SMILES: Cc1ncc(C(=O)NCCN2CCCC2(C)C)cc1NC(=O)c1cnn2cc(-c3ccnn3C)ccc12]<br>N-(5-((2-(2,2-dimethylpyrrolidin-1-yl)ethyl)carbamoyl)-2-methylpyridin-3-yl)-6-(1-methyl-1H-pyrazol-5-yl)pyrazolo[1,5-a]pyridine-3-carboxamide hydrochloride salt | LCMS: Rt 0.59 mins; MS m/z 501/502/503 {M + H}⁺; Method 2 minLC_v003 |

TABLE 4-continued

| Ex. | Structure Name | [M + H]+/NMR |
|---|---|---|
| 9.8 | 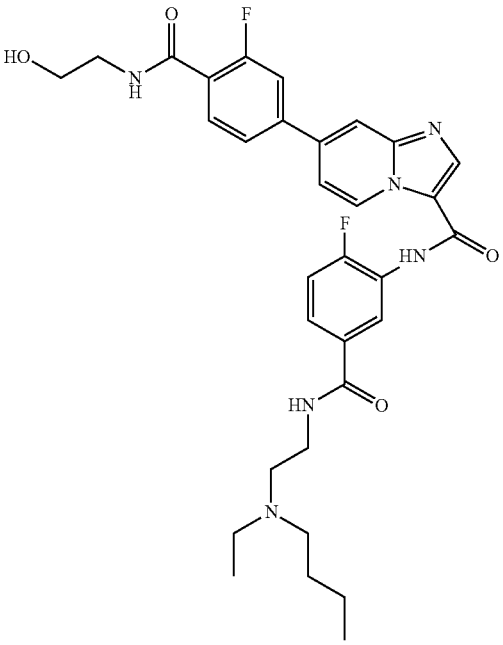 [SMILES: CCCCN(CC)CCNC(=O)c1ccc(F)c(NC(=O)c2cnc3cc(-c4ccc(C(=O)NCCO)c(F)c4)ccn23)c1]<br>N-(5-((2-(butyl(ethyl)amino)ethyl)carbamoyl)-2-fluorophenyl)-7-(3-fluoro-4-((2-hydroxy-ethyl)carbamoyl)phenyl)imidazo[1,2-a]pyridine-3-carboxamide | LCMS: Rt 0.66 mins; MS m/z 607/608 {M + H}+; Method 2 minLC_v003 |
| 9.9 | 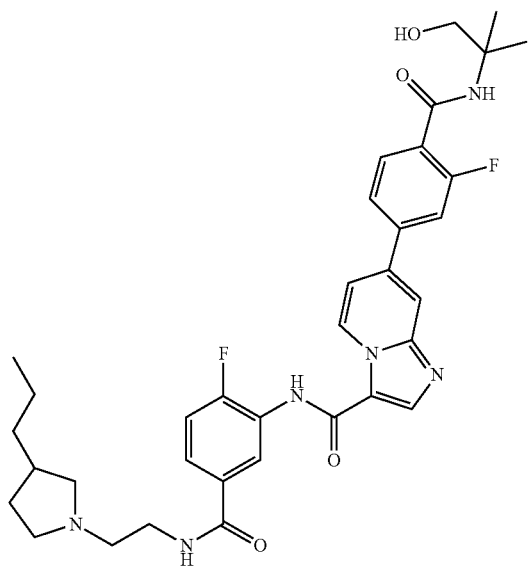 [SMILES: CCCC1CCN(CCNC(=O)c2ccc(F)c(NC(=O)c3cnc4cc(-c5ccc(C(=O)NC(C)(C)CO)c(F)c5)ccn34)c2)C1]<br>7-(3-fluoro-4-((1-hydroxy-2-methylpropan-2-yl)carbamoyl)phenyl)-N-(2-fluoro-5-((2-(3-propylpyrrolidin-1-yl)ethyl)carbamoyl)phenyl)imidazo[1,2-a]pyridine-3-carboxamide | LCMS: Rt 0.79 mins; MS m/z 648.6 [M + H]+; Method 2 minLowpH Int 6B and Int 8A |

TABLE 4-continued

| Ex. | Structure Name | [M + H]⁺/NMR |
|---|---|---|
| 9.10 | 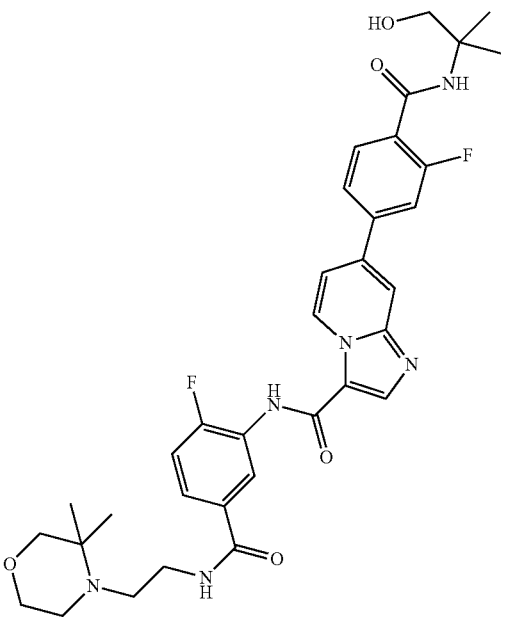 [SMILES: CC(C)(CO)NC(=O)c1ccc(-c2ccn3c(C(=O)Nc4cc(C(=O)NCCN5CCOCC5(C)C)ccc4F)cnc3c2)cc1F]<br>N-(5-((2-(3,3-dimethylmorpholino)ethyl)carbamoyl)-2-fluorophenyl)-7-(3-fluoro-4-((1-hydroxy-2-methylpropan-2-yl)carbamoyl)phenyl)imidazo[1,2-a]pyridine-3-carboxamide | LCMS: Rt 0.74 mins; MS m/z 650.6 [M + H]+; Method 2 minLowpH |
| 9.11 | 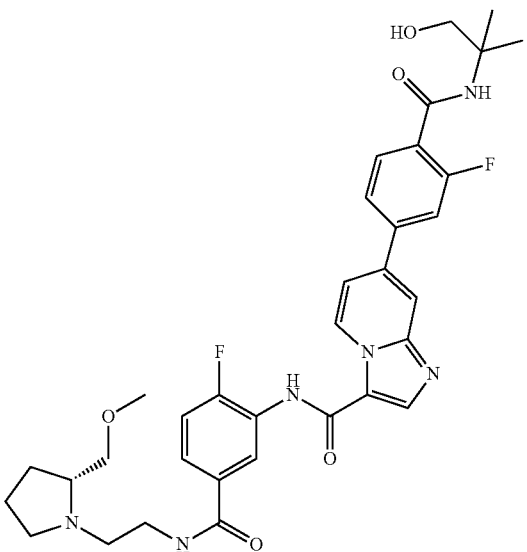<br>(R)-7-(3-fluoro-4-((1-hydroxy-2-methylpropan-2-yl)carbamoyl)phenyl)-N-(2-fluoro-5-((2-(2-(methoxymethyl)pyrrolidin-1-yl)ethyl)carbamoyl)phenyl)imidazo[1,2-a]pyridine-3-carboxamide | LCMS: Rt 0.75 mins; MS m/z 648.7 [M + H]+; Method 2 minLowpH |

TABLE 4-continued

| Ex. | Structure Name | [M + H]⁺/NMR |
|---|---|---|
| 9.12 | 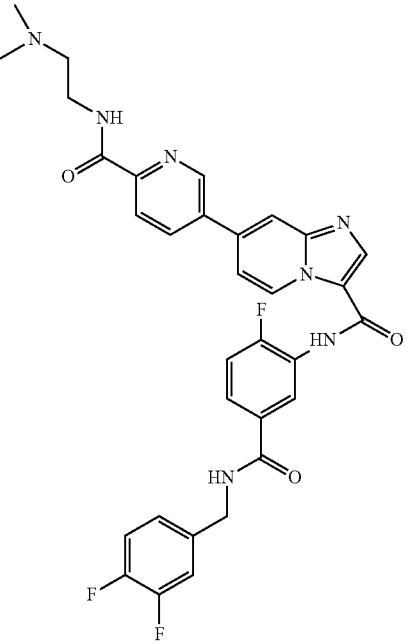 [SMILES: CN(C)CCNC(=O)c1ccc(-c2ccn3c(C(=O)Nc4cc(C(=O)NCc5ccc(F)c(F)c5)ccc4F)cnc3c2)cn1]<br>N-(5-((3,4-Difluorobenzyl)carbamoyl)-2-fluorophenyl)-7-(6-((2-(dimethylamino)ethyl)carbamoyl)pyridin-3-yl)imidazo[1,2-a]pyridine-3-carboxamide | LCMS: Rt 0.74 mins; MS m/z 616.6 [M + H]+; Method 2 minLowpH |
| 9.13 | 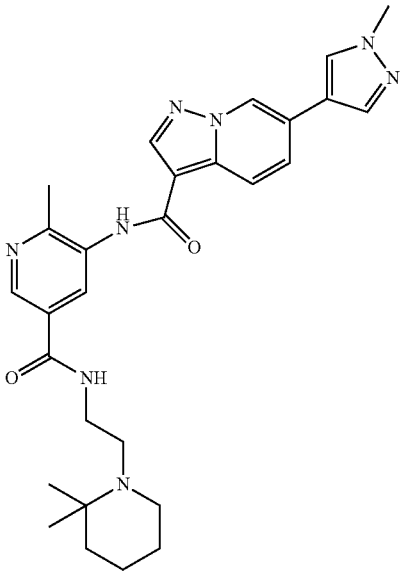 [SMILES: Cc1ncc(C(=O)NCCN2CCCCC2(C)C)cc1NC(=O)c1cnn2cc(-c3cnn(C)c3)ccc12]<br>N-(5-((2-(2,2-Dimethylpiperidin-1-yl)ethyl)carbamoyl)-2-methylpyridin-3-yl)-6-(1-methyl-1H-pyrazol-4-yl)pyrazolo[1,5-a]pyridine-3-carboxamide | LCMS: Rt 0.66 mins; MS m/z 515.7 [M + H]+; Method 2 minLowpH |

TABLE 4-continued
| Ex. | Structure<br>Name | [M + H]⁺/NMR |
|---|---|---|
| 9.14 | 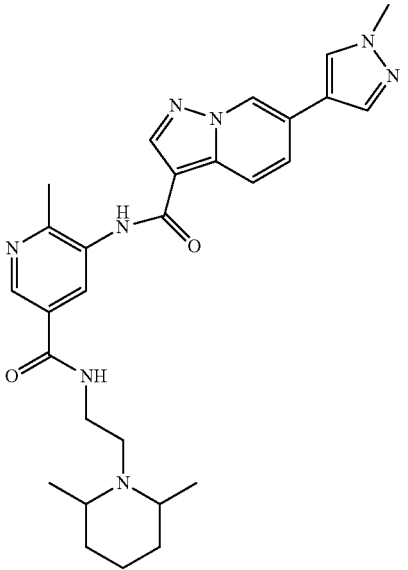 [SMILES: Cc1ncc(C(=O)NCCN2C(C)CCCC2C)cc1NC(=O)c1cnn2cc(-c3cnn(C)c3)ccc12]<br>N-(5-((2-(2,6-dimethyl-piperidin-1-yl)ethyl)carbamoyl)-2-methylpyridin-3-yl)-6-(1-methyl-1H-pyrazol-4-yl)pyrazolo[1,5-a]pyridine-3-carboxamide | LC-MS: Rt 0.62 mins; MS m/z 515.7 {M + H}+; Method 2 minLC_v003 |
| 9.15 | 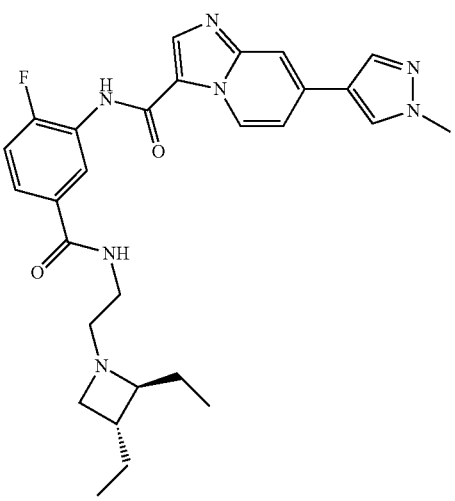 [SMILES: CC[C@@H]1CN(CCNC(=O)c2ccc(F)c(NC(=O)c3cnc4cc(-c5cnn(C)c5)ccn34)c2)[C@H]1CC]<br>N-(5-((2-((2S,3R)-2,3-diethylazetidin-1-yl)ethyl)carbamoyl)-2-fluorophenyl)-7-(1-methyl-1H-pyrazol-4-yl)imidazo[1,2-a]pyridine-3-carboxamide | LC-MS: Rt 0.66 mins; MS m/z 518.5 [M + H]+; Method 2 minLowpHv01 |

Example 10.1

N-(5-(3,4-Difluorobenzylcarbamoyl)-2-fluorophenyl)-7-(6-(((2-hydroxyethyl)(methyl)amino)methyl)pyridin-3-yl)imidazo[1,2-a]pyridine-3-carboxamide

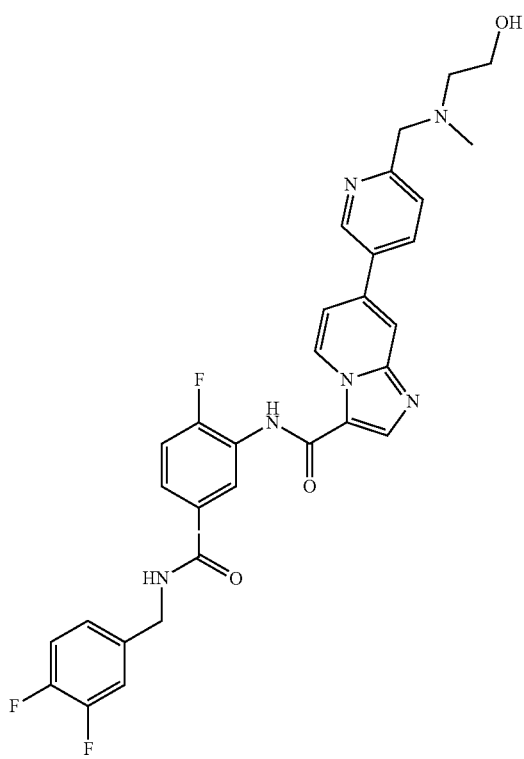 [SMILES: CN(CCO)Cc1ccc(-c2ccn3c(C(=O)Nc4cc(C(=O)NCc5ccc(F)c(F)c5)ccc4F)cnc3c2)cn1]

Step 1: N-(5-(3,4-Difluorobenzylcarbamoyl)-2-fluorophenyl)-7-(6-formylpyridin-3-yl)imidazo[1,2-a]pyridine-3-carboxamide A mixture comprising 7-bromo-N-(5-(3,4-difluorobenzylcarbamoyl)-2-fluorophenyl) imidazo[1,2-a]pyridine-3-carboxamide (Intermediate 3A)(2.7 g, 5.36 mmol), 5-(4,4,5,5-tetramethyl-1,3,2-dioxaborolan-2-yl)picolinaldehyde (1.375 g, 5.90 mmol) and cesium carbonate (6.99 g, 21.46 mmol) in DME (30 ml) and water (3 ml) was treated with PdCl$_2$(dppf).CH$_2$Cl$_2$ adduct (0.219 g, 0.268 mmol). The mixture was placed under nitrogen and heated at 100° C. for 1 hr. The resulting mixture was concentrated in vacuo and the residue was dissolved in 10% trifluoroethanol/CHCl$_3$. The organics were washed with water and NaHCO$_3$ and concentrated in vacuo. Purification by chromatography on silica eluting with 0-30% 2M NH$_3$ in MeOH/DCM afforded the title product;

LC-MS: Rt 0.67 mins; MS m/z 530/531 {M+H}+; Method 2minLC_v003

Step 2: N-(5-(3,4-Difluorobenzylcarbamoyl)-2-fluorophenyl)-7-(6-(((2-hydroxy ethyl)(methyl)amino)methyl)pyridin-3-yl)imidazo[1,2-a]pyridine-3-carboxamide A suspension of N-(5-(3,4-difluorobenzylcarbamoyl)-2-fluorophenyl)-7-(6-formylpyridin-3-yl)imidazo[1,2-a]pyridine-3-carboxamide (step 1)(100 mg, 0.189 mmol), 2-(methylamino)ethanol (70.9 mg, 0.944 mmol) and molecular sieves in EtOH (2 ml) was heated at 70° C. overnight. The mixture was cooled to 0° C. and treated with sodium borohydride (7.15 mg, 0.189 mmol). The mixture was allowed to warm to RT and was stirred overnight. The resulting suspension was removed by filtration and the filtrate was concentrated in vacuo. The residue was partitioned between EtOAc and water. The organic portion was separated, washed with NaHCO$_3$, dried (MgSO$_4$) and concentrated in vacuo. Purification of the residue by preparative chromatography eluting with 25-50% 0.1% TFA acetonitrile/water afforded fractions that were combined and diluted with NaHCO$_3$ and 5% trifluoroethanol/DCM. The organics were separated, dried and concentrated in vacuo to afford a white solid. The solid was triturated with EtOH/Ether to afford the title compound as a white solid;

LC-MS: Rt 0.74 mins; MS m/z 589/590/591 {M+H}+; Method 2minLC_v003

Example 10.2

N-(5-((3,4-difluorobenzyl)carbamoyl)-2-fluorophenyl)-7-(6-((methyl(phenethyl)amino)methyl)pyridin-3-yl)imidazo[1,2-a]pyridine-3-carboxamide

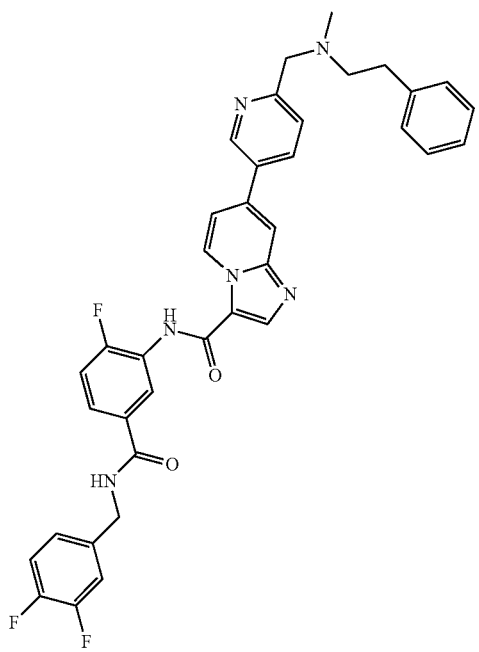 [SMILES: CN(CCc1ccccc1)Cc1ccc(-c2ccn3c(C(=O)Nc4cc(C(=O)NCc5ccc(F)c(F)c5)ccc4F)cnc3c2)cn1]

The title compound was prepared analogously to Example 10.1 from the appropriate amine in step 2;

LC-MS: Rt 0.83 mins; MS m/z 649/650 {M+H}+; Method 2minLC_v003.

The compounds of the following tabulated Examples (Table 5) were prepared by a similar methods to that of Example 10 from the appropriate starting compounds, the preparations of which are detailed herein and in the 'Preparation of Intermediates' section.

TABLE 5
| Ex. | Structure Name | [M + H]⁺/NMR |
|---|---|---|
| 10.2 | 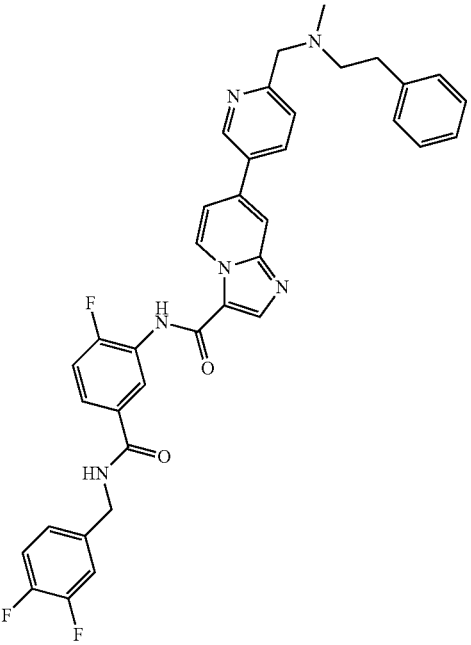 [SMILES: CN(CCc1ccccc1)Cc1ccc(-c2ccn3c(C(=O)Nc4cc(C(=O)NCc5ccc(F)c(F)c5)ccc4F)cnc3c2)cn1]<br>N-(5-((3,4-Difluorobenzyl)carbamoyl)-2-fluorophenyl)-7-(6-((methyl(phenethyl)amino)methyl)pyridin-3-yl)imidazo[1,2-a]pyridine-3-carboxamide | LC-MS: Rt 0.83 mins; MS m/z 649/650 {M + H}+; Method 2 minLC_v003. |
| 10.3 | 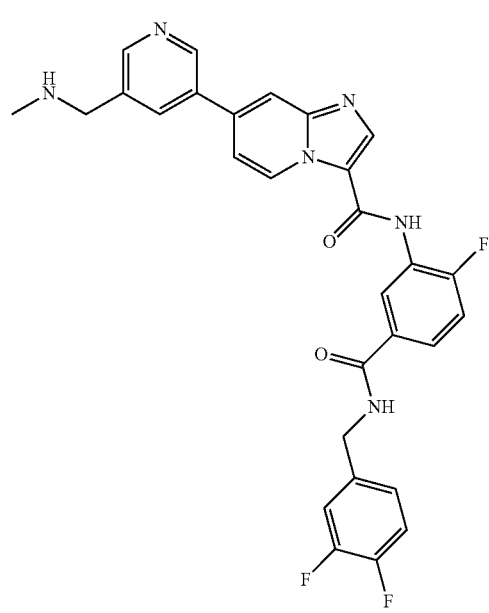 [SMILES: CNCc1cncc(-c2ccn3c(C(=O)Nc4cc(C(=O)NCc5ccc(F)c(F)c5)ccc4F)cnc3c2)c1]<br>N-(5-((3,4-Difluorobenzyl)carbamoyl)-2-fluorophenyl)-7-(5-((methylamino)methyl)pyridin-3-yl)imidazo[1,2-a]pyridine-3-carboxamide | LCMS: Rt 0.71 mins; MS m/z 544.5 [M + H]+; Method A |

TABLE 5-continued
| Ex. | Structure Name | [M + H]⁺/NMR |
|---|---|---|
| 10.4 | 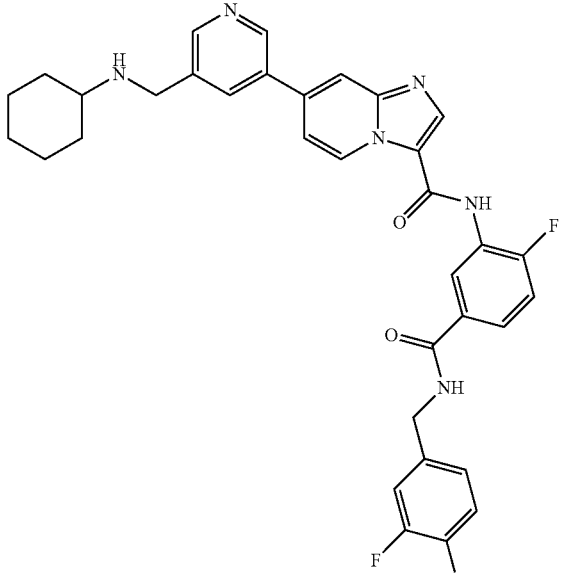<br>7-(5-((Cyclohexylamino)methyl)pyridin-3-yl)-N-(5-((3,4-difluorobenzyl)carbamoyl)-2-fluorophenyl)imidazo[1,2-a]pyridine-3-carboxamide | LCMS: Rt 0.80 mins; MS m/z 612.6 [M + H]+; Method A |
| 10.5 | 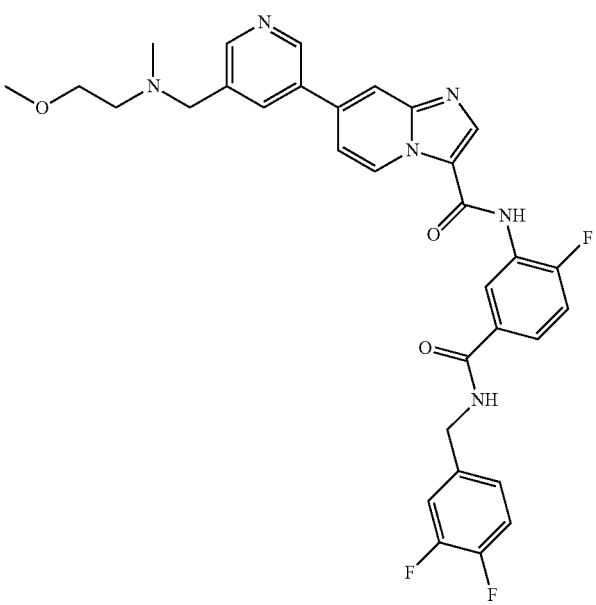 [SMILES: COCCN(C)Cc1cncc(-c2ccn3c(C(=O)Nc4cc(C(=O)NCc5ccc(F)c(F)c5)ccc4F)cnc3c2)c1]<br>N-(5-((3,4-Difluorobenzyl)carbamoyl)-2-fluorophenyl)-7-(5-(((2-methoxyethyl)(methyl)amino)methyl)pyridin-3-yl)imidazo[1,2-a]pyridine-3-carboxamide | LCMS: Rt 0.74 mins; MS m/z 602.6 [M + H]+; Method A |

Preparation of Intermediates

Intermediate 1A Methyl 3-(7-bromoimidazo[1,2-a]pyridine-3-carboxamido)-4-fluorobenzoate

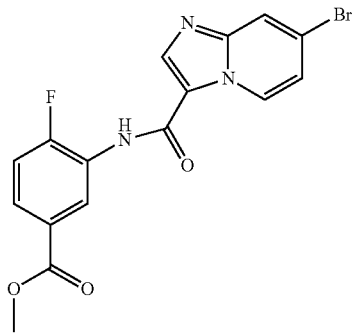 [SMILES: COC(=O)c1ccc(F)c(NC(=O)c2cnc3cc(Br)ccn23)c1]

Step 1: Potassium (Z)-2-chloro-1-ethoxy-3-oxo-prop-1-en-1-olate

A cooled (0° C.) suspension of ethyl 2-chloroacetate (17.47 ml, 163 mmol) and ethyl formate (13.18 ml, 163 mmol) in ether (250 ml) was treated slowly (over 3 hrs) with potassium 2-methylpropan-2-olate (18.31 g, 163 mmol) keeping the temperature below 5° C. The mixture was concentrated in vacuo and the resulting solid was washed with ether and dried (47° C. in a vacuum oven) to afford the title compound;

1H NMR (400 MHz, d6-DMSO) δ 8.95 (1H, s), 3.9 (2H, q), 1.1 (3H, t).

Step 2: Ethyl 7-bromoimidazo[1,2-a]pyridine-3-carboxylate

A solution of 4-bromopyridin-2-amine (10 g, 57.8 mmol) and potassium (Z)-2-chloro-1-ethoxy-3-oxoprop-1-en-1-olate (step 1)(23.4 g, 124 mmol) in ethanol (200 ml) was cooled to 5° C. Sulfuric acid (7.70 ml, 144 mmol) was added dropwise and the reaction heated to reflux at 90° C. for 3 hrs. The mixture was cooled to RT and TEA (20.03 ml, 144 mmol) was slowly added and heating continued at 90° C. for 18 hrs. After cooling to RT, the mixture was filtered and the solid was partitioned between EtOAc and aqueous 2M HCl. The aqueous layer was basified (NaOH, solid pellets) and extracted using EtOAc. The combined organic extracts were dried (MgSO4) and concentrated in vacuo to afford the title compound;

1H NMR (400 MHz, d6-DMSO) δ 9.1 (1H, d), 8.3 (1H, s), 8.2 (1H, s), 7.4 (1H, d), 4.4 (2H, q), 1.4 (3H, t)

Step 3: 7-Bromoimidazo[1,2-a]pyridine-3-carboxylic

Ethyl 7-bromoimidazo[1,2-a]pyridine-3-carboxylate (step 2)(30.81 g, 114 mmol) in MeOH (172 ml) was treated with 2M NaOH (172 ml, 343 mmol) and the mixture was heated to 60° C. for 40 minutes. The volatile solvent was removed in vacuo and the crude material was treated with 2M sodium bisulfate solution to adjust the pH to 6-7. The resulting solid was collected by filtration and added to water (400 ml). The mixture was stirred and heated to 90° C. for 1 h. After cooling to RT, the suspension was filtered and dried in a vacuum over at 40° C. to afford the title product;

LC-MS: Rt 0.59 mins; MS m/z 243.1 {M+H}+; Method 2minLC_v003

Step 4: Methyl 3-(7-bromoimidazo[1,2-a]pyridine-3-carboxamido)-4-fluorobenzoate A mixture comprising 7-bromoimidazo[1,2-a]pyridine-3-carboxylic acid (step 3)(1.8 g, approximately 7.47 mmol) and thionyl chloride (10 ml, 137 mmol) under N2 was heated at reflux for 1.5 hrs. The reaction mixture was concentrated in vacuo and azeotroped with toluene. Methyl 3-amino-4-fluorobenzoate (1.263 g, 7.47 mmol) (pre-dried at 45° C.) was added followed by pyridine and the mixture was stirred at room temperature under N2 overnight. The reaction mixture was diluted with EtOAc and washed with H2O. The resulting solid was collected by filtration. The filtrate was dried (MgSO4) and concentrated in vacuo and triturated with ether to afford cream solid. The solids were combined and dried at 45° C. to afford the title compound;

LC-MS: Rt 0.97 mins; MS m/z 392 {M+H}+; Method 2minLC_v003

1H NMR (400 MHz, DMSO-d6) δ 10.3 (1H, s), 9.4 (1H, d), 8.6 (1H, s), 8.3 (1H, m), 8.2 (1H, s), 7.9 (1H, m), 7.5 (1H, t), 7.4 (1H, d), 3.9 (3H, s).

Intermediate 1B Methyl 3-(7-bromoimidazo[1,2-a]pyridine-3-carboxamido)-4-methylbenzoate

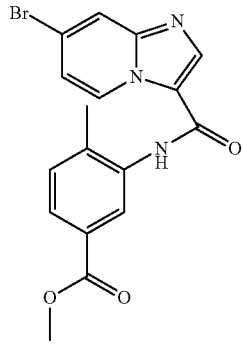 [SMILES: COC(=O)c1ccc(C)c(NC(=O)c2cnc3cc(Br)ccn23)c1]

A mixture comprising 7-bromoimidazo[1,2-a]pyridine-3-carboxylic acid (Intermediate 1A step 3) (750 mg, 3.11 mmol) and thionyl chloride (5 ml, 68.5 mmol) under N2 was heated at reflux for 2 hrs. The mixture was concentrated in vacuo and azeotroped with toluene. Methyl 3-amino-4-methylbenzoate (514 mg, 3.11 mmol) (pre-dried at 45° C.) was added followed by pyridine (5 ml) and the mixture was stirred at room temperature under N2 overnight. The reaction mixture was diluted with EtOAc and washed with sat. NaHCO3, brine, H2O, dried (MgSO4) and concentrated in vacuo. Purification by chromatography on silica eluting with 50-100% EtOAc in iso-hexane afforded the title compound as an orange solid;

LC-MS: Rt 0.94 mins; MS m/z 390/391/392 {M+H}+; Method 2minLC_v003

1H NMR (400 MHz, DMSO-d6) δ 10.0 (1H, s), 9.4 (1H, d), 8.6 (1H, s), 8.2 (1H, d), 8.0 (1H, d), 7.8 (1H, d), 7.5 (1H, d), 7.3 (1H, d), 3.9 (3H, s), 2.4 (3H, s).

121

Intermediate 1C

Methyl 5-(7-bromoimidazo[1,2-a]pyridine-3-carboxamido)-6-methylnicotinate

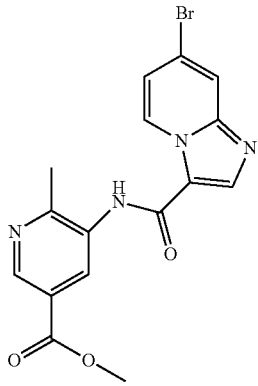 [SMILES: COC(=O)c1cnc(C)c(NC(=O)c2cnc3cc(Br)ccn23)c1]

Step 1: Methyl 2-chloro-6-methyl-5-nitronicotinate

To a suspension of 6-methyl-5-nitro-2-oxo-1,2-dihydropyridine-3-carboxylic acid (commercially available)(12.5 g, 63.1 mmol) in chlorobenzene (210 ml) was added DMF (2.442 ml, 31.5 mmol) followed by POCl₃ (23.52 ml, 252 mmol). The mixture was heated at 133° C. for 1 hr. After cooling to RT, the mixture was concentrated in vacuo. The residue was cooled in an ice bath, treated with MeOH (200 ml, 4944 mmol) and stirred at RT for 16 hrs. The mixture was concentrated in vacuo and the residue was partitioned between water (300 ml) and EtOAc (300 ml). The organics were dried (MgSO₄) and concentrated in vacuo to afford the title compound as a red crystalline solid;

LC-MS: Rt 1.10 mins; MS m/z 230.9 {M+H}+; Method 2minLC_v003

Step 2: Methyl 5-amino-6-methylnicotinate

Methyl 2-chloro-6-methyl-5-nitronicotinate (step 1)(6.9 g, 29.9 mmol) was added to a suspension of ammonium formate (18.87 g, 299 mmol) and 10% Pd(Carbon)(0.522 g, 0.491 mmol) in MeOH (330 ml) and the mixture was heated at reflux for 3 hrs. After cooling to RT, the mixture was filtered through Celite® (filter material) and washed through with MeOH. The solvent was removed in vacuo and the crude product was triturated with EtOAc to give an orange solid. Purification by chromatography on silica eluting with 0-100% EtOAc in iso-hexane afforded the title product.

Step 3: Methyl 5-(7-bromoimidazo[1,2-a]pyridine-3-carboxamido)-6-methylnicotinate The title compound was prepared from 7-bromoimidazo[1,2-a]pyridine-3-carboxylic acid (Intermediate 1A, step 3) and methyl 5-amino-6-methylnicotinate (step 2) analogously to Intermediate 1A;

1H NMR (400 MHz, d6-DMSO) δ 10.21 (1H, s), 9.40 (1H, J=7.4, d), 8.83 (1H, s), 8.55 (1H, s), 8.39 (1H, s), 8.13 (1H, J=1.6, d), 7.35 (1H, J=2.0, 7.4, dd), 3.89 (3H, s), 2.58 (3H, s)

122

Intermediate 1D

Methyl 6-methyl-5-(6-(1-methyl-1H-pyrazol-5-yl)pyrazolo[1,5-a]pyridine-3-carboxamido)nicotinate

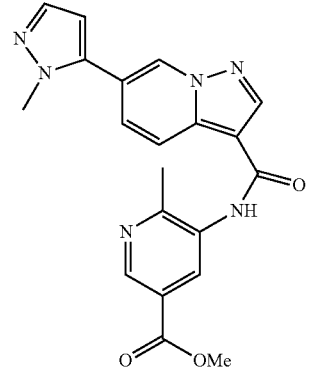 [SMILES: COC(=O)c1cnc(C)c(NC(=O)c2cnn3cc(-c4ccnn4C)ccc23)c1]

Step 1: Ethyl 6-(1-methyl-1H-pyrazol-5-yl)pyrazolo[1,5-a]pyridine-3-carboxylate A mixture comprising ethyl 6-bromopyrazolo[1,5-a]pyridine-3-carboxylate (1.5 g, 5.57 mmol), 1-methyl-5-(4,4,5,5-tetramethyl-1,3,2-dioxaborolan-2-yl)-1H-pyrazole (1.218 g, 5.85 mmol), cesium carbonate (7.26 g, 22.30 mmol) and PdCl₂(dppf).CH₂Cl₂ adduct (91 mg, 0.111 mmol) in DME (10 ml) and water (4.00 ml) was heated using microwave radiation at 70° C. for 1 hr. Further PdCl₂(dppf).CH₂Cl₂ adduct (91 mg, 0.111 mmol) was added and the mixture was heated at 80° C. for 1 hr. 1-Methyl-5-(4,4,5,5-tetramethyl-1,3,2-dioxaborolan-2-yl)-1H-pyrazole (1.218 g, 5.85 mmol) and PdCl₂(dppf).CH₂Cl₂ adduct (91 mg, 0.111 mmol) were added and heating continued at 100° C. for 3 hrs. The mixture was diluted with 10% MeOH in EtOAc (200 ml) and washed with sat. NaHCO3. The organic solvent was removed under vacuum and azeotroped with toluene. The resulting solid was loaded onto silica and purified by chromatography eluting with 0-100% EtOAc in iso-hexane to afford the title compound;

LC-MS: Rt 0.92 mins; MS m/z 271.4 {M+H}+; Method 2minLowpH

Step 2: 6-(1-Methyl-1H-pyrazol-5-yl)pyrazolo[1,5-a]pyridine-3-carboxylic acid The title compound was prepared from ethyl 6-(1-methyl-1H-pyrazol-5-yl)pyrazolo[1,5-a]pyridine-3-carboxylate analogously to Intermediate 1A step 3;

LC-MS: Rt 0.72 mins; MS m/z 243.3 {M+H}+; Method 2minLowpH

Step 3: Methyl 6-methyl-5-(6-(1-methyl-1H-pyrazol-5-yl)pyrazolo[1,5-a]pyridine-3-carboxamido)nicotinate 6-(1-Methyl-1H-pyrazol-5-yl)pyrazolo[1,5-a]pyridine-3-carboxylic acid (step 2) was dissolved in pyridine (5 ml, 61.8 mmol) and 6-methylnicotinate (247 mg, 1.486 mmol) was added. The reaction mixture was stirred under nitrogen overnight. The mixture was diluted with EtOAc (200 ml) and washed with sat. aq. NaHCO₃ (200 ml). The aqueous portion was back-extracted with EtOAc (100 ml) and the combined organic extracts were, dried MgSO₄, filtered and concentrated under vacuum to give yellow solid. Purification of the solid by chromatography on silica eluting with 0-20% 2M NH₃ in MeOH/TBME afforded the title compound;

LC-MS: Rt 0.83 mins; MS m/z 391.3 {M+H}+; Method 2minLowpH

Intermediate 1E 5-(6-Bromopyrazolo[1,5-a]pyridine-3-carboxamido)-6-methylnicotinic acid

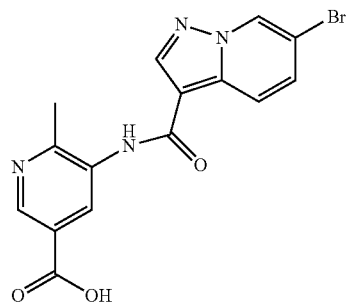 [SMILES: Cc1ncc(C(=O)O)cc1NC(=O)c1cnn2cc(Br)ccc12]

A solution of methyl 5-(7-bromoimidazo[1,2-a]pyridine-3-carboxamido)-6-methylnicotinate (Intermediate 1C)(1 g, 2.57 mmol) and sodium hydroxide (1.028 g, 25.7 mmol) in MeOH (20 ml) was heated at 50° C. overnight. The mixture was concentrated in vacuo and the residue was dissolved in water. The pH was adjusted to pH4 by addition of 1N HCl and the resulting solid was collected by filtration and dried at 45° C. to afford the title compound;

LC-MS: Rt 0.82 mins; MS m/z 376/377 {M+H}+; Method 2minLowpHv01

Intermediate 2A

7-Bromo-N-(5-(2-tert-butoxyethylcarbamoyl)-2-fluorophenyl)imidazo[1,2-a]pyridine-3-carboxamide

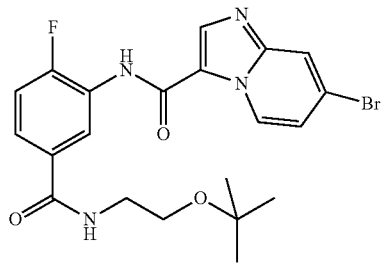 [SMILES: CC(C)(C)OCCNC(=O)c1ccc(F)c(NC(=O)c2cnc3cc(Br)ccn23)c1]

Step 1:
3-Amino-N-(2-tert-butoxyethyl)-4-fluorobenzamide

A mixture comprising 2-tert-butoxyethanamine (1.2 g, 5.12 mmol, 50% w/w) and methyl 3-amino-4-fluorobenzoate (0.866 g, 5.12 mmol) in THF (10 ml) was treated with TBD (0.713 g, 5.12 mmol) and heated at 90° C. for 16 hrs. After cooling to RT, the solvent was removed in vacuo and the residue was partitioned between water and EtOAc. The organic portion was separated and washed with 10% aq citric acid (×2), NaHCO₃ (sat. aq), brine, dried (MgSO₄) and concentrated in vacuo. Purification of the crude product by chromatography on silica eluting with 0-100% EtOAc in iso-hexane afforded the title compound as a clear oil;

LC-MS: Rt 1.09 mins; MS m/z 255 [M+H]+; Method 2minLC_v003

Step 2: 7-Bromo-N-(5-(2-tert-butoxyethylcarbamoyl)-2-fluorophenyl)imidazo[1,2-a]pyridine-3-carboxamide 6-Bromoimidazo[1,2-a]pyridine-3-carboxylic acid (commercially available)(1024 mg, 4.25 mmol) was suspended in toluene (30 ml) and thionyl chloride (1.550 ml, 21.23 mmol) was added. The mixture was heated at 110° C. for 3 hrs. The solvent was removed in vacuo and the resulting residue was treated with a solution of 3-amino-N-(2-tert-butoxyethyl)-4-fluorobenzamide (step 1) (900 mg, 3.54 mmol) in pyridine (10 ml). Molecular sieves were added the mixture was stirred at RT for 16 hrs. In a separate flask, 6-bromoimidazo[1,2-a]pyridine-3-carboxylic acid 640 mg, 2.65 mmol) in toluene (30 ml) was treated with thionyl chloride (0.969 ml, 13.27 mmol) at 110° C. for 3 hrs. The solvent was removed in vacuo and the solid residue was added to the reaction mixture in the original flask. Stirring continued for 3 days. The mixture was poured into MeOH and the resulting suspension was removed by filtration. The filtrate was azeotroped with toluene to give a solid, which was triturated with MeOH to afford the product. The filtrate was concentrated in vacuo and the residue was dissolved in DCM (2% MeOH) and washed with water. The organic portion was dried (MgSO₄) and concentrated in vacuo to afford a solid that was triturated with EtOAc to give the title compound;

LC-MS: Rt 0.96 mins; MS m/z 477(479); 423 (421) [M+H]+; Method 2minLC_v003

Intermediate 2C

7-Bromo-N-(4-fluoro-2-methyl-5-(2-(4-methylpiperazin-1-yl)benzylcarbamoyl)phenyl) imidazo[1,2-a]pyridine-3-carboxamide

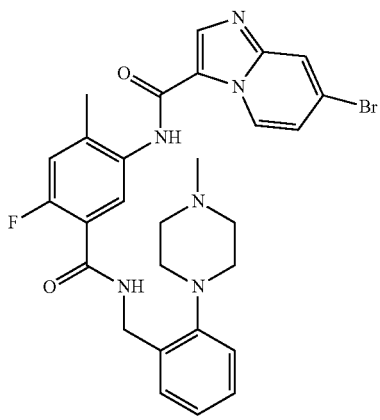 [SMILES: Cc1cc(F)c(C(=O)NCc2ccccc2N2CCN(C)CC2)cc1NC(=O)c1cnc2cc(Br)ccn12]

Step 1: 2-Fluoro-4-methyl-5-nitrobenzoic acid

2-Fluoro-4-methylbenzoic acid (1 g, 6.49 mmol) in H₂SO₄ (19 ml, 356 mmol) was cooled to 0° C. in an ice salt water bath and treated dropwise with mixture of H₂SO₄ (0.763 ml, 14.31 mmol) and nitric acid (0.65 ml, 14.54 mmol) over 10 min. The reaction mixture was stirred at 0° C. for 3 hrs and poured into ice/water (200 ml) and stirred for a further hour. The resulting suspension was collected by filtration, dried in vacuo and collected in EtOH, azeotroping to dryness to afford the title compound.

Step 2: 5-Amino-2-fluoro-4-methylbenzoic acid

2-Fluoro-4-methyl-5-nitrobenzoic acid (900 mg, 4.52 mmol) in MeOH (70 ml) was treated with ammonium formate 1 (425 mg, 22.60 mmol) and Pd (Carbon) (144 mg, 1.356 mmol). The mixture was degassed thoroughly refilling with nitrogen and heated to 60° C. for 2 hrs. The mixture was filtered through silica and washed with MeOH. The filtrate was passed through SCX-2 resin (30 g 0.67 mmol/g) eluting with MeOH (250 ml) followed by 2M ammonia in MeOH (250 ml). The ammonia/MeOH washings were evaporated to dryness and the resulting crude residue was purified by recrystallisation from MeOH to afford the title compound;

LC-MS: Rt 0.53 mins; MS m/z 170 {M+H}⁺; Method 10minLC_v003

Step 3: 5-Amino-2-fluoro-4-methyl-N-(2-(4-methyl-piperazin-1-yl)benzyl)benzamide A mixture comprising (2-(4-methylpiperazin-1-yl)phenyl)methanamine (413 mg, 2.010 mmol) and 5-amino-2-fluoro-4-methylbenzoic acid (step 2)(340 mg, 2.010 mmol) in DMF (3 ml) was treated with DIPEA (0.351 ml, 2.010 mmol) followed by HATU (764 mg, 2.010 mmol) and stirred at 25° C. for 24 hrs. The mixture was partitioned between water and EtOAc. The organic portion was washed with sat. aq. NaHCO₃, 0.5 M LiCl and brine (each back extracted with EtOAc). The combined organic layers were dried (MgSO₄), filtered and evaporated to dryness to give a pink oil. Purification by chromatography on silica eluting with 0-20% MeOH in DCM afforded the title compound;

LC-MS: Rt 0.73 mins; MS m/z 357 {M+H}⁺; Method 2minLC_v003

Step 4: 7-Bromo-N-(4-fluoro-2-methyl-5-(2-(4-methylpiperazin-1-yl)benzylcarbamoyl)phenyl)imidazo[1,2-a]pyridine-3-carboxamide The title compound was prepared from 5-amino-2-fluoro-4-methyl-N-(2-(4-methylpiperazin-1-yl)benzyl)benzamide (step 3) analogously to 7-bromo-N-(5-(2-tert-butoxyethylcarbamoyl)-2-fluorophenyl)imidazo[1,2-a]pyridine-3-carboxamide (Intermediate 2a step 2);

LC-MS: Rt 0.91 mins; MS m/z 579.4/582.4 {M+H}+; Method 2minLC_v003

Intermediate 2D

6-Bromo-N-(5-(2-tert-butoxyethylcarbamoyl)-2-fluorophenyl)pyrazolo[1,5-a]pyridine-3-carboxamide

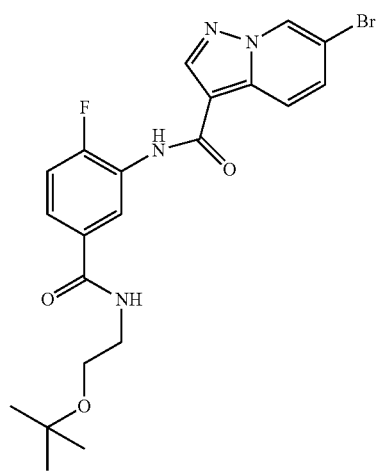 [SMILES: CC(C)(C)OCCNC(=O)c1ccc(F)c(NC(=O)c2cnn3cc(Br)ccc23)c1]

The title compound was prepared analogously to Intermediate 2A by replacing 6-bromoimidazo[1,2-a]pyridine-3-carboxylic acid (step 2) with 6-bromopyrazolo[1,5-a]pyridine-3-carboxylic acid (commercially available);

LC-MS: Rt 1.13 mins; MS m/z 477.1 {M+H}+; Method 2minLC_v003.

Intermediate 3A

7-Bromo-N-(5-(3,4-difluorobenzylcarbamoyl)-2-fluorophenyl)imidazo[1,2-a]pyridine-3-carboxamide

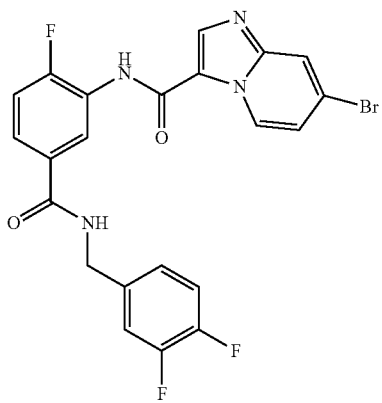 [SMILES: O=C(NCc1ccc(F)c(F)c1)c1ccc(F)c(NC(=O)c2cnc3cc(Br)ccn23)c1]

Step 1:
3-Amino-N-(3,4-difluorobenzyl)-4-fluorobenzamide

A mixture comprising methyl 3-amino-4-fluorobenzoate (2 g, 11.82 mmol), (3,4-difluorophenyl)methanamine (2.54 g, 17.74 mmol) and TBD (1.646 g, 11.82 mmol) in THF (39.4 ml) was heated at 80° C. overnight. After cooling to RT, the mixture was purified by chromatography on silica eluting with 0-20% 2M NH₃ in MeOH/DCM to afford the title compound.

Step 2: 7-Bromo-N-(5-(3,4-difluorobenzylcarbamoyl)-2-fluorophenyl)imidazo[1,2-a]pyridine-3-carboxamide A mixture comprising 7-bromoimidazo[1,2-a]pyridine-3-carboxylic acid (Intermediate 1A step 3) (1.4 g, 5.81 mmol) and thionyl chloride (8.48 ml, 116 mmol) was heated at 100° C. for 1.5 hrs. The mixture was concentrated in vacuo. 3-Amino-N-(3,4-difluorobenzyl)-4-fluorobenzamide (step 1) (1.4 g, 5.00 mmol) and pyridine (16.65 ml) was added and the resulting suspension was stirred at RT for 1 hour. EtOAc and MeOH were added and the mixture was filtered. The white solid was dried to afford the title compound;

LC-MS: Rt 0.74 mins; MS m/z 503 {M+H}+; Method 2minLC_30_v003

Intermediate 4A 6-Bromo-N-(2-methyl-5-(2-(4-methylpiperazin-1-yl)benzylcarbamoyl)phenyl)pyrazolo[1,5-a]pyridine-3-carboxamide

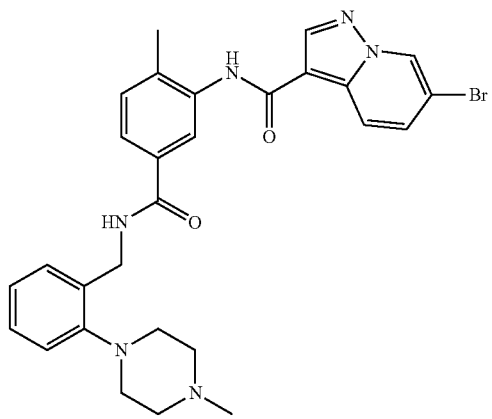 [SMILES: Cc1ccc(C(=O)NCc2ccccc2N2CCN(C)CC2)cc1NC(=O)c1cnn2cc(Br)ccc12]

Step 1: 3-Amino-4-methyl-N-(2-(4-methylpiperazin-1-yl)benzyl)benzamide

A solution of methyl 3-amino-4-methylbenzoate (commercially available) (1.609 g, 9.74 mmol), TBD (2,3,4,6,7,8-hexahydro-1H-pyrimido[1,2-a]pyrimidine) (0.678 g, 4.87 mmol) and (2-(4-methylpiperazin-1-yl)phenyl)methanamine (commercially available) (2 g, 9.74 mmol) in toluene (30 ml) was heated at reflux overnight. The reaction mixture was diluted with EtOAc and washed with sat.NaHCO$_3$ and water. The organic portion was separated, dried (MgSO$_4$) and concentrated in vacuo. The product was purified by chromagraphy on silica eluting with a gradient of 0-20% 2M NH$_3$ in MeOH/DCM to afford the title compound;

LC-MS: Rt 0.64-0.8 mins; MS m/z 339{M+H}+; Method 2minLC_v003

1H NMR (400 MHz, DMSO-d6) d 8.6 (1H, t), 7.25-6.95 (7H, m), 5.0 (2H, s), 4.5 (2H, d), 2.9 (4H, m), (4H, m), 2.2 (3H, s), 2.1 (3H, s).

Step 2: 6-Bromo-N-(2-methyl-5-(2-(4-methylpiperazin-1-yl)benzylcarbamoyl)phenyl)pyrazolo[1,5-a]pyridine-3-carboxamide A mixture comprising 6-bromopyrazolo[1,5-a]pyridine-3-carboxylic acid (commercially available)(196 mg, 0.813 mmol) and thionyl chloride (2 ml, 27.4 mmol) was heated at 60° C. for 1 hr and concentrated in vacuo. To this was added 3-amino-4-methyl-N-(2-(4-methylpiperazin-1-yl)benzyl)benzamide (step 1) (220 mg, 0.651 mmol) and pyridine (5 ml). The reaction was stirred under nitrogen at room temperature for 2 hrs. The mixture was diluted with 10% MeOH in EtOAc and washed with water, sat NaHCO$_3$, brine and concentrated in vacuo. The crude product was purified by chromatography on silica eluting with 0-20% 2M NH$_3$ in MeOH/DCM to afford the title compound;

LC-MS: Rt 0.95 mins; MS m/z 561/563/564 {M+H}+; Method 2minLC_v003

Intermediate 4B

N-(5-(Benzylcarbamoyl)-2-fluorophenyl)-6-iodoimidazo[1,2-a]pyridine-3-carboxamide

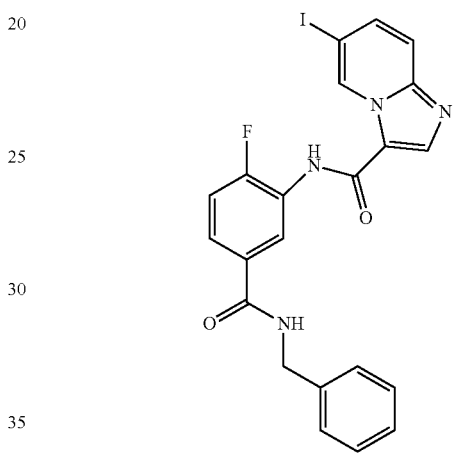

Step 1: 6-Iodoimidazo[1,2-a]pyridine-3-carboxylic acid

The title compound was prepared from 5-iodopyridin-2-amine analogously to 7-bromoimidazo[1,2-a]pyridine-3-carboxylic acid (Intermediate 1A step 2 and step 3); LC-MS: Rt 1.07 mins; MS m/z 317 [M+H]+; Method 2minLC_v003

Step 2: 3-Amino-N-benzyl-4-fluorobenzamide

The title compound was prepared from methyl 3-amino-4-fluorobenzoate, benzylamine and 2,3,4,6,7,8-hexahydro-1H-pyrimido[1,2-a]pyrimidine analogously to 3-amino-4-methyl-N-(2-(4-methylpiperazin-1-yl)benzyl)benzamide (Intermediate 4A, step 1);

1H NMR (400 MHz, DMSO-d6) δ 8.9 (1H, t), 7.4-7.2 (6H, m), 7.0 (2H, d), 5.3 (2H, s), 4.5 (2H, d).

Step 3: N-(5-(Benzylcarbamoyl)-2-fluorophenyl)-6-iodoimidazo[1,2-a]pyridine-3-carboxamide The title compound was prepared from 6-iodoimidazo[1,2-a]pyridine-3-carboxylic acid (step 1) and 3-amino-N-benzyl-4-fluorobenzamide (step 2) analogously 6-bromo-N-(2-methyl-5-(2-(4-methylpiperazin-1-yl)benzylcarbamoyl)phenyl)pyrazolo[1,5-a]pyridine-3-carboxamide (Intermediate 4A);

LC-MS: Rt 0.99 mins; MS m/z 515/516/517 {M+H}+; Method 2minLC_v003

Intermediate 4C

7-Bromo-N-(5-(2-(2,6-cis-dimethylpiperidin-1-yl)ethylcarbamoyl)-2-fluorophenyl)imidazo[1,2-a]pyridine-3-carboxamide

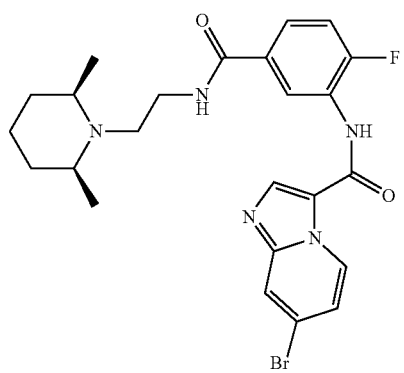 [SMILES: C[C@@H]1CCC[C@H](C)N1CCNC(=O)c1ccc(F)c(NC(=O)c2cnc3cc(Br)ccn23)c1]

Step 1: 3-Amino-N-(2-(2,6-cis-dimethylpiperidin-1-yl)ethyl)-4-fluorobenzamide A mixture comprising 2-(2,6-cis-dimethylpiperidin-1-yl) ethanaminium chloride (4 g, 20.75 mmol) and methyl 3-amino-4-fluorobenzoate (3.51 g, 20.75 mmol) in THF (50 ml) was treated with TBD (2.89 g, 20.75 mmol) and stirred at 80° C. for 16 hrs. A further portion of methyl 3-amino-4-fluoro benzoate (1 g) and TBD (0.5 g) were added and heating continued for 24 hrs. The resulting mixture was partitioned between ethyl acetate and aqueous sodium bicarbonate. The mixture was extracted once with ethyl acetate and once with chloroform. The combined organic layers were dried (MgSO$_4$), filtered and evaporated to dryness. Purification of the residue by chromatography on silica eluting with 0-20% MeOH in DCM afforded the title compound;

LC-MS: Rt 0.71 mins; MS m/z 294 {M+H}+; Method 2minLC_v003.

Step 2: 7-Bromo-N-(5-(2-(2,6-cis-dimethylpiperidin-1-yl)ethylcarbamoyl)-2-fluorophenyl)imidazo[1,2-a]pyridine-3-carboxamide 7-Bromoimidazo[1,2-a]pyridine-3-carboxylic acid (Intermediate 1A step 3) (1.150 g, 4.77 mmol) was suspended in toluene (10 ml) and treated with thionyl chloride (1.045 ml, 14.32 mmol). The mixture was at 100° C. for 2 hrs. The solvent was removed in vacuo and the solid was added to a stirred solution of 3-amino-N-(2-(2,6-cis-dimethyl piperidin-1-yl)ethyl)-4-fluorobenzamide (1.4 g, 4.77 mmol) in dry pyridine (5 ml) containing oven dried molecular sieves. The mixture was stirred at RT under nitrogen atmosphere overnight. The solvent was removed in vacuo and purification of the crude product by chromatography on silica eluting with 0-20% MeOH in DCM afforded the title compound;

LC-MS: Rt 0.82 mins; MS m/z 516{M+H}+; Method 2minLC_v003

Intermediate 4D

6-Bromo-N-(2-fluoro-5-(2-(4-methylpiperazin-1-yl)benzylcarbamoyl)phenyl) pyrazolo[1,5-a]pyridine-3-carboxamide

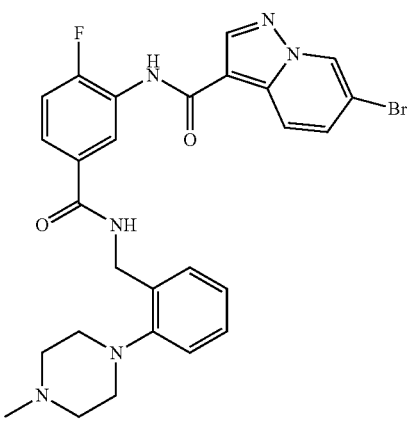 [SMILES: CN1CCN(c2ccccc2CNC(=O)c2ccc(F)c(NC(=O)c3cnn4cc(Br)ccc34)c2)CC1]

The title compound was prepared analogously to Intermediate 4A from the appropriate starting compounds;

LC-MS: Rt 0.95 mins; MS m/z 565/568/569 {M+H}+; Method 2minLC_v003

Intermediate 4E

7-Bromo-N-(5((5,5-dimethyltetrahydrofuran-2-yl)methylcarbamoyl)-2-fluorophenyl) imidazo[1,2-a]pyridine-3-carboxamide

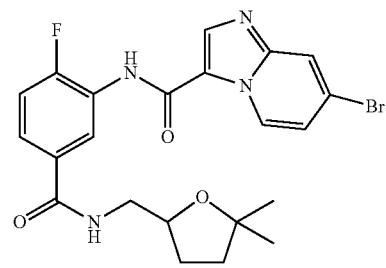 [SMILES: CC1(C)CCC(CNC(=O)c2ccc(F)c(NC(=O)c3cnc4cc(Br)ccn34)c2)O1]

Step 1: 5-(Azidomethyl)-2,2-dimethyltetrahydrofuran 5-(Bromomethyl)-2,2-dimethyltetrahydrofuran (36 g, 186 mmol) in DMF (300 ml) was treated with solid sodium azide (12.73 g, 196 mmol) and heated at 90° C. for 4 hrs. The mixture was allowed to cool to RT and partitioned between water (1.5 l) and ether (2×500 ml). The ether layer was separated and washed with (0.5M) LiCl (500 ml), dried MgSO$_4$, filtered and evaporated to afford the title compound;

Step 2: (5,5-Dimethyltetrahydrofuran-2-yl)methanamine 5-(Azidomethyl)-2,2-dimethyltetrahydrofuran (22 g, 142 mmol) in THF (500 ml) was treated with Triphenylphosphine (39.0 g, 149 mmol) and t stirred for 5 mins. Water (50.0 ml) was added and the reaction mixture was heated at 80° C. for 4 hrs. The mixture was passed through Isolute® SCX-2 resin (200 g 0.67 mmol/g) eluting with MeOH (500 ml), DMSO (100 ml), 20% MeOH:DCM (500 ml), MeOH (500 ml) followed 7M ammonia in MeOH (500 ml). The ammonia layer was evaporated to dryness to afford the title compound.

LC-MS: Rt 0.63 mins; MS m/z 243 [M+H]+; Method 2minLC_v002_low mass

Step 3-4: 7-Bromo-N-(5-((5,5-dimethyltetrahydro-furan-2-yl)methylcarbamoyl)-2-fluorophenyl)imidazo[1,2-a]pyridine-3-carboxamide The title compound was prepared from (5,5-dimethyltetrahydrofuran-2-yl)methan amine (step 2) and methyl 3-amino-4-fluorobenzoate analogously to Intermediate 4A steps 1 and 2;

LC-MS: Rt 0.96 mins; MS m/z 491 [M+H]+; Method 2minLC_v003

Intermediate 4F

7-Bromo-imidazo[1,2-a]pyridine-3-carboxylic acid {5-[((S)-5,5-dimethyl-tetrahydro-furan-2-ylmethyl)-carbamoyl]-2-fluoro-phenyl}-amide

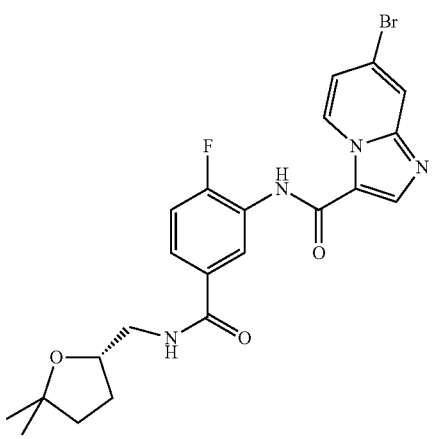 [SMILES: CC1(C)CC[C@@H](CNC(=O)c2ccc(F)c(NC(=O)c3cnc4cc(Br)ccn34)c2)O1]

The title compound was prepared analogously to Intermediate 4E by replacing (5,5-dimethyltetrahydrofuran-2-yl) methanamine (step 3) with (S)-(5,5-dimethyltetrahydrofuran-2-yl)methanamine;

LCMS Rt 0.87 mins; MS m/z 491/492 [M+H]+; Method 2minLC_v003

Intermediate 5A

4-Fluoro-3-(imidazo[1,2-a]pyridine-3-carboxamido) benzoic acid

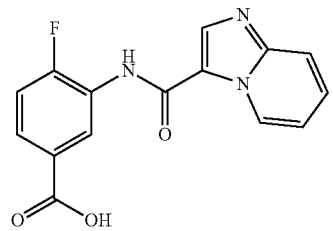 [SMILES: O=C(O)c1ccc(F)c(NC(=O)c2cnc3ccccn23)c1]

Step 1: Imidazo[1,2-a]pyridine-3-carbonyl chloride

A suspension of imidazo[1,2-a]pyridine-3-carboxylic acid (5.270 g, 32.5 mmol) in DCM (200 ml) was treated with oxalyl chloride (3.13 ml, 35.8 mmol) followed by the addition of DMF (0.252 ml, 3.25 mmol). The reaction mixture was stirred at RT overnight. The solvent was removed in vacuo to afford the title compound as a hydrochloride salt;

1H NMR (400 MHz, DMSO-d6) δ 9.48 (1H, d), 8.77 (1H, s), 7.99 (2H, m), 7.56 (1H, t).

Step 2: Methyl 4-fluoro-3-(imidazo[1,2-a]pyridine-3-carboxamido)benzoate

A solution of methyl 3-amino-4-fluorobenzoate (5 g, 29.6 mmol) in pyridine (200 ml) was treated with imidazo[1,2-a]pyridine-3-carbonyl chloride.HCl (step 1)(6.43 g, 29.6 mmol) and the mixture was stirred at RT for 2 days. The mixture was poured into water (30 ml) and a small exotherm was observed. After cooling to RT, the resulting precipitate was filtered and dried in a vacuum oven to afford the title compound; LC-MS: Rt 0.81 mins; MS m/z 314.2 {M+H}+; Method 2minLC_v003

1H NMR (400 MHz, DMSO-d6) δ 10.30 (1H, s), 9.44 (1H, d), 8.63 (1H s), 8.34 (1H, dd), 7.83 (1H, m), 7.78 (1H, d), 7.54 (1H, m), 7.48 (1H, m), 7.20 (1H, t), 3.90 (3H, s).

Step 3: 4-Fluoro-3-(imidazo[1,2-a]pyridine-3-carboxamido)benzoic acid

A suspension of methyl 4-fluoro-3-(imidazo[1,2-a]pyridine-3-carboxamido)benzoate (step 1) (7.2 g, 22.98 mmol) in water (30 ml), THF (45.0 ml) and MeOH (15.00 ml) was treated with lithium hydroxide monohydrate (4.82 g, 115 mmol). The reaction mixture was stirred at RT overnight and concentrated in vacuo to remove THF and MeOH. The resulting mixture was acidified with 2M HCl to yield a solid that was collected by filtration and washed with ether (3×). The white solid was dried in the vacuum oven at 50° C. to afford the title compound as a hydrochloride salt;

LC-MS: Rt 0.71 mins; MS m/z 300.2 {M+H}+; Method 2minLC_v003

1H NMR (400 MHz, DMSO-d6) δ 13.21 (1H, br s), 10.68 (1H, s), 9.60 (1H, s), 8.94 (1H, s), 8.29 (1H, dd), 8.00 (1H, d), 7.86 (2H, m), 7.47 (2H, m).

Intermediate 6A

(S)-2-(2-(Methoxymethyl)pyrrolidin-1-yl)ethanamine

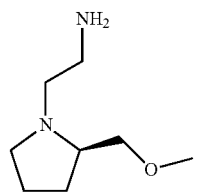

Step 1: (S)-tert-Butyl 2-(2-(methoxymethyl)pyrrolidin-1-yl)ethylcarbamate

A suspension comprising (S)-2-(methoxymethyl)pyrrolidine (1 g, 8.68 mmol), tert-butyl 2-bromoethylcarbamate (1.946 g, 8.68 mmol), triethylamine (1.210 ml, 8.68 mmol) and potassium carbonate (1.200 g, 8.68 mmol) in MeCN (10 ml) was heated at 85° C. overnight. The resulting mixture was filtered and washed with MeCN. Purification of the crude product by chromatography on silica eluting with 0-5% MeOH in DCM afforded the title compound as a colourless oil;

1H NMR (400 MHz), DMSO-d6) δ 3.3 (1H, s), 3.25 (3H, s), 3.15 (1H, m), 3.0 (2H, m), 2.9 (1H, m), 2.8 (1H, m), 2.55 (1H, m), 2.3 (1H, m), 2.15 (1H, q), 1.8 (1H, m), 1.65 (2H, m), 1.45 (1H, m), 1.4 (9H, s).

Step 2: (S)-2-(2-(Methoxymethyl)pyrrolidin-1-yl)ethanamine

A solution of (S)-tert-butyl 2-(2-(methoxymethyl)pyrrolidin-1-yl)ethylcarbamate (step 1)(1.89 g, 7.32 mmol) and in MeOH (5 ml) and treated with 2M HCl in MeOH (10 equivalents) at room temperature over the weekend. The solvent was removed in vacuo to afford the title compound;

1H NMR (400 MHz, CDCl3) δ 3.45 (1H, m), 3.25 (1H, m), 3.1 (1H, m), 2.9 (1H, m), 2.8 (2H, m), 2.6 (1H, m), 2.5 (3H, s), 2.4 (1H, m), 2.2 (1H, m), 0.8 (1H, m), 1.7 (2H, m), 1.6 (1H, m).

The intermediates of the following table (Table 6) were prepared by a similar method to that of Intermediate 6A from the appropriate commercially available starting compounds.

TABLE 6

| Int. | Structure | Name | [M + H]+/NMR |
|---|---|---|---|
| 6B | (structure) | 2-(3-propyl-pyrrolidin-1-yl)ethanamine | 1H NMR (400 MHz, MeOD)δ 3.5 (2H, t), 2.9 (1H, t), 2.75 (3H, m), 2.55 (1H, m), 2 (3H, m), 1.4 (4H, m), 1 (3H, t) |
| 6C | (structure) | (S)-2-(2-(methoxymethyl)pyrrolidin-1-yl)ethanamine | 1H NMR (400 MHz, CDCl3) δ 3.4 (1H, m), 3.38 (3H, s), 3.5 (1H, m), 2.9 (1H, m), 2.8 (2H, m), 2.6 (1H, m), 2.4 (1H, m), 2.2 (1H, q), 1.9 (1H, m), 1.7 (2H, m), 1.6 (1H, m). |
| 6C | (structure) | (R)-2-(2-(methoxymethyl)pyrrolidin-1-yl)ethanamine | 1H NMR (400 MHz, CDCl3) δ 3.45 (1H, m), 3.25 (1H, m), 3.1 (1H, m), 2.9 (1H, m), 2.8 (2H, m), 2.6 (1H, m), 2.5 (3H, s), 2.4 (1H, m), 2.2 (1H, m), 0.8 (1H, m), 1.7 (2H, m), 1.6 (1H, m). |
| 6D | (structure) | (2-(tert-butyl(methyl)amino)ethanamine trifluoroacetate | H NMR (400 MHz), DMSO) δ 8.15 (3H, br), 3.60 (1H, m), 3.30 (2H, m), 3.07 (1H, m), 2.76 (3H, s), 1.34 (9H, s), |
| 6E | (structure) | 2-(2,2-dimethylpiperidin-1-yl)ethanamine | 1H NMR (400 MHz), CD3OD) δ 3.75-3.42 (4H, m), 3.17 (2H, m), 1.87 (4H, m), 1.70 (2H, m), 1.55-0.82 (6H, m), |

Intermediate 7A

3-(5-Carboxy-2-fluorophenylcarbamoyl)-7-(1-methyl-1H-pyrazol-5-yl)imidazo[1,2-a]pyridin-1-ium chloride

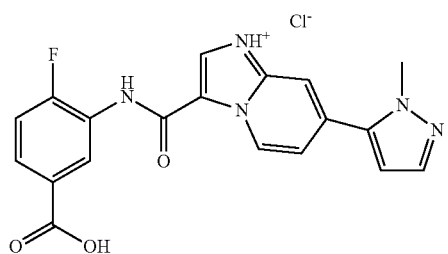 [SMILES: [Cl-] ; Cn1nccc1-c1ccn2c(C(=O)Nc3cc(C(=O)O)ccc3F)c[nH+]c2c1]

The title compound was prepared analogously to 6-methyl-5-(6-(1-methyl-1H-pyrazol-4-yl)pyrazolo[1,5-a]pyridine-3-carboxamido)nicotinic acid (Example 9.0 step 2) from methyl 3-(7-bromoimidazo[1,2-a]pyridine-3-carboxamido)-4-fluorobenzoate (Intermediate 1A) and 1-methyl-5-(4,4,5,5-tetramethyl-[1,3,2]dioxaborolan-2-yl)-1H-pyrazole followed hydrolysis of the resulting methyl ester using sodium hydroxide;

LC-MS: Rt 0.77 mins; MS m/z 380 [M+H]+; Method 2minLC_v003

Intermediate 7B

6-Methyl-5-(6-(1-methyl-1H-pyrazol-5-yl)pyrazolo[1,5-a]pyridine-3-carboxamido) nicotinic acid

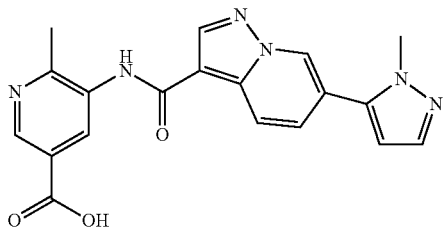 [SMILES: Cc1ncc(C(=O)O)cc1NC(=O)c1cnn2cc(-c3ccnn3C)ccc12]

The title compound was prepared analogously to 6-methyl-5-(6-(1-methyl-1H-pyrazol-4-yl)pyrazolo[1,5-a]pyridine-3-carboxamido)nicotinic acid (Example 9.0 step 2) from Intermediate 1C and 1-methyl-5-(4,4,5,5-tetramethyl-[1,3,2]dioxaborolan-2-yl)-1H-pyrazole followed hydrolysis of the resulting methyl ester using sodium hydroxide;

LC-MS: Rt 0.69 mins; MS m/z 377/378 [M+H]+; Method 2minLC_v003

Intermediate 8A

4-Fluoro-3-(7-(3-fluoro-4-(1-hydroxy-2-methylpropan-2-ylcarbamoyl)phenyl)imidazo[1,2-a]pyridine-3-carboxamido)benzoic acid

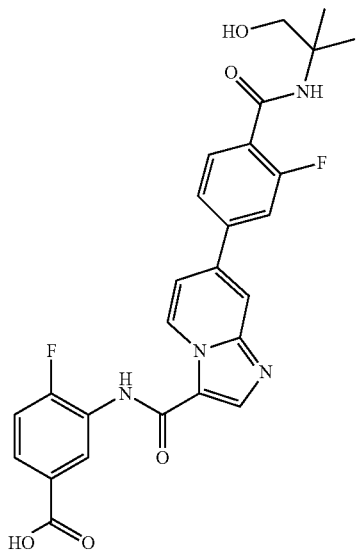 [SMILES: CC(C)(CO)NC(=O)c1ccc(-c2ccn3c(C(=O)Nc4cc(C(=O)O)ccc4F)cnc3c2)cc1F]

Steps 1 and 2: 7-(3-Fluoro-4-(1-hydroxy-2-methylpropan-2-ylcarbamoyl)phenyl)-N-(2-fluoro-5-(1-hydroxy-2-methylpropan-2-ylcarbamoyl)phenyl)imidazo[1,2-a]pyridine-3-carboxamide The title compound was analogously to Example 9.0 steps 2 and 3 from
(1) Intermediate 1A and 4-borono-2-fluorobenzoic acid analogously to Example 9 step 2;
(2) 4-(3-(5-Carboxy-2-fluorophenylcarbamoyl)imidazo[1,2-a]pyridin-7-yl)-2-fluorobenzoic acid (step 1) and 2-amino-2-methylpropan-1-ol;

LC-MS: Rt 0.91 mins; MS m/z 580.4 [M+H]+; Method 2minLowpHv01

Step 2: 4-Fluoro-3-(7-(3-fluoro-4-(1-hydroxy-2-methylpropan-2-ylcarbamoyl)phenyl)imidazo[1,2-a]pyridine-3-carboxamido)benzoic acid 7-(3-Fluoro-4-(1-hydroxy-2-methylpropan-2-ylcarbamoyl)phenyl)-N-(2-fluoro-5-(1-hydroxy-2-methylpropan-2-ylcarbamoyl)phenyl)imidazo[1,2-a]pyridine-3-carboxamide (step 1)(590 mg, 1.129 mmol) in 1,2-dimethoxyethane (10 ml) and water (10.00 ml) was treated with sodium hydroxide (181 mg, 4.52 mmol) and warmed to 60° C. for 1 hr. After cooling to RT, the pH of the mixture was adjusted to pH5 using 2M HCl (2.2 ml). The solvent was removed in vacuo and the resulting crude product was triturated with water to afford the title compound;

LCMS: Rt 0.92 mins; MS m/z 509.4 [M+H]+; Method 2minLowpH

Intermediate 9A

(S)-(5,5-Dimethyltetrahydrofuran-2-yl)methanamine

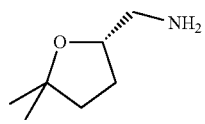

Step 1: (S)-2-((5,5-Dimethyltetrahydrofuran-2-yl)methyl)isoindoline-1,3-dione

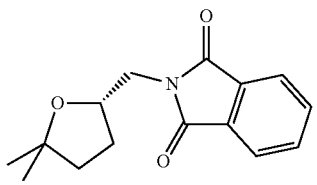 [SMILES: CC1(C)CC[C@@H](CN2C(=O)c3ccccc3C2=O)O1]

To a stirred solution of (S)-(5,5-dimethyltetrahydrofuran-2-yl)methanol (14 g, 108 mmol) and PPh$_3$ (33.8 g, 129 mmol) in THF (140 ml) under N$_2$ was added phthalimide (17.40 g, 118 mmol) to give a suspension. The mixture was cooled to 8° C. and DIAD (27.2 ml, 140 mmol) was added dropwise over 30 mins keeping internal T<10° C. The resulting white slurry was diluted with water (100 ml) and extracted with EtOAc (100 ml). The organics were washed with sat. NaHCO$_3$ (100 ml), brine (100 ml) and dried (MgSO$_4$) and concentrated under reduced pressure. Purification by chromatography on silica eluting with 0-20% EtOAc/iso-hexane afforded the title compound as a white crystalline solid;

LC-MS: Rt 1.02 mins; MS m/z 260 [M+H]+; Method 2minLowpH

Step 2:
(S)-(5,5-Dimethyltetrahydrofuran-2-yl)methanamine hydrochloride

A solution of (S)-2-((5,5-dimethyltetrahydrofuran-2-yl)methyl)isoindoline-1,3-dione (step 1) (21.9 g, 84 mmol) in EtOH (440 ml) was stirred at 60° C. under $N_2$ and hydrazine hydrate (4.51 ml, 93 mmol) was added. The mixture was stirred at 60° C. overnight and then allowed to cool to RT. 2M HCl (60 ml) was added dropwise to adjust pH to pH 1. The slurry was filtered washing with EtOH (50 ml) and the filtrate was concentrated in vacuo to a volume of approximately 50 ml.

The mixture was filtered and washed through with TBME (20 ml) and water (20 ml). The filtrate was washed with TBME (100 ml) and the organic phase was extracted with 2M HCl (50 ml). The acidic aqueous layers were combined and basified to pH 10 with 2M NaOH (~70 ml). This mixture was extracted with TBME (3×200 ml) and the combined organic layers were washed with brine (200 ml) and dried (MgSO$_4$) and filtered. 4M HCl in dioxane (21 ml, 84 mmol) was added slowly and the resulting solution was then concentrated in vacuo to yield a yellow oil. The oil was triturated with diethyl ether to afford the title compound as a pale yellow solid; LC-MS: Rt 0.57 mins; MS m/z 164.1 [M+H]+; Method 2minLowpH

Intermediate 9B (R)-(5,5-Dimethyltetrahydrofuran-2-yl)methanaminium chloride

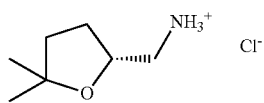

Step 1:
(R)-(5,5-Dimethyltetrahydrofuran-2-yl)methyl 4-methylbenzenesulfonate (R)-(5,5-dimethyltetrahydrofuran-2-yl)methanol [refer Bull chem Soc Japan Vol. 45, No. 3, pp. 916-921, 1972 J Yoshimura et.al p921) (6.7 g, 51.5 mmol) in pyridine (50 ml) was treated with Tosyl-Cl (9.81 g, 51.5 mmol) at room temperature and stirred for 72 hrs. The solvent was removed by evaporation and azeotroping with toluene. The mixture was then partitioned between ethyl acetate and 10% aqueous citric acid. The organics were washed with brine and the aqueous was back extracted with ethyl acetate. The combined organic layers were dried MgSO$_4$, filtered and evaporated to dryness to give a dark oil of (R)-(5,5-dimethyltetrahydrofuran-2-yl)methyl 4-methylbenzenesulfonate;

1H NMR (400 MHz, CDC$_3$) δ 7.85 (2H, d), 7.36 (2H, d), 4.17 (1H, m), 3.98 (2H, d), 2.47 (3H, s), 2.07 (1H, m), 1.85-1.70 (3H, m), 1.18 (6H, s).

Step 2:
(R)-5-(Azidomethyl)-2,2-dimethyltetrahydrofuran (R)-(5,5-Dimethyltetrahydrofuran-2-yl)methyl 4-methylbenzenesulfonate (step 1) (12.8 g, 45.0 mmol) in DMF (50 ml) was treated with sodium azide (3.80 g, 58.5 mmol) at RT overnight then warmed to 70° C. for 3 hrs. Sodium azide (3.80 g, 58.5 mmol) was added and the mixture was warmed to 100° C. for 3 hrs, allowed to cool to RT. The mixture was diluted with water and ethyl acetate. The ethyl acetate layer was washed with 0.5 M lithium chloride in water and the organic layers were dried MgSO$_4$, filtered and evaporated to dryness to afford the title compound; 1H NMR (400 MHz, CDC$_3$) δ 4.17 (1H, m), 3.49 (1H, dd), 3.20 (1H, dd), 2.05 (1H, m), 1.85-1.75 (3H, m), 1.30 (3H, s) 1.23 (3H, s)

Step 3: (R)-(5,5-Dimethyltetrahydrofuran-2-yl) methanaminium chloride (R)-5-(Azidomethyl)-2,2-dimethyltetrahydrofuran (step 2)(6.98 g, 45 mmol) in tetrahydrofuran (175 ml) and Water (35.0 ml) was treated with triphenylphosphine (12.98 g, 49.5 mmol) and stirred at RT for 20 mins then warmed to 80° C. for 4 hrs. Solid Isolute® SCX resin was added and stirred at RT for 1 hr. The SCX-2 resin was washed with 7M ammonia in MeOH (1 L). The ammonia layer was evaporated to dryness with a cool water bath and vacuum >80 mbar. The oily residue was treated with 2N HCl (aq) and the solid precipitate was removed by filtration. The aqueous portion was washed with ethyl acetate and DCM (containing 10% trifluoroethanol). The aqueous was basified by the addition of 2N NaOH (aq) and was extracted with ethyl acetate (×3). The combined organic layers were dried MgSO$_4$, filtered and treated with excess HCl in dioxane before being evaporated to dryness to afford the title compound;

1H NMR (400 MHz, MeOD) δ 4.17 (1H, m), 3.09 (1H, dd), 2.87 (1H, dd), 2.19 (1H, m), 1.95-1.70 (3H, m), 1.31 (3H, s) 1.27 (3H, s).

Intermediate 9C (S)-7-Bromo-N-(5-((5,5-dimethyltetrahydrofuran-2-yl)methylcarbamoyl)-2-fluorophenyl)imidazo[1,2-a]pyridine-3-carboxamide

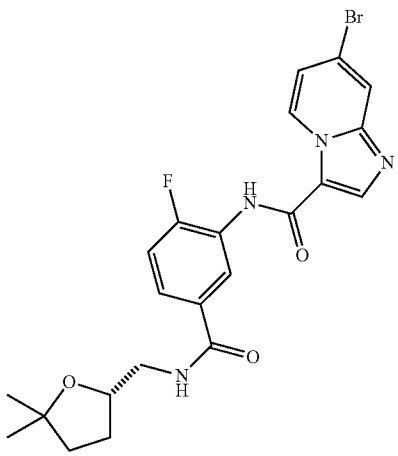

The title compound was prepared from (R)-(5,5-dimethyltetrahydrofuran-2-yl)methanaminium chloride (Intermediate 9B) and 3-(7-Bromoimidazo[1,2-a]pyridine-3-carboxamido)-4-fluoro benzoic acid (prepared by hydrolysis of methyl 3-(7-bromoimidazo[1,2-a]pyridine-3-carboxamido)-4-fluorobenzoate (Intermediate 1A) using NaOH) analogously to Example 7.4 step 1;

Intermediate 9D 2-((2RS,3SR)-2,3-Diethylazetidin-1-yl)ethanamine

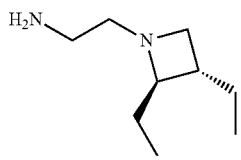

Step 1: (2RS,3RS)-2,3-Diethyl-4-oxoazetidine-1-sulfonyl chloride

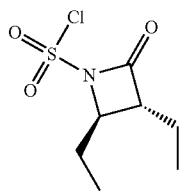

Chlorosulfonylisocyanate (5.17 ml, 59.4 mmol) in DCM (12 ml) was stirred at 25° C. and treated dropwise with (E)-hex-3-ene (7.39 ml, 59.4 mmol) in DCM (6 ml). The mixture was stirred at RT for 72 hrs. The reaction mixture was heated over 6 hrs at 40° C., before being poured onto ice. The mixture was extracted with DCM (3×100 ml) and the combined organics were washed with water (×1), dried MgSO$_4$ and evaporated to dryness to afford the title compound;

1H NMR (400 MHz, CDC$_3$) δ 3.95 (1H, dt), 3.09 (1H, dt), 2.21 (1H, m), 1.85 (3H, m), 1.11 (3H, t), 1.05 (3H, t).

Step 2: (3RS,4RS)-3,4-Diethylazetidin-2-one (2RS,3RS)-2,3-Diethyl-4-oxoazetidine-1-sulfonyl chloride (step 1) (3.2 g, 14.18 mmol) in acetone (7 ml) was treated with thiophenol (2.92 ml, 28.4 mmol) and cooled to −30° C. Pyridine (1.376 ml, 17.01 mmol) in acetone (2.55 ml) was added dropwise over 30 mins, maintaining the temperature around −30° C. After stirring for 30 minutes, water (10 ml) was added slowly and the mixture was filtered. The filtrate was extracted with diethyl ether (5×25 ml) and the combined organic layers were dried MgSO$_4$, filtered and evaporated to dryness (colorless oil 2.3 g). Purification by chromatography on silica eluting with iso-hexane followed by diethyl ether afforded the title compound;

1H NMR (400 MHz, CDCl3) d 3.36 (1H, dt), 2.71 (1H, dt), 1.81 (1H, m), 1.72-1.55 (3H, m), 1.03 (3H, t), 0.95 (3H, t).

Step 3: 2-((2RS,3RS)-2,3-Diethyl-4-oxoazetidin-1-yl)acetonitrile (3RS,4RS)-3,4-diethylazetidin-2-one (step 2)(100 mg, 0.786 mmol) in dry THF (5 ml) was cooled to −78° C. and was treated with lithium bis(trimethylsilyl)amide (0.786 ml, 0.786 mmol) [1 M in THF]. The solution was allowed to warm to 0° C. then re-cooled to 0° C. before adding bromoacetonitrile (0.060 ml, 0.865 mmol). The mixture was allowed to warm to RT overnight. 10% Aqueous citric acid (30 ml) was added and the mixture was extracted with ether (4×40 ml). The combined organic layers were dried MgSO$_4$, filtered and evaporated to dryness. Purification by chromatography on silica eluting with 0-100% Et$_2$O in iso-hexane afforded the title compound; 1H NMR (400 MHz, CDC$_3$) δ 4.21 (1H, d), 3.99 (1H, d), 3.32 (1H, dt), 2.71 (1H, dt), 1.81 (1H, m), 1.72-1.55 (3H, m), 1.03 (3H, t), 0.95 (3H, t).

Step 4: 2-((2RS,3SR)-2,3-Diethylazetidin-1-yl)ethanamine hydrochloride

AlCl$_3$ (3.37 g, 25.3 mmol) in dry ether (140 ml) was added to a stirred suspension of 1M LAlH$_4$ in ether (25.3 ml, 25.3 mmol) in ether (140 ml). The mixture was heated at reflux for 30 mins and after cooling to RT the mixture was transferred by cannula into a solution of 2-((2RS,3RS)-2,3-diethyl-4-oxoazetidin-1-yl)acetonitrile (step 3) (1.4 g, 8.42 mmol) in dry ether (50 ml). Stirring was continued at RT for 16 hrs. The reaction mixture was cooled to 0° C. and Rochelle salt (aq 50 ml) was added. The mixture was allowed to stir at RT for 24 hr. The aqueous was separated and the ether layer was retained. The aqueous was stirred with 10% trifluoroethanol/DCM (250 ml) for 3 hrs then the layers were separated and the aqueous was further stirred with 10% trifluoroethanol/DCM {250 ml} for a further 2 hrs. The remaining aqueous was extracted with 10% trifluoroethanol/DCM (×3). The combined organic layers were treated with 1M HCl in methanol and concentrated in vacuo to afford the title compound;

1H NMR (400 MHz, MeOD) δ 4.55 (1H, dd), 4.33 (1H, t), 4.12 (1H, dd), 3.87 (1H, m), 3.72-3.46 (3H, m), 2.56 (1H, m), 2.16-1.91 (2H, m), 1.71 (2H, m), 1.05 (3H, t), 0.90 (3H, t).

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A method for treating a disease or disorder mediated by the PDGF receptor, wherein the method comprises administering to a subject in need thereof a compound of Formula (I):

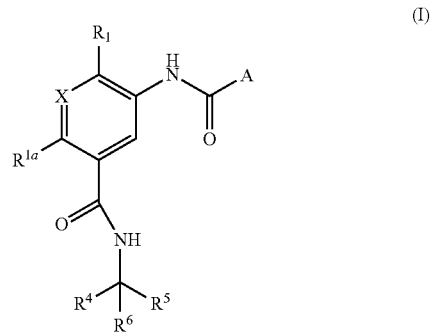

or a pharmaceutically acceptable salt thereof, wherein:
A is

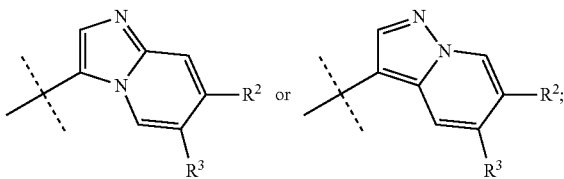

R$^1$ is C$_1$-C$_4$ alkyl; C$_1$-C$_4$ alkoxy optionally substituted by one or more halogen atoms; CN; or halogen;
R$^{1a}$ is H, halogen, C$_1$-C$_4$ alkyl or C$_1$-C$_4$ haloalkyl;
X is N or CH;
R$^2$ is H; C$_1$-C$_8$ alkyl optionally substituted by one or more OH, —NR$^9$R$^{11}$ or C$_1$-C$_4$ alkoxy; C$_1$-C$_8$ haloalkyl; C$_2$-C$_8$ alkynyl substituted by one or more halogen, OH, —NR$^9$R$^{11}$ or C$_1$-C$_4$ alkoxy; C$_3$-C$_{10}$ cycloalkyl; —(C$_1$-C$_4$ alkyl)-C$_3$-C$_8$ cycloalkyl; C$_1$-C$_8$ alkoxy optionally substituted by one or more halogen, —NR$^9$R$^{11}$ or OH; OH; CN; halogen; —(C$_0$-C$_4$ alkyl)-NR$^9$R$^{11}$; —(C$_0$-C$_4$ alkyl)-CO$_2$R$^{15}$; —(C$_0$-C$_4$ alkyl)-C(O)NR$^9$R$^{11}$; —(C$_0$-C$_4$ alkyl)-C$_6$-C$_{14}$ aryl; or —(C$_0$-C$_4$ alkyl)-3 to 14 membered heterocyclyl; wherein the cycloalkyl, —(C$_0$-C$_4$ alkyl)-C$_6$-C$_{14}$ aryl and —(C$_0$-C$_4$ alkyl)-3 to 14 membered heterocyclyl are each optionally substituted by one or more Z$^a$ substituents;
R$^3$ is H; C$_1$-C$_8$ alkyl optionally substituted by one or more OH, —NR$^9$R$^{11}$ or C$_1$-C$_4$ alkoxy; C$_1$-C$_8$ haloalkyl; C$_2$-C$_8$ alkynyl substituted by one or more halogen, OH, —NR$^9$R$^{11}$, or C$_1$-C$_4$ alkoxy; C$_3$-C$_{10}$ cycloalkyl; —(C$_1$-C$_4$ alkyl)-C$_3$-C$_8$ cycloalkyl; C$_1$-C$_8$ alkoxy optionally substituted by one or more halogen, —NR$^9$R$^{11}$ or OH; OH; CN; halogen; —(C$_0$-C$_4$ alkyl)-NR$^9$R$^{11}$; —(C$_0$-C$_4$ alkyl)-CO$_2$R$^{15}$; —(C$_0$-C$_4$ alkyl)-C(O)NR$^9$R$^{11}$; —(C$_0$-C$_4$ alkyl)-C$_6$-C$_{14}$ aryl; or —(C$_0$-C$_4$ alkyl)-3 to 14 membered heterocyclyl; wherein the cycloalkyl, —(C$_0$-C$_4$ alkyl)-C$_6$-C$_{14}$ aryl and —(C$_0$-C$_4$ alkyl)-3 to 14 heterocyclyl are each optionally substituted by one or more Z$^a$ substituents;
each Z$^a$ is independently OH; (C$_0$-C$_4$ alkyl)-C$_6$ aryl; O—C$_6$ aryl; C$_1$-C$_4$ alkyl optionally substituted by one or more OH, CN or —NR$^{19a}$R$^{21a}$; C$_1$-C$_4$ haloalkyl; C$_1$-C$_4$ alkoxy optionally substituted by one or more OH, —CO$_2$R$^{19a}$, —NR$^{19a}$R$^{21a}$ or C$_1$-C$_4$ alkoxy; —NR$^{18a}$C(O)R$^{21a}$; —C(O)NR$^{19a}$R$^{21a}$; —NR$^{18a}$C(O)NR$^{19a}$R$^{21a}$; NR$^{19a}$R$^{21a}$; —(C$_0$-C$_4$ alkyl)-C(O)OR$^{18a}$; —(C$_0$-C$_4$ alkyl)-C(O)R$^{19a}$; oxo; CN; NO$_2$; halogen; —(C$_0$-C$_4$ alkyl)-4 to 6 membered heterocyclyl; or —O-(4 to 6 membered heterocyclyl); wherein the (C$_0$-C$_4$ alkyl)-C$_6$ aryl, O—C$_6$ aryl, —(C$_0$-C$_4$ alkyl)-4 to 6 membered heterocyclyl and —O-(4 to 6 membered heterocyclyl) are each optionally substituted by OH, halogen, C$_1$-C$_4$ alkyl, C$_1$-C$_4$ haloalkyl or C$_1$-C$_4$ alkoxy optionally substituted by one or more halogens;
R$^4$ is H;
R$^5$ is H, C$_1$-C$_4$ alkyl or C$_1$-C$_4$ haloalkyl;
R$^6$ is selected from C$_1$-C$_8$ alkyl optionally substituted by one or more C$_1$-C$_4$ alkoxy or —NR$^{19}$R$^{21}$; C$_1$-C$_8$ haloalkyl; —(C$_0$-C$_4$alkyl)-C$_3$-C$_8$cycloalkyl; C$_1$-C$_8$alkoxy optionally substituted by one or more halogen atoms; —NR$^{19}$R$^{21}$; —(C$_0$-C$_4$ alkyl)-C$_6$-C$_{14}$aryl; and —(C$_0$-C$_4$ alkyl)-3 to 14 membered heterocyclyl; wherein the —(C$_0$-C$_4$alkyl)-C$_3$-C$_8$cycloalkyl, —(C$_0$-C$_4$ alkyl)-C$_6$-C$_{14}$aryl and —(C$_0$-C$_4$ alkyl)-3 to 14 heterocyclyl are each optionally substituted by one or more Z substituents;
each Z is independently selected from (C$_0$-C$_4$ alkyl)-C$_6$ aryl; O—C$_6$ aryl; C$_1$-C$_6$ alkyl optionally substituted by one or more C$_1$-C$_6$ alkoxy, CN or —NR$^{19}$R$^{21}$; C$_1$-C$_6$ haloalkyl; C$_1$-C$_6$ alkoxy optionally substituted by one or more —NR$^{19}$R$^{21}$ or C$_1$-C$_4$ alkoxy; —NR$^{19}$R$^{21}$; (C$_0$-C$_4$ C$_4$ alkyl)-C(O)R$^{19}$; CN; halogen and (C$_0$-C$_4$ alkyl)-4 to 6 membered heterocyclyl; and wherein the aryl and heterocyclyl are each optionally substituted by one or more halogen, C$_1$-C$_6$ alkyl, C$_1$-C$_6$ haloalkyl and C$_1$-C$_6$ alkoxy optionally substituted by one or more halogens;
R$^9$ and R$^{11}$ are each independently selected from H; C$_1$-C$_6$ alkyl optionally substituted by one or more C$_1$-C$_4$ alkoxy or OH; C$_1$-C$_6$ haloalkyl; —(C$_0$-C$_1$alkyl)-C$_3$-C$_6$ cycloalkyl; (C$_0$-C$_4$ alkyl)-C$_6$-C$_{14}$aryl optionally substituted by one or more groups selected from C$_1$-C$_6$ alkyl, C$_1$-C$_6$ alkoxy and halogen; and (C$_0$-C$_4$ alkyl)-3- to 14-membered heterocyclyl optionally substituted by one or more groups selected from halogen, oxo, C$_1$-C$_6$ alkyl and C(O)C$_1$-C$_6$ alkyl; or
R$^9$ and R$^{11}$ together with the nitrogen atom to which they are attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl; 5- to 10-membered heterocyclyl; C$_1$-C$_6$ alkyl; C$_1$-C$_6$ haloalkyl; C$_1$-C$_6$ alkoxy optionally substituted by one or more OH or C$_1$-C$_4$ alkoxy; and C(O)OC$_1$-C$_6$alkyl; wherein the phenyl and heterocyclyl substituent groups are themselves optionally substituted by C$_1$-C$_6$ alkyl, C$_1$-C$_6$ haloalkyl or C$_1$-C$_6$ alkoxy;
R$^{15}$ is selected from H; C$_1$-C$_8$ alkyl; C$_1$-C$_8$ haloalkyl; C$_3$-C$_{10}$ cycloalkyl; (—C$_1$-C$_4$alkyl)-C$_3$-C$_8$ cycloalkyl; —(C$_0$-C$_4$ alkyl)-C$_6$-C$_{14}$aryl and —(C$_0$-C$_4$ alkyl)-3 to 14 membered heterocyclyl group; wherein the C$_3$-C$_{10}$ cycloalkyl, (—C$_1$-C$_4$alkyl)-C$_3$-C$_8$ cycloalkyl, —(C$_0$-C$_4$ alkyl)-C$_6$-C$_{14}$aryl and —(C$_0$-C$_4$ alkyl)-3 to 14 membered heterocyclyl groups are each optionally substituted by one or more Z substituents;
R$^{18a}$ is independently H or C$_1$-C$_6$ alkyl;
R$^{19a}$ and R$^{21a}$ are each independently H; C$_1$-C$_6$ alkyl optionally substituted by one or more C$_1$-C$_4$ alkoxy, —NR$^{22}$R$^{23}$', or OH; C$_1$-C$_6$ haloalkyl; —(C$_0$-C$_1$alkyl)-C$_3$-C$_6$cycloalkyl; —(C$_0$-C$_4$ alkyl)-C$_6$-C$_{14}$aryl optionally substituted by one or more groups selected from C$_1$-C$_6$ alkyl, C$_1$-C$_6$ alkoxy and halogen; or —(C$_0$-C$_4$ alkyl)-3- to 14-membered heterocyclyl optionally substituted by one or more groups selected from halogen, oxo, C$_1$-C$_6$ alkyl and C(O)C$_1$-C$_6$ alkyl; or
R$^{19a}$ and R$^{21a}$ together with the nitrogen atom to which they attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl; 5- to 10-membered heterocyclyl; C$_1$-C$_6$ alkyl; C$_1$-C$_6$ haloalkyl; C$_1$-C$_6$ alkoxy optionally substituted by one or more OH or C$_1$-C$_4$ alkoxy; and C(O)OC$_1$-C$_6$alkyl; wherein the phenyl and heterocyclyl substituent groups are themselves optionally substituted by $C_1$-$C_6$ alkyl, $C_1$-$C_6$ haloalkyl or $C_1$-$C_6$ alkoxy;

$R^{18}$ is independently H or $C_1$-$C_6$ alkyl;

$R^{19}$ and $R^{21}$ are each independently $C_1$-$C_6$ alkyl optionally substituted by one or more $C_1$-$C_4$ alkoxy; $C_1$-$C_6$ haloalkyl; —($C_0$-$C_1$alkyl)-$C_3$-$C_6$cycloalkyl; —($C_0$-$C_4$ alkyl)-$C_6$-$C_{14}$aryl optionally substituted by one or more groups selected from $C_1$-$C_6$ alkyl, $C_1$-$C_6$ alkoxy and halogen; or —($C_0$-$C_4$ alkyl)-3- to 14-membered heterocyclyl, optionally substituted by one or more groups selected from halogen, $C_1$-$C_6$ alkyl and —C(O)$C_1$-$C_6$ alkyl; or $R^{19}$ and $R^{21}$ together with the nitrogen atom to which they attached form a 5- to 10-membered heterocyclyl, which heterocyclyl includes 0 to 3 further heteroatoms selected from N, O and S, the heterocyclyl being optionally substituted by one or more substituents selected from halogen; phenyl; 5- to 10-membered heterocyclyl; $C_1$-$C_6$ alkyl; $C_1$-$C_6$ haloalkyl; $C_1$-$C_6$ alkoxy optionally substituted by one or more $C_1$-$C_4$ alkoxy and C(O)O$C_1$-$C_6$alkyl; wherein the phenyl and heterocyclyl substituent groups are themselves optionally substituted by a substituent selected from $C_1$-$C_6$ alkyl, $C_1$-$C_6$ haloalkyl and $C_1$-$C_6$ alkoxy; and $R^{22}$ and $R^{23}$ are each independently H or $C_1$-$C_6$ alkyl; wherein the disease or condition is asthma, allergic rhinitis, irritable bowel syndrome (IBS), inflammatory bowel disease (IBD), pulmonary arterial hypertension (PAH), pulmonary fibrosis, liver fibrosis, cardiac fibrosis, scleroderma, type I diabetes or type II diabetes.

2. The method of claim 1, wherein the disease or condition is pulmonary arterial hypertension (PAH).

3. The method of claim 1, wherein $R^5$ is H;

$R^6$ is $C_1$-$C_4$ alkyl optionally substituted by one or more $C_1$-$C_4$ alkoxy; phenyl; $C_1$-$C_4$ haloalkyl; tetrahydrofuran; pyrrolidine, —$CH_2$-pyrrolidine or —$CH_2$-piperidine; wherein phenyl, tetrahydrofuran, pyrrolidine, —$CH_2$-pyrrolidine and —$CH_2$-piperidine are each optionally substituted by one or more Z substituents; and each Z is independently $C_1$-$C_4$ alkoxy, halogen, $C_1$-$C_4$ alkyl or $C_1$-$C_4$ haloalkyl.

4. The method of claim 1, wherein $R^2$ is H; $C_1$-$C_8$ alkyl optionally substituted by one or more OH, —$NR^9R^{11}$ or $C_1$-$C_4$ alkoxy; $C_1$-$C_8$ haloalkyl; $C_2$-$C_8$ alkynyl substituted by one or more halogen, OH, —$NR^9R^{11}$ or $C_1$-$C_4$ alkoxy; $C_3$-$C_{10}$ cycloalkyl; —($C_1$-$C_4$ alkyl)-$C_3$-$C_8$ cycloalkyl; $C_1$-$C_8$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-$CO_2R^{15}$; —($C_0$-$C_4$ alkyl)-C(O)$NR^9R^{11}$; —($C_0$-$C_4$ alkyl)-$C_6$-$C_{14}$ aryl; or —($C_0$-$C_4$ alkyl)-3 to 14 membered heterocyclyl; wherein the cycloalkyl, —($C_0$-$C_4$ alkyl)-$C_6$-$C_{14}$ aryl and —($C_0$-$C_4$ alkyl)-3 to 14 membered heterocyclyl are each optionally substituted by one or more $Z^a$ substituents;

$R^3$ is H;

$R^9$ and $R^{11}$ are each independently H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$cycloalkyl; ($C_0$-$C_4$ alkyl)-$C_6$-$C_{14}$ aryl optionally substituted by one or more groups selected from $C_1$-$C_6$ alkyl, $C_1$-$C_6$ alkoxy and halogen; or —($C_0$-$C_4$ alkyl)-5- to 6-membered heterocyclyl optionally substituted by one or more groups selected from halogen, oxo, $C_1$-$C_6$ alkyl and C(O)$C_1$-$C_6$ alkyl;

$Z^a$ is independently OH; ($C_0$-$C_4$ alkyl)-$C_6$ aryl; O—$C_6$ aryl; $C_1$-$C_4$ alkyl optionally substituted by one or more OH, CN or —$NR^{19a}R^{21a}$; $C_1$-$C_4$ haloalkyl; $C_1$-$C_4$ alkoxy optionally substituted by one or more OH, —$CO_2R^{19a}$, —$NR^{19a}R^{21a}$ or $C_1$-$C_4$ alkoxy; —$NR^{18a}C(O)R^{21a}$; —C(O)$NR^{19a}R^{21a}$; —$NR^{18a}C(O)NR^{19a}R^{21a}$; —$NR^{19a}R^{21a}$; ($C_0$-$C_4$ alkyl)-C(O)$OR^{18a}$; ($C_0$-$C_4$ alkyl)-C(O)$R^{19a}$; oxo; CN; $NO_2$; halogen; or ($C_0$-$C_4$ alkyl)-4 to 6 membered heterocyclyl; wherein the aryl and heterocyclyl are each optionally substituted by halogen, $C_1$-$C_4$ alkyl, $C_1$-$C_4$ haloalkyl or $C_1$-$C_4$ alkoxy optionally substituted by one or more halogens;

$R^{18a}$ is independently H or $C_1$-$C_6$ alkyl;

$R^{19a}$ and $R^{21a}$ are each independently H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$cycloalkyl; —($C_0$-$C_4$ alkyl)-$C_6$-$C_{14}$ optionally substituted by one or more groups selected from $C_1$-$C_6$ alkyl, $C_1$-$C_6$ alkoxy and halogen; or ($C_0$-$C_4$ alkyl)-5- to 6-membered heterocyclyl optionally substituted by one or more groups selected from halogen, oxo, $C_1$-$C_6$ alkyl and C(O)$C_1$-$C_6$ alkyl; or $R^{19a}$ and $R^{21a}$ together with the nitrogen atom to which they attached form a 5- to 10-membered heterocyclyl, which heterocyclyl includes 0 to 3 further heteroatoms selected from N, O and S, the heterocyclyl being optionally substituted by one or more substituents selected from OH; halogen; phenyl; 5- to 10-membered heterocyclyl; $C_1$-$C_6$ alkyl; $C_1$-$C_6$ haloalkyl; $C_1$-$C_6$ alkoxy optionally substituted by one or more OH or $C_1$-$C_4$ alkoxy; or C(O)O$C_1$-$C_6$alkyl; wherein the phenyl and heterocyclyl substituent groups are themselves optionally substituted by $C_1$-$C_6$ alkyl, $C_1$-$C_6$ haloalkyl or $C_1$-$C_6$ alkoxy.

5. The method of claim 1, wherein $R^2$ is H; $C_1$-$C_4$ alkyl optionally substituted by one or more OH or —$NR^9R^{11}$; $C_1$-$C_4$ haloalkyl; $C_1$-$C_4$ alkoxy optionally substituted by one or more halogen, —$NR^9R^{11}$ or OH; OH; CN; halogen; —($C_0$-$C_4$ alkyl)-$NR^9R^{11}$; —($C_0$-$C_4$ alkyl)-C(O)$NR^9R^{11}$; phenyl; or —($C_0$-$C_4$ alkyl)-5 to 6 membered heterocyclyl; wherein the phenyl and —($C_0$-$C_4$ alkyl)-5 to 6 membered heterocyclyl are each optionally substituted by one or more $Z^a$ substituents;

$R^3$ is H;

$R^9$ and $R^{11}$ are each independently H; $C_1$-$C_6$ alkyl optionally substituted by one or more $C_1$-$C_4$ alkoxy or OH; $C_1$-$C_6$ haloalkyl; —($C_0$-$C_1$alkyl)-$C_3$-$C_6$cycloalkyl; ($C_0$-$C_4$ alkyl)-$C_6$-$C_{14}$ optionally substituted by one or more groups selected from $C_1$-$C_6$ alkyl, $C_1$-$C_6$ alkoxy and halogen; or ($C_0$-$C_4$ alkyl)-5- to 6-membered heterocyclyl optionally substituted by one or more groups selected from halogen, oxo, $C_1$-$C_6$ alkyl and C(O)$C_1$-$C_6$ alkyl;

each $Z^a$ is independently OH; $C_1$-$C_4$ alkyl optionally substituted by one or more OH or —$NR^{19a}R^{21a}$; $C_1$-$C_4$ haloalkyl; $C_1$-$C_4$ alkoxy optionally substituted by one or more OH, $C_1$-$C_4$ alkoxy or —$NR^{19a}R^{21a}$; —C(O)$NR^{19a}R^{21a}$; CN; halogen or —($C_0$-$C_4$ alkyl)-4 to 6 membered heterocyclyl; wherein the heterocyclyl is optionally substituted by halogen, $C_1$-$C_4$ alkyl, $C_1$-$C_4$ haloalkyl or $C_1$-$C_4$ alkoxy optionally substituted by one or more halogens;

$R^{19a}$ and $R^{21a}$ are each independently H; $C_1$-$C_4$ alkyl optionally substituted by one or more $C_1$-$C_4$ alkoxy or OH; $C_1$-$C_4$ haloalkyl; —($C_0$-$C_1$alkyl)-$C_3$-$C_6$cycloalkyl; —($C_0$-$C_4$ alkyl)-$C_6$-$C_{14}$ optionally substituted by one or more groups selected from $C_1$-$C_6$ alkyl, $C_1$-$C_6$ alkoxy and halogen; or —($C_0$-$C_4$ alkyl)-5- to 6-membered heterocyclyl optionally substituted by one or more groups selected from halogen, oxo, $C_1$-$C_6$ alkyl and $C(O)C_1$-$C_6$ alkyl.

6. The method of claim 1, wherein
$R^1$ is fluorine or methyl;
$R^{1a}$ is H;
$R^2$ is H, F, Br,

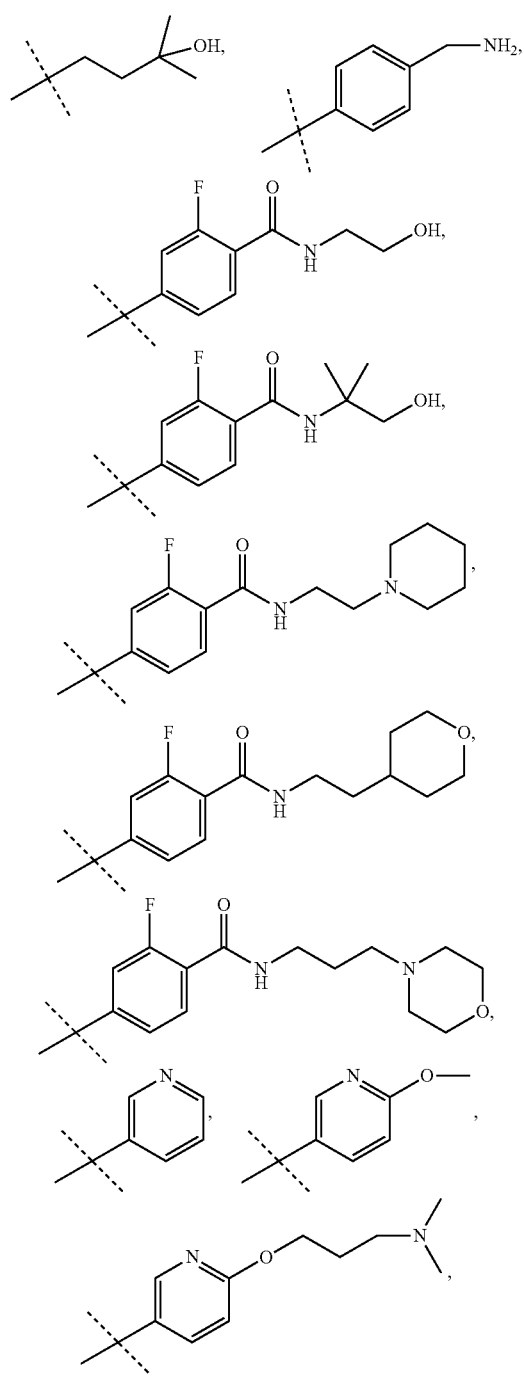

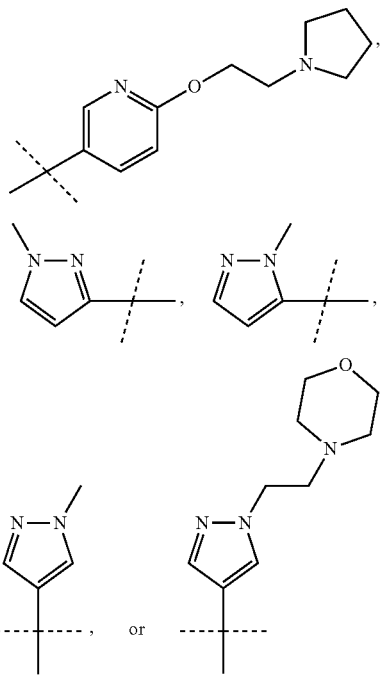

$R^3$ is H;
$R^4$ is H;
$R^5$ is H; and
$R^6$ is

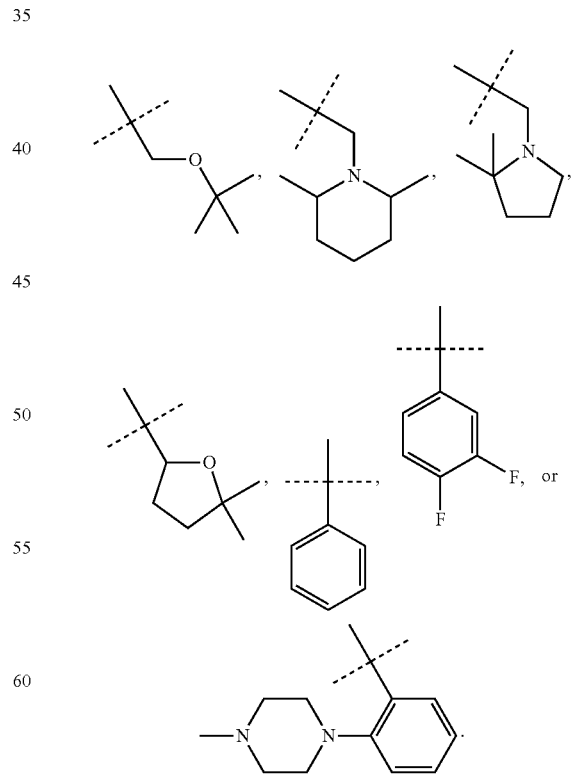

7. The method of claim 1, wherein the compound of Formula (I) is selected from:

N-(2-Fluoro-5-(2-(4-methylpiperazin-1-yl)benzylcarbamoyl)phenyl)-7-(1-methyl-1H-pyrazol-5-yl)imidazo[1,2-a]pyridine-3-carboxamide;

7-(3-Fluoro-4-(2-hydroxyethylcarbamoyl)phenyl)-N-(2-fluoro-5-(2-(4-methylpiperazin-1-yl)benzylcarbamoyl)phenyl)imidazo[1,2-a]pyridine-3-carboxamide;

7-Bromo-N-(2-methyl-5-(2-(4-methylpiperazin-1-yl)benzylcarbamoyl)phenyl)imidazo[1,2-a]pyridine-3-carboxamide;

7-(1-Methyl-1H-pyrazol-5-yl)-N-(2-methyl-5-(2-(4-methylpiperazin-1-yl)benzylcarbamoyl)phenyl)imidazo[1,2-a]pyridine-3-carboxamide;

N-(2-Fluoro-5-(2-(4-methylpiperazin-1-yl)benzylcarbamoyl)phenyl)-7-(pyridine-3-yl)imidazo[1,2-a]pyridine-3-carboxamide;

N-(2-Fluoro-5-(2-(4-methylpiperazin-1-yl)benzylcarbamoyl)phenyl)-7-(1-methyl-1H-pyrazol-4-yl)imidazo[1,2-a]pyridine-3-carboxamide;

N-(5-(3,4-difluorobenzylcarbamoyl)-2-fluorophenyl)-7-(1-methyl-1H-pyrazol-5-yl) imidazo[1,2-a]pyridine-3-carboxamide;

N-(5-(benzylcarbamoyl)-2-fluorophenyl)-6-(1-methyl-1H-pyrazol-3-yl)imidazo[1,2-a]pyridine-3-carboxamide;

N-(4-fluoro-2-methyl-5-(2-(4-methyl piperazin-1-yl)benzylcarbamoyl)phenyl)-7-(pyridine-3-yl)imidazo[1,2-a]pyridine-3-carboxamide;

N-(5-(3,4-difluorobenzylcarbamoyl)-2-fluorophenyl)-7-(6-(3-(dimethylamino) propoxy)pyridine-3-yl)imidazo[1,2-a]pyridine-3-carboxamide;

N-(5-(2-(2,6-cis-dimethylpiperidin-1-yl)ethylcarbamoyl)-2-fluorophenyl)-7-(1-methyl-1H-pyrazol-5-yl)imidazo[1,2-a]pyridine-3-carboxamide;

7-(4-(aminomethyl)phenyl)-N-(2-fluoro-5-(2-(4-methylpiperazin-1-yl)benzylcarbamoyl)phenyl)imidazo[1,2-a]pyridine-3-carboxamide;

N-(5-(2-tert-butoxyethylcarbamoyl)-2-fluorophenyl)-7-(1-(2-morpholinoethyl)-1H-pyrazol-4-yl)imidazo[1,2-a]pyridine-3-carboxamide;

N-(5-((5,5-dimethyltetrahydrofuran-2-yl)methyl carbamoyl)-2-fluorophenyl)-7-(1-(2-morpholinoethyl)-1H-pyrazol-4-yl)imidazo [1,2-a]pyridine-3-carboxamide;

N-(2-fluoro-5-(2-(4-methylpiperazin-1-yl)benzylcarbamoyl)phenyl)-7-(6-methoxy pyridine-3-yl)imidazo [1,2-a]pyridine-3-carboxamide;

N-(2-fluoro-5-(2-(4-methylpiperazin-1-yl)benzylcarbamoyl)phenyl)-6-(1-methyl-1H-pyrazol-5-yl)pyrazolo[1,5-a]pyridine-3-carboxamide;

1-(2-(4-fluoro-3-(7-(pyridine-3-yl)imidazo [1,2-a]pyridine-3-carboxamido)benzamido)ethyl)-2,6-cis-dimethylpiperidine;

N-(5-(2-tert-butoxyethylcarbamoyl)-2-fluorophenyl)-6-(6-(3-(dimethylamino) propoxy)pyridine-3-yl)pyrazolo[1,5-a]pyridine-3-carboxamide;

N-(2-methyl-5-(2-(4-methylpiperazin-1-yl)benzylcarbamoyl)phenyl)-7-(pyridine-3-yl)imidazo[1,2-a]pyridine-3-carboxamide;

1-methyl-4-(2-((6-methyl-5-(7-(1-methyl-1H-pyrazol-5-yl)imidazo[1,2-a]pyridine-3-carboxamido)nicotinamido)methyl)phenyl)piperazin-1-ium;

7-(1-Methyl-1H-pyrazol-4-yl)-imidazo[1,2-a]pyridine-3-carboxylic acid {5-[2-(2,6-cis-dimethyl-piperidin-1-yl)-ethylcarbamoyl]-2-fluoro-phenyl}-amide;

N-(5-(2-tert-Butoxyethylcarbamoyl)-2-fluorophenyl)-7-(6-(3-(dimethylamino)propoxy)pyridin-3-yl)imidazo[1,2-a]pyridine-3-carboxamide;

N-(5-(3,4-Difluorobenzylcarbamoyl)-2-fluorophenyl)-7-(6-(2-(pyrrolidin-1-yl)ethoxy)pyridin-3-yl)imidazo[1,2-a]pyridine-3-carboxamide;

6-(1-Methyl-1H-pyrazol-5-yl)-N-(2-methyl-5-(2-(4-methylpiperazin-1-yl)benzylcarbamoyl)phenyl)pyrazolo[1,5-a]pyridine-3-carboxamide;

N-(2-Bromo-5-(2-(4-methylpiperazin-1-yl)benzylcarbamoyl)phenyl)imidazo[1,2-a]pyridine-3-carboxamide;

N-(2-Bromo-5-(2-(4-methylpiperazin-1-yl)benzylcarbamoyl)phenyl)pyrazolo[1,5-a]pyridine-3-carboxamide;

N-(5-(3,4-Difluorobenzylcarbamoyl)-2-fluorophenyl)-7-(3-hydroxy-3-methyl butyl)imidazo[1,2-a]pyridine-3-carboxamide;

N-(5-(3,4-Difluorobenzylcarbamoyl)-2-fluorophenyl)-7-(3-fluoro-4-(2-(piperidin-1-yl)ethylcarbamoyl)phenyl)imidazo[1,2-a]pyridine-3-carboxamide;

N-(5-(3,4-Difluorobenzylcarbamoyl)-2-fluorophenyl)-7-(3-fluoro-4-(2-(tetrahydro-2H-pyran-4-yl)ethylcarbamoyl)phenyl)imidazo[1,2-a]pyridine-3-carboxamide;

N-(5-(3,4-Difluorobenzylcarbamoyl)-2-fluorophenyl)-7-(3-fluoro-4-(3-morpholino propylcarbamoyl)phenyl)imidazo[1,2-a]pyridine-3-carboxamide;

N-(5-(3,4-Difluorobenzylcarbamoyl)-2-fluorophenyl)-7-(1-(3-(dimethyl amino)propyl)-1H-pyrazol-4-yl)imidazo[1,2-a]pyridine-3-carboxamide;

N-(5-((5,5-Dimethyltetrahydrofuran-2-yl)methylcarbamoyl)-2-fluorophenyl)-7-(5-((tetrahydro-2H-pyran-4-ylamino)methyl)pyridin-3-yl)imidazo[1,2-a]pyridine-3-carboxamide;

(S)—N-(5-4(5,5-Dimethyltetrahydrofuran-2-yl)methyl)carbamoyl)-2-fluorophenyl)-7-(5-(((2-fluoroethyl)amino)methyl)pyridin-3-yl)imidazo[1,2-a]pyridine-3-carboxamide;

(R)—N-(5-(((5,5-dimethyltetrahydrofuran-2-yl)methyl)carbamoyl)-2-fluorophenyl)-7-(5-(((2-methoxyethyl)(methyl)amino)methyl)pyridin-3-yl) imidazo[1,2-a]pyridine-3-carboxamide;

(R)-7-(5-((tert-butylamino)methyl)pyridin-3-yl)-N-(5-4(5,5-dimethyltetrahydrofuran-2-yl)methyl)carbamoyl)-2-fluorophenyl) imidazo[1,2-a]pyridine-3-carboxamide;

N-(5-(3,4-Difluorobenzylcarbamoyl)-2-fluorophenyl)-7-(6-(2-(pyrrolidin-1-yl)ethoxy)pyridin-3-yl)imidazo[1,2-a]pyridine-3-carboxamide;

N-(5-((2-(tert-Butoxy)ethyl)carbamoyl)-2-fluoro phenyl)-7-(6-(2-(pyrrolidin-1-yl) ethoxy)pyridin-3-yl) imidazo[1,2-a]pyridine-3-carboxamide;

N-(5-(((5,5-dimethyl tetrahydrofuran-2-yl)methyl)carbamoyl)-2-fluorophenyl)-7-(6-((1-methyl piperidin-4-yl)oxy)pyridin-3-yl)imidazo[1,2-a]pyridine-3-carboxamide;

6-(1-Methyl-1H-pyrazol-5-yl)-N-(2-methyl-5-(2-(4-methylpiperazin-1-yl)benzylcarbamoyl)phenyl)pyrazolo[1,5-a]pyridine-3-carboxamide;

N-(2-Bromo-5-(2-(4-methylpiperazin-1-yl)benzylcarbamoyl)phenyl)imidazo[1,2-a]pyridine-3-carboxamide;

N-(2-Bromo-5-(2-(4-methylpiperazin-1-yl)benzylcarbamoyl)phenyl)pyrazolo[1,5-a]pyridine-3-carboxamide;

N-(5-(3,4-Difluorobenzylcarbamoyl)-2-fluorophenyl)-7-(3-hydroxy-3-methyl butyl)imidazo[1,2-a]pyridine-3-carboxamide;

N-(5-(3,4-Difluorobenzylcarbamoyl)-2-fluorophenyl)-7-(3-fluoro-4-(2-(piperidin-1-yl)ethylcarbamoyl)phenyl)imidazo[1,2-a]pyridine-3-carboxamide;

N-(5-(3,4-Difluorobenzylcarbamoyl)-2-fluorophenyl)-7-(3-fluoro-4-(2-(tetrahydro-2H-pyran-4-yl)ethylcarbamoyl)phenyl)imidazo[1,2-a]pyridine-3-carboxamide;

N-(5-((2-(2,2-Dimethylpyrrolidin-1-yl)ethyl)carbamoyl)-2-fluorophenyl)-7-(1-methyl-1H-pyrazol-4-yl)imidazo[1,2-a]pyridine-3-carboxamide;

N-(5-(2-(2,2-Dimethylpyrrolidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide;

N-(5-(2-(2,2-Dimethylpyrrolidin-1-yl)ethylcarbamoyl)-2-methylpyridin-3-yl)-6-(3-fluoro-4-(1-hydroxy-2-methylpropan-2-ylcarbamoyl)phenyl)pyrazolo[1,5-a]pyridine-3-carboxamide;

N-(5-(3,4-Difluorobenzylcarbamoyl)-2-fluorophenyl)-7-(3-fluoro-4-(3-morpholino propylcarbamoyl)phenyl)imidazo[1,2-a]pyridine-3-carboxamide;

N-(5-(2-(2,6-cis-Dimethylpiperidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide;

7-(3-Fluoro-4-(2-fluoroethylcarbamoyl)phenyl)-N-(2-fluoro-5-(2-(4-methylpiperazin-1-yl)benzylcarbamoyl)phenyl)imidazo[1,2-a]pyridine-3-carboxamide;

N-(2-Fluoro-5-(2-(4-methylpiperazin-1-yl)benzylcarbamoyl)phenyl)-7-(3-fluoro-5-(2-hydroxy ethylcarbamoyl)phenyl)imidazo[1,2-a]pyridine-3-carboxamide;

N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide;

(S)—N-(2-Fluoro-5-(2-(2-(methoxy methyl) pyrrolidin-1-yl)ethyl carbamoyl)phenyl)-7-(1-methyl-1H-pyrazol-4-yl)imidazo[1,2-a]pyridine-3-carboxamide;

N-(2-Fluoro-5-((2-(3-propylpyrrolidin-1-yl)ethyl)carbamoyl)phenyl)-7-(1-methyl-1H-pyrazol-4-yl)imidazo[1,2-a]pyridine-3-carboxamide;

(R)—N-(2-Fluoro-5-((2-(2-(methoxymethyl) pyrrolidin-1-yl)ethyl) carbamoyl)phenyl)-7-(1-methyl-1H-pyrazol-4-yl)imidazo[1,2-a]pyridine-3-carboxamide;

N-(5-((2-(3,5-Dimethylpiperidin-1-yl)ethyl)carbamoyl)-2-fluorophenyl)-7-(1-methyl-1H-pyrazol-4-yl)imidazo[1,2-a]pyridine-3-carboxamide;

N-(2-fluoro-5-((2-(2,2,6,6-tetra methylpiperidin-1-yl)ethyl)carbamoyl)phenyl)-7-(1-methyl-1H-pyrazol-5-yl)imidazo[1,2-a]pyridine-3-carboxamide;

N-(5-((2-(2,2-dimethylpyrrolidin-1-yl)ethyl)carbamoyl)-2-methylpyridin-3-yl)-6-(1-methyl-1H-pyrazol-5-yl)pyrazolo[1,5-a]pyridine-3-carboxamide;

N-(5-((2-(butyl(ethyl)amino)ethyl)carbamoyl)-2-fluoro phenyl)-7-(3-fluoro-4-((2-hydroxyethyl)carbamoyl)phenyl)imidazo[1,2-a]pyridine-3-carboxamide;

7-(3-fluoro-4-((1-hydroxy-2-methylpropan-2-yl)carbamoyl)phenyl)-N-(2-fluoro-5-((2-(3-propylpyrrolidin-1-yl)ethyl)carbamoyl)phenyl)imidazo[1,2-a]pyridine-3-carboxamide;

N-(5-((2-(3,3-dimethylmorpholino)ethyl)carbamoyl)-2-fluorophenyl)-7-(3-fluoro-4-((1-hydroxy-2-methylpropan-2-yl)carbamoyl)phenyl)imidazo[1,2-a]pyridine-3-carboxamide;

(R)-7-(3-fluoro-4-((1-hydroxy-2-methylpropan-2-yl)carbamoyl)phenyl)-N-(2-fluoro-5-((2-(2-(methoxymethyl)pyrrolidin-1-yl)ethyl) carbamoyl)phenyl)imidazo[1,2-a]pyridine-3-carboxamide;

N-(5-((3,4-Difluorobenzyl)carbamoyl)-2-fluorophenyl)-7-(6-((2-(dimethylamino)ethyl)carbamoyl)pyridin-3-yl)imidazo[1,2-a]pyridine-3-carboxamide;

N-(5-((2-(2,2-Dimethylpiperidin-1-yl)ethyl)carbamoyl)-2-methylpyridin-3-yl)-6-(1-methyl-1H-pyrazol-4-yl)pyrazolo[1,5-a]pyridine-3-carboxamide;

N-(5-((2-(2,6-cis-Dimethylpiperidin-1-yl)ethyl)carbamoyl)-2-methylpyridin-3-yl)-6-(1-methyl-1H-pyrazol-4-yl)pyrazolo[1,5-a]pyridine-3-carboxamide;

N-(5-((2-((2S,3R)-2,3-diethylazetidin-1-yl)ethyl) carbamoyl)-2-fluorophenyl)-7-(1-methyl-1H-pyrazol-4-yl)imidazo[1,2-a]pyridine-3-carboxamide;

N-(5-(3,4-Difluorobenzylcarbamoyl)-2-fluorophenyl)-7-(6-(((2-hydroxyethyl)(methyl)amino)methyl)pyridin-3-yl)imidazo[1,2-a]pyridine-3-carboxamide;

N-(5-((3,4-difluorobenzyl)carbamoyl)-2-fluorophenyl)-7-(6-((methyl(phenethyl)amino)methyl)pyridin-3-yl)imidazo[1,2-a]pyridine-3-carboxamide;

N-(5-((3,4-Difluoro benzyl)carbamoyl)-2-fluorophenyl)-7-(5-((methylamino)methyl)pyridin-3-yl)imidazo[1,2-a]pyridine-3-carboxamide;

7-(5-(((Cyclohexyl amino)methyl)pyridin-3-yl)-N-(5-((3,4-difluorobenzyl) carbamoyl)-2-fluoro phenyl) imidazo[1,2-a]pyridine-3-carboxamide; and N-(5-((3,4-Difluoro benzyl)carbamoyl)-2-fluorophenyl)-7-(5-(((2-methoxyethyl)(methyl)amino)methyl)pyridin-3-yl)imidazo[1,2-a]pyridine-3-carboxamide;

or a pharmaceutically acceptable salt thereof.

8. The method of claim 1, wherein X is N.

9. The method of claim 8, wherein $R^2$ is phenyl or 5- or 6-membered heterocyclyl, each optionally substituted by one, two or three $Z^a$ substituents.

10. The method of claim 9, wherein $R^6$ is ($C_0$-$C_2$ alkyl)-5 to 6 membered heterocyclyl, optionally substituted by one, two or three Z substituents.

11. The method of claim 10, wherein each Z is independently $C_1$-$C_4$ alkoxy, halogen, $C_1$-$C_4$ alkyl or $C_1$-$C_4$ haloalkyl.

12. The method of claim 1, wherein the compound of Formula (I) is N-(5-((2-(2,2-Dimethylpyrrolidin-1-yl)ethyl)carbamoyl)-2-fluorophenyl)-7-(1-methyl-1H-pyrazol-4-yl)imidazo[1,2-a]pyridine-3-carboxamide or a pharmaceutically acceptable salt thereof.

13. The method of claim 1, wherein the compound of Formula (I) is N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide or a pharmaceutically acceptable salt thereof.

14. The method of claim 1, wherein the compound of Formula (I) is N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide or a pharmaceutically acceptable salt thereof.

15. The method of claim 1, wherein the compound of Formula (I) is 7-(1-Methyl-1H-pyrazol-4-yl)-imidazo[1,2-a]pyridine-3-carboxylic acid {5-[2-(2,6-cis-dimethyl-piperidin-1-yl)-ethylcarbamoyl]-2-fluoro-phenyl}-amide or a pharmaceutically acceptable salt thereof.

16. The method of claim 1, wherein the compound of Formula (I) is N-(5-((2-(2,2-dimethylpyrrolidin-1-yl)ethyl)carbamoyl)-2-methylpyridin-3-yl)-6-(1-methyl-1H-pyrazol-5-yl)pyrazolo[1,5-a]pyridine-3-carboxamide or a pharmaceutically acceptable salt thereof.

17. The method of claim 1, wherein the compound of Formula (I) is N-(5-(2-(2,6-cis-Dimethylpiperidin-1-yl)ethylcarbamoyl)-2-fluorophenyl)-7-(3-fluoro-4-(1-hydroxy-2-methylpropan-2-ylcarbamoyl)phenyl)imidazo [1,2-a]pyridine-3-carboxamide or a pharmaceutically acceptable salt thereof.

18. A method of treating pulmonary arterial hypertension in a subject in need thereof, comprising administering to the subject a therapeutically effective amount of a compound selected from:
- N-(5-((2-(2,2-Dimethylpyrrolidin-1-yl)ethyl)carbamoyl)-2-fluorophenyl)-7-(1-methyl-1H-pyrazol-4-yl)imidazo[1,2-a]pyridine-3-carboxamide;
- N-(5-(2-(2,6-cis-Dimethylpiperidin-1-yl)ethylcarbamoyl)-2-fluorophenyl)-7-(1-methyl-1H-pyrazol-5-yl)imidazo[1,2-a]pyridine-3-carboxamide;
- N-(5-(2-(2,2-dimethylpyrrolidin-1-yl)ethylcarbamoyl)-2-methylpyridin-3-yl)-6-(1-methyl-1H-pyrazol-4-yl)pyrazolo[1,5-a]pyridine-3-carboxamide;
- 7-(1-Methyl-1H-pyrazol-4-yl)-imidazo[1,2-a]pyridine-3-carboxylic acid {5-[2-(2,6-cis-dimethyl-piperidin-1-yl)-ethylcarbamoyl]-2-fluoro-phenyl}-amide;
- N-(5-((2-(2,2-dimethylpyrrolidin-1-yl)ethyl)carbamoyl)-2-methylpyridin-3-yl)-6-(1-methyl-1H-pyrazol-5-yl)pyrazolo[1,5-a]pyridine-3-carboxamide; and
- N-(5-(2-(2,6-cis-Dimethylpiperidin-1-yl)ethylcarbamoyl)-2-fluorophenyl)-7-(3-fluoro-4-(1-hydroxy-2-methylpropan-2-ylcarbamoyl)phenyl)imidazo[1,2-a]pyridine-3-carboxamide;

or a pharmaceutically acceptable salt thereof.

* * * * *